(12) United States Patent
Snoke et al.

(10) Patent No.: US 10,926,059 B2
(45) Date of Patent: Feb. 23, 2021

(54) METHOD OF MAKING A SEALED LUMEN AND ASSOCIATED COMPUTING MODULE

(71) Applicant: UVision 360, Inc., RTP, NC (US)

(72) Inventors: Phillip Jack Snoke, Winston-Salem, NC (US); Erich Dreyer, Durham, NC (US)

(73) Assignee: UVision 360, Inc., Raleigh, NC (US)

( * ) Notice: Subject to any disclaimer, the term of this patent is extended or adjusted under 35 U.S.C. 154(b) by 0 days.

(21) Appl. No.: 15/691,209

(22) Filed: Aug. 30, 2017

(65) Prior Publication Data

US 2018/0071481 A1    Mar. 15, 2018

Related U.S. Application Data

(63) Continuation of application No. 15/286,519, filed on Oct. 5, 2016, now abandoned, which is a
(Continued)

(51) Int. Cl.
| | | |
|---|---|---|
| *A61B 1/018* | (2006.01) | |
| *A61B 1/015* | (2006.01) | |
| *A61B 1/005* | (2006.01) | |
| *A61M 25/00* | (2006.01) | |

(Continued)

(52) U.S. Cl.
CPC ........... *A61M 25/003* (2013.01); *A61B 1/005* (2013.01); *A61B 1/00018* (2013.01); *A61B 1/00029* (2013.01); *A61B 1/00045* (2013.01); *A61B 1/0052* (2013.01); *A61B 1/00066* (2013.01); *A61B 1/00121* (2013.01);
(Continued)

(58) Field of Classification Search
CPC ............. A61M 25/003; A61B 1/00016; A61B 1/00018; A61B 1/00029; A61B 1/00045; A61B 1/00066; A61B 1/0011; A61B 1/00121; A61B 1/00154; A61B 1/005; A61B 1/0052; A61B 1/015; A61B 1/018; A61B 1/05; A61B 1/051; A61B 1/0669; A61B 1/0676; A61B 1/0684; A61B 1/07; A61B 17/42; A61B 1/00135; A61B 1/01;
(Continued)

(56) References Cited

U.S. PATENT DOCUMENTS

| | | |
|---|---|---|
| 5,231,989 A | 8/1993 | Middleman et al. |
| 5,483,951 A | 1/1996 | Frassica et al. |

(Continued)

FOREIGN PATENT DOCUMENTS

| | | |
|---|---|---|
| CA | 2593731 C | 1/2015 |
| DE | 19752430 A1 | 7/1999 |

(Continued)

OTHER PUBLICATIONS

ISA/KR, International Search Report and Written Opinion for PCT Patent Application No. PCT/US2016/062368, dated Mar. 14, 2017.

*Primary Examiner* — Timothy J Neal
*Assistant Examiner* — William B Chou
(74) *Attorney, Agent, or Firm* — Mintz Levin Cohn Ferris Glovsky and Popeo, P.C.

(57) ABSTRACT

A method of making an introducer includes providing a translucent material that is formed into an elongate introducer, wherein the introducer has a lumen on an end thereof, and sealing the lumen with a sealing mechanism, wherein the seal is one of a duckbill seal or a one-way valve.

20 Claims, 32 Drawing Sheets

Related U.S. Application Data continuation-in-part of application No. 15/072,077, filed on Mar. 16, 2016, now abandoned, which is a continuation-in-part of application No. 14/942,360, filed on Nov. 16, 2015, now abandoned, which is a continuation-in-part of application No. 14/157,307, filed on Jan. 16, 2014, now abandoned.

(60) Provisional application No. 62/393,636, filed on Sep. 12, 2016, provisional application No. 61/753,413, filed on Jan. 16, 2013.

(51) Int. Cl.
| | | |
|---|---|---|
| *A61B 1/00* | (2006.01) | |
| *A61B 17/42* | (2006.01) | |
| *A61B 1/06* | (2006.01) | |
| *A61B 1/05* | (2006.01) | |
| *A61B 17/00* | (2006.01) | |
| *A61B 90/30* | (2016.01) | |
| *H04N 5/225* | (2006.01) | |
| *A61B 1/002* | (2006.01) | |
| *A61B 1/07* | (2006.01) | |

(52) U.S. Cl.
CPC .......... *A61B 1/00154* (2013.01); *A61B 1/015* (2013.01); *A61B 1/018* (2013.01); *A61B 1/051* (2013.01); *A61B 1/0676* (2013.01); *A61B 17/42* (2013.01); *A61B 1/002* (2013.01); *A61B 1/0011* (2013.01); *A61B 1/00016* (2013.01); *A61B 1/00165* (2013.01); *A61B 1/05* (2013.01); *A61B 1/0661* (2013.01); *A61B 1/0669* (2013.01); *A61B 1/0684* (2013.01); *A61B 1/07* (2013.01); *A61B 2017/003* (2013.01); *A61B 2017/4216* (2013.01); *A61B 2017/4233* (2013.01); *A61B 2090/306* (2016.02); *A61B 2218/002* (2013.01); *A61B 2218/007* (2013.01); *H04N 5/2258* (2013.01); *H04N 2005/2255* (2013.01)

(58) Field of Classification Search
CPC .......... A61B 1/00034; A61B 2017/003; A61B 2017/3445
See application file for complete search history.

(56) References Cited

U.S. PATENT DOCUMENTS

| | | | |
|---|---|---|---|
| 5,611,769 A | 3/1997 | Monroe | |
| 5,645,519 A | 7/1997 | Lee et al. | |
| 5,823,940 A | 10/1998 | Newman | |
| 5,961,486 A | 10/1999 | Twardowski et al. | |
| 6,110,103 A | 8/2000 | Donofrio | |
| 6,371,909 B1 * | 4/2002 | Hoeg | A61B 1/00096 600/112 |
| 6,419,626 B1 | 7/2002 | Yoon | |
| 6,482,169 B1 | 11/2002 | Kuhle | |
| 6,572,631 B1 * | 6/2003 | McCartney | A61B 1/32 606/119 |
| 6,749,580 B2 | 6/2004 | Work et al. | |
| 6,761,684 B1 | 7/2004 | Speier | |
| 6,863,651 B2 | 3/2005 | Remijan et al. | |
| 6,926,005 B1 | 8/2005 | Colman et al. | |
| 6,958,035 B2 | 10/2005 | Friedman et al. | |
| 7,008,401 B2 | 3/2006 | Thompson et al. | |
| 7,029,467 B2 | 4/2006 | Currier et al. | |
| 7,233,820 B2 | 6/2007 | Gilboa | |
| 7,776,005 B2 | 8/2010 | Haggstrom et al. | |
| 7,815,564 B2 | 10/2010 | Geitz et al. | |
| 7,921,848 B2 | 4/2011 | Nikolchev et al. | |
| 8,079,364 B2 | 12/2011 | Lowe et al. | |
| 8,251,975 B2 | 8/2012 | Atkins et al. | |
| 8,460,182 B2 | 6/2013 | Ouyang et al. | |
| 8,532,747 B2 * | 9/2013 | Nock | A61B 90/39 600/431 |
| 8,814,846 B2 | 8/2014 | Horton et al. | |
| 8,834,357 B2 | 9/2014 | Oskin et al. | |
| 8,845,522 B2 | 9/2014 | McIntyre et al. | |
| 8,961,452 B2 | 2/2015 | Purdy | |
| 9,011,412 B2 | 4/2015 | Albritton et al. | |
| 9,039,649 B2 | 5/2015 | Neisz et al. | |
| 9,370,650 B2 | 6/2016 | Hanson et al. | |
| 9,855,021 B2 * | 1/2018 | Abraham | A61B 8/12 |
| 2002/0137984 A1 | 9/2002 | Chhibber et al. | |
| 2005/0049459 A1 | 3/2005 | Hern | |
| 2005/0096642 A1 * | 5/2005 | Appling | A61B 18/24 606/15 |
| 2005/0272975 A1 | 12/2005 | McWeeney et al. | |
| 2005/0283048 A1 | 12/2005 | Gill et al. | |
| 2006/0149186 A1 * | 7/2006 | Wantink | A61M 25/10 604/96.01 |
| 2007/0118019 A1 | 5/2007 | Mitani et al. | |
| 2007/0129605 A1 | 6/2007 | Schaaf | |
| 2007/0167682 A1 | 7/2007 | Goldfarb et al. | |
| 2007/0197871 A1 | 8/2007 | Geitz et al. | |
| 2008/0076966 A1 | 3/2008 | Isaacson | |
| 2008/0154091 A1 | 6/2008 | Dejima et al. | |
| 2008/0167527 A1 | 7/2008 | Slenker et al. | |
| 2008/0249366 A1 * | 10/2008 | Gruber | A61B 1/303 600/154 |
| 2009/0054728 A1 | 2/2009 | Trusty | |
| 2009/0076498 A1 * | 3/2009 | Saadat | A61B 18/1492 606/41 |
| 2009/0299336 A1 * | 12/2009 | Jay-Robinson | A61B 1/00137 604/533 |
| 2010/0016757 A1 | 1/2010 | Greenburg et al. | |
| 2010/0145142 A1 | 6/2010 | Begemann et al. | |
| 2010/0249513 A1 | 9/2010 | Tydlaska | |
| 2010/0261967 A1 | 10/2010 | Pacey et al. | |
| 2010/0280368 A1 | 11/2010 | Can et al. | |
| 2010/0305503 A1 | 12/2010 | Fang et al. | |
| 2010/0331883 A1 * | 12/2010 | Schmitz | A61B 10/0275 606/249 |
| 2011/0071349 A1 | 3/2011 | Drontle et al. | |
| 2011/0276113 A1 | 11/2011 | Cybulski | |
| 2011/0319718 A1 | 12/2011 | Hakanen et al. | |
| 2012/0016260 A1 | 1/2012 | To | |
| 2012/0143006 A1 | 6/2012 | Avitsian et al. | |
| 2012/0259406 A1 * | 10/2012 | Schreck | A61F 2/07 623/1.27 |
| 2012/0289858 A1 * | 11/2012 | Ouyang | A61B 10/0275 600/562 |
| 2013/0023729 A1 | 1/2013 | Vazales et al. | |
| 2013/0053645 A1 | 2/2013 | Weitzner et al. | |
| 2013/0281782 A1 | 10/2013 | Zhou | |
| 2014/0107416 A1 | 4/2014 | Birnkrant | |
| 2014/0200402 A1 | 7/2014 | Snoke et al. | |
| 2014/0357955 A1 | 12/2014 | Avitsian et al. | |
| 2015/0112132 A1 | 4/2015 | Nieman et al. | |
| 2015/0202089 A1 * | 7/2015 | Campbell | A61F 11/002 600/478 |
| 2015/0320406 A1 | 11/2015 | Sethi | |
| 2015/0374221 A1 | 12/2015 | Sahney et al. | |
| 2016/0066770 A1 | 3/2016 | Barbato et al. | |
| 2017/0055813 A1 | 3/2017 | London Brown et al. | |
| 2017/0273716 A1 | 9/2017 | Garofalo et al. | |
| 2018/0098761 A1 | 4/2018 | Stanwood | |
| 2018/0199797 A1 | 7/2018 | London Brown et al. | |
| 2019/0142400 A1 | 5/2019 | Washburn et al. | |
| 2019/0231177 A1 | 8/2019 | Dreyer et al. | |

FOREIGN PATENT DOCUMENTS

| | | |
|---|---|---|
| DE | 19752430 C2 | 5/2000 |
| DE | 10045036 C1 | 7/2002 |
| WO | 2017087579 A1 | 5/2017 |
| WO | 2019094948 A1 | 5/2019 |

* cited by examiner

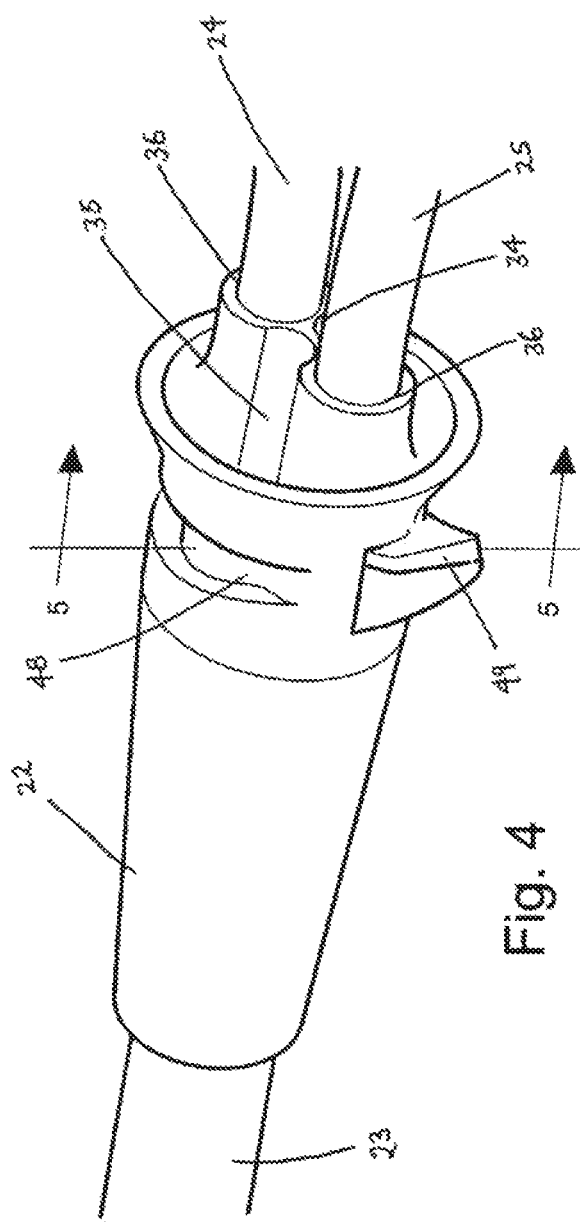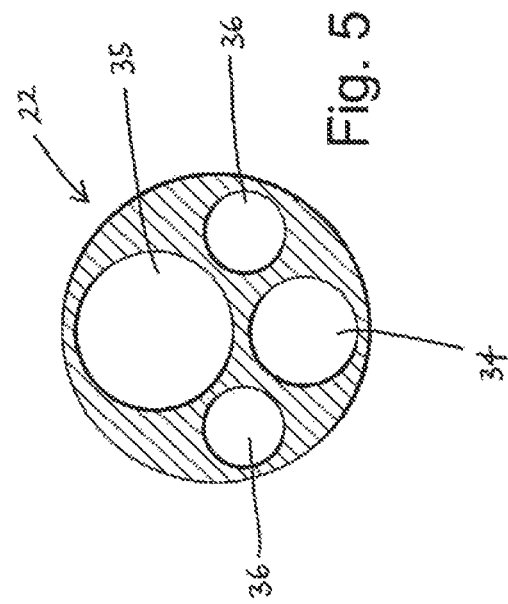

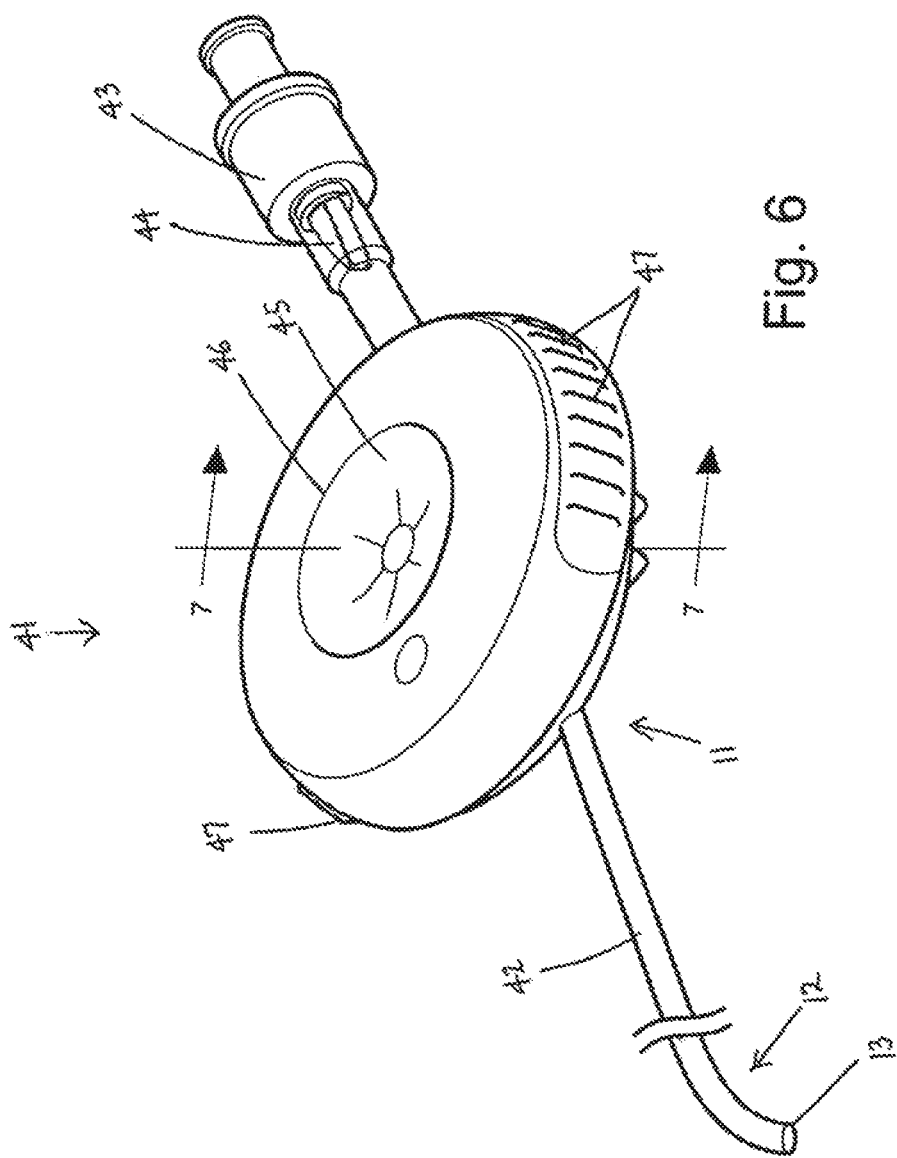

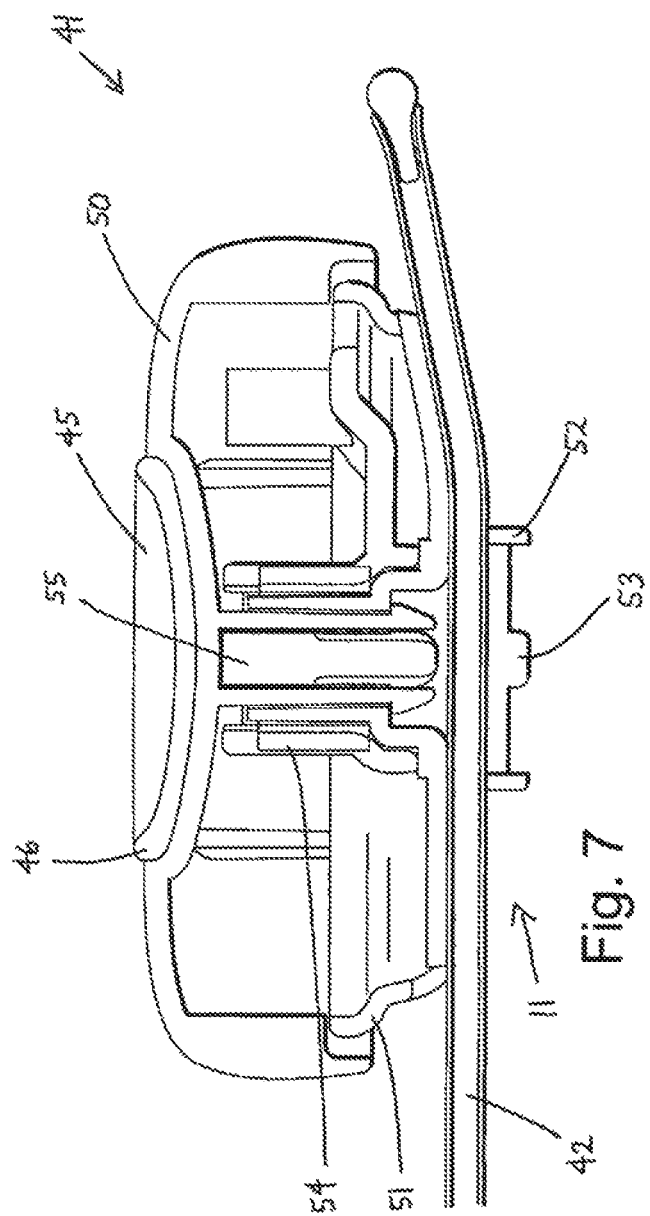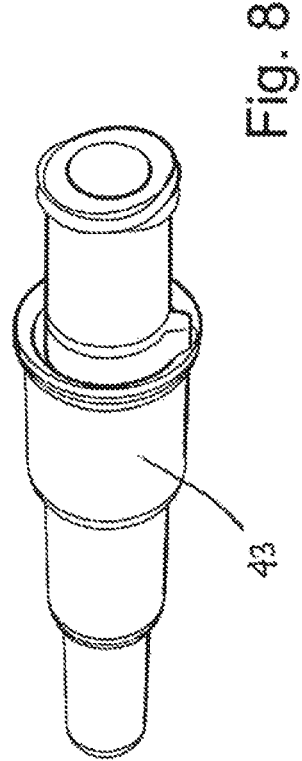
Fig. 7
Fig. 8

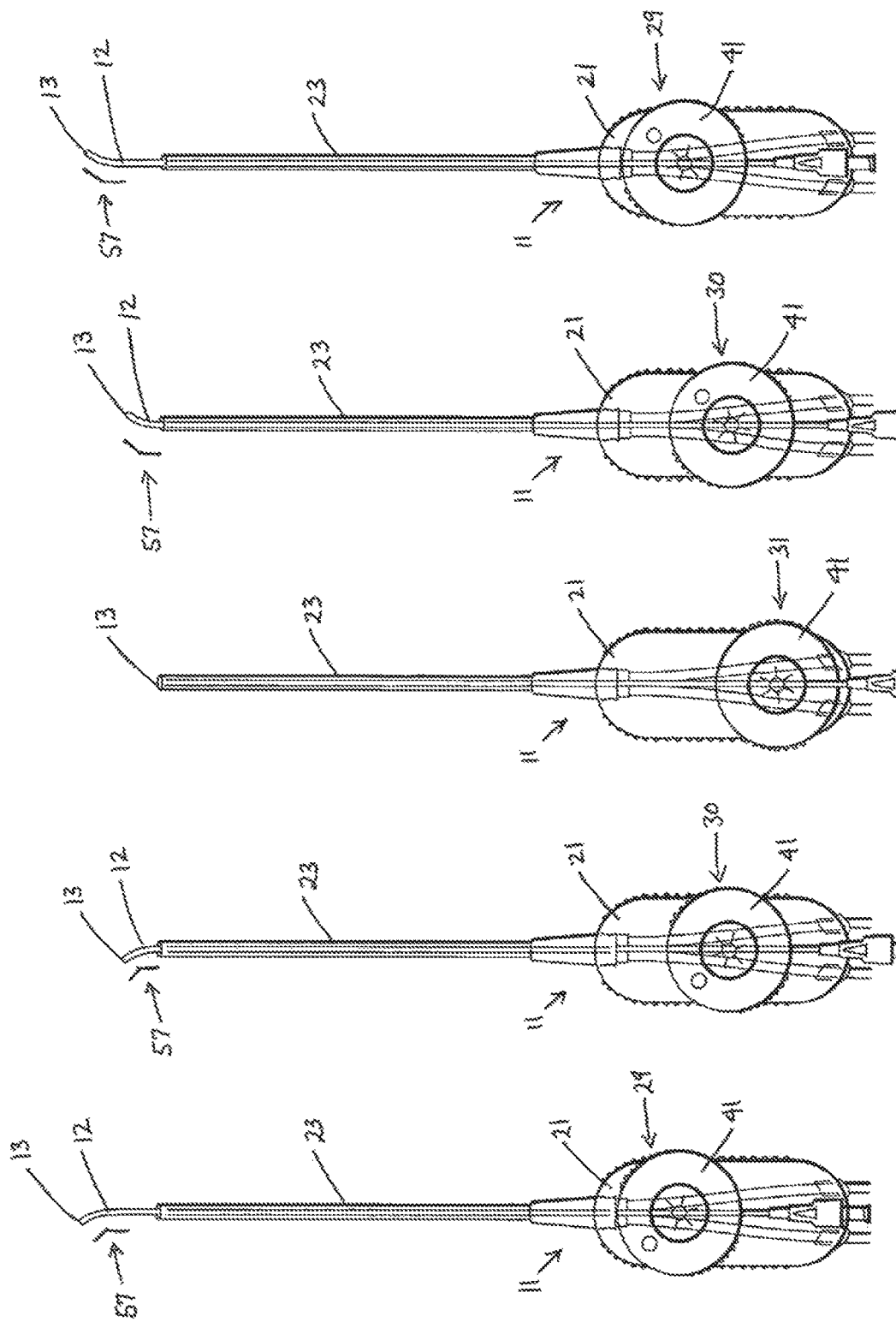

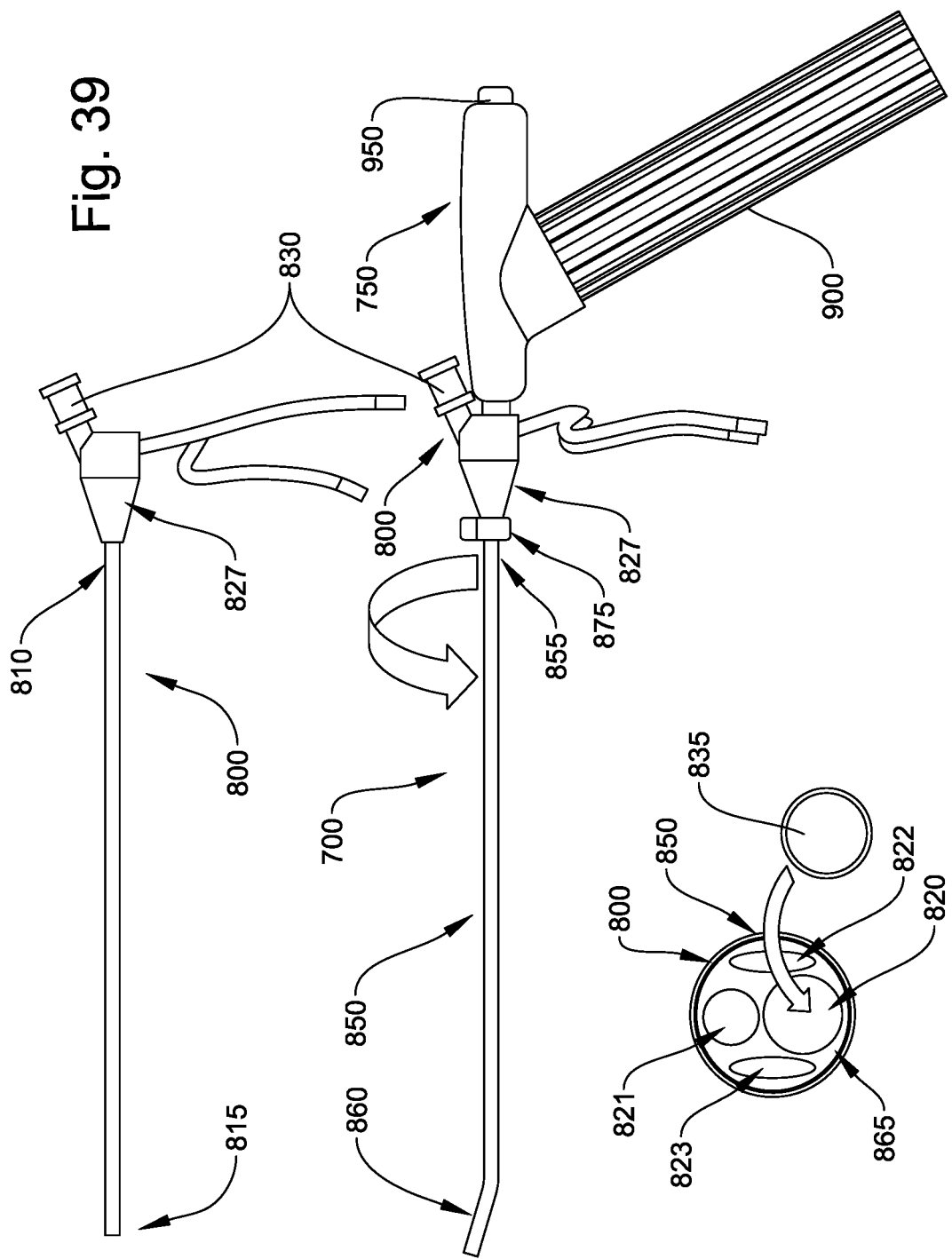

METHOD OF MAKING A SEALED LUMEN AND ASSOCIATED COMPUTING MODULE

CROSS-REFERENCE TO RELATED APPLICATIONS

This application is a continuation of U.S. patent application Ser. No. 15/286,519 filed on Oct. 5, 2016 and entitled "MEDICAL DEVICE INTRODUCTION AND IMAGING SYSTEM, AND ASSOCIATED METHOD", which claims priority to U.S. Provisional Patent Application No. 62/393,636 filed on Sep. 12, 2016 and entitled "MEDICAL DEVICE INTRODUCTION AND IMAGING SYSTEM, AND ASSOCIATED METHOD". U.S. patent application Ser. No. 15/286,519 also claims priority to U.S. patent application Ser. No. 15/072,077 filed on Mar. 16, 2016 and entitled "MEDICAL DEVICE INTRODUCTION AND IMAGING SYSTEM, AND ASSOCIATED METHOD", which claims priority to U.S. patent application Ser. No. 14/942,360 filed on Nov. 16, 2015 and entitled "MEDICAL DEVICE INTRODUCTION SYSTEM AND ASSOCIATED IMAGING SYSTEM AND METHOD", which claims priority to U.S. patent application Ser. No. 14/157,307 filed on Jan. 16, 2014 and entitled "MEDICAL DEVICE INTRODUCTION SYSTEMS AND METHODS", which claims priority to U.S. Provisional Patent Application No. 61/753,413 filed on Jan. 16, 2013 and entitled "MEDICAL DEVICE INTRODUCTION SYSTEMS AND METHODS".

BACKGROUND

Field of the Disclosure

The present disclosure relates to a method of making a sealed lumen and associated computing module for use with the sealed lumen.

Description of Related Art

In recent years, medical procedures have advanced to stages where less and less invasive, or minimally invasive, surgeries, diagnostic procedures, exploratory procedures, or other medical procedures have been desired and demanded by patients, physicians, and payers. To accomplish these desires and demands, various medical devices and instrumentation have been developed, such as cannulas or microcannulas, various catheter devices, micro-surgical instrumentation and implants, medical introducers, imaging devices such as fiberoptic scopes, and other related endoscopic devices.

In situations in which minimally invasive procedures are used, space within an interior body region, for example, an organ, opening, cavity, passageway, or vessel, can become more and more constrained. As a result, operating within small spaces with a plurality of medical devices, such as scopes, dilating and cutting instruments, fluids, catheters, implants, and the like, can become difficult to manage. When performing a procedure with a plurality of medical devices, the positioning, controlling, manipulating, and handling of the various medical devices during the procedure can limit a physician's ability to perform as well as capable. That is, the design and construction of a medical device can limit a physician's ability to view a target site, maneuver within a space, transition between procedures, and/or perform additional procedures. Managing the use of multiple devices in a procedure can pose even greater difficulty to a single physician who desires to perform a procedure, often without assistance or with limited assistance, in an office or outpatient setting so as to avoid the time and expense of hospital utilization for such procedures.

Conventional medical devices having optical capabilities, such as conventional endoscopes, can have other disadvantages. The optical capabilities can be limited due to various factors, including, for example, the anatomical structures about which the scopes are maneuvered, and the movement and/or control together of both the imaging device and a delivery device and the resulting loss in orientation in an interior body region. For example, optical capabilities with conventional endoscopes typically used in hysteroscopy procedures are often limited in such ways, making it difficult for the physician to know whether what is being viewed is up or down. Such conventional endoscopes and associated delivery devices are often complex and require extended learning to operate effectively. In addition, many conventional endoscopes and delivery devices are reusable and can be very expensive to purchase and to re-sterilize after each use. As a result, physicians often elect not to perform diagnostic and/or therapeutic procedures in a medical office or outpatient setting that could otherwise be performed to the patient's advantage in those settings.

During use in medical procedures, introducer instruments, sheaths, endoscopes, and working catheters and cannula can be exposed to various bacteria, viruses, and other microorganisms, and to potentially disease carrying media. These microorganisms can be trapped in such devices, particularly in lumens, and transferred to subsequent patients or users.

Sterilization methods can be employed on such devices that are reusable in an attempt to disinfect and eliminate microorganisms for subsequent use of the devices. However, some surgical devices contain very small and/or narrow working channels or lumens for performing intricate medical procedures. These small and/or narrow working channels can be difficult to clean and sterilize. If not effectively eliminated, these materials may be transferred to, and potentially cause harmful infections to, other patients or medical personnel through subsequent use of the devices.

In addition to the problems of potential disease transmission and lack of disposability, conventional reusable medical introducer, endoscopes, and the like are subjected to repeated use over prolonged periods. The precision of manipulation and movement in endoscopes and steerable medical devices is often essential for conducting complicated diagnostic and therapeutic medical procedures generally performed with such devices. Some reusable devices containing steering mechanisms often require precision calibration. Further, these devices are regularly subjected to sterilization with heat or chemicals. To accomplish these objectives, conventional reusable devices are often made of stainless steel or other durable materials that are costly. In addition, despite being designed for repeated use, such conventional intricate reusable devices, in particular, such devices that incorporate visualization components, often require regular replacement, further adding to the cost of such devices.

SUMMARY

In some embodiments, the presently disclosed subject matter is directed to an assembly comprising a lumen comprising an open end, a closed end, and a cavity. The assembly further comprises a guiding member comprising a first end, a second end, and a contact element comprising a marker positioned at the second end, wherein the marker is configured to indicate the presence or absence of biological contamination. In some embodiments, the lumen is a working lumen and the cavity is sized and shaped to house a medical device, such as an endoscope. In some embodiments, the guiding member is conically-shaped, with the diameter of the first end less than the diameter of the second end.

In some embodiments, the presently disclosed subject matter is directed to a method of detecting the presence or absence of biological contamination on a medical device. Particularly, the method comprises providing a medical device and providing the disclosed assembly. The medical device is positioned within the cavity of the lumen. At a desired time, the medical device is removed from the cavity of the lumen such that the device contacts the contact element and is exposed to marker. Marker is then detected to determine the presence or absence of biological contamination on the medical device. In some embodiments, the biological contamination comprises bacterial contamination, viral contamination, or combinations thereof. In some embodiments, the detecting comprises exposing the medical device to fluorescence detection, such that if no contamination is present, the marker will not fluoresce and if contamination is present the device will fluoresce.

BRIEF DESCRIPTION OF THE DRAWINGS

Figure 1:
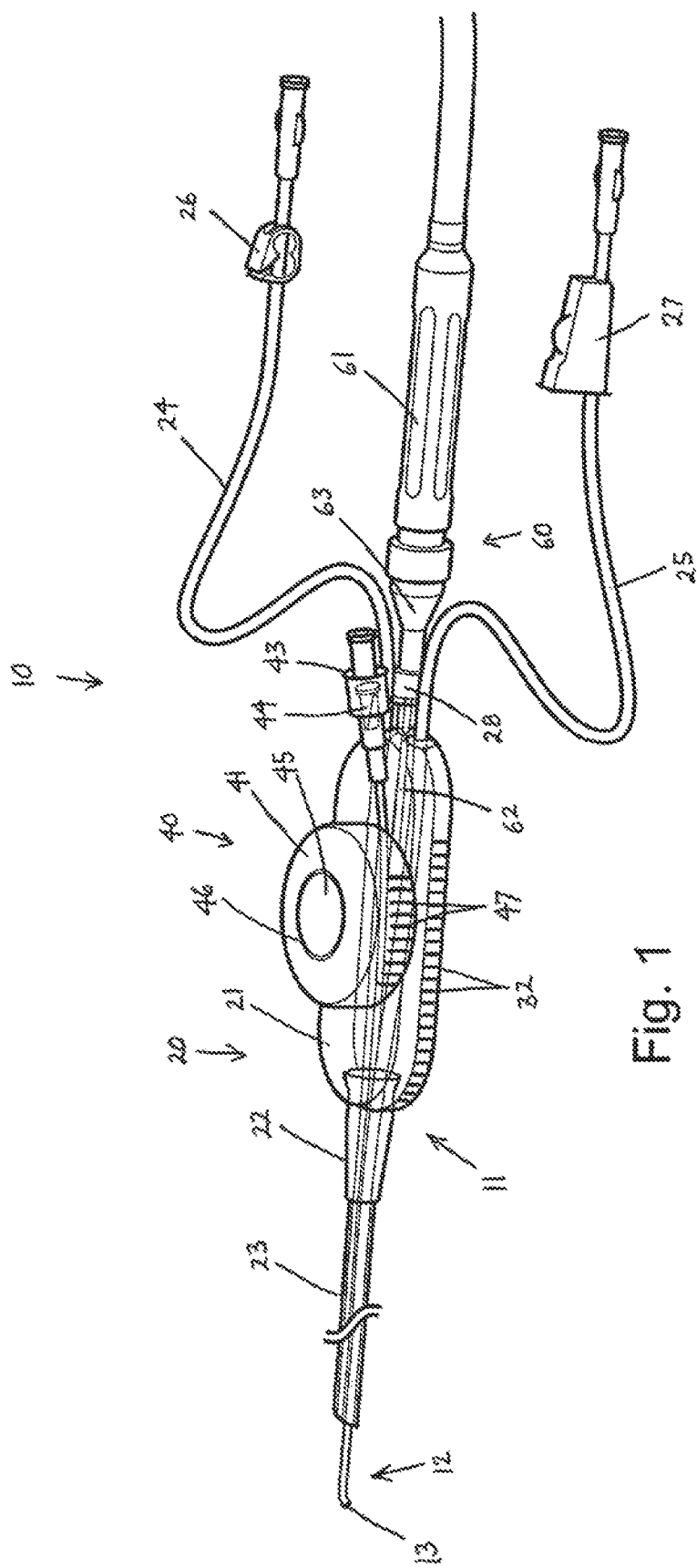
Figure 2:
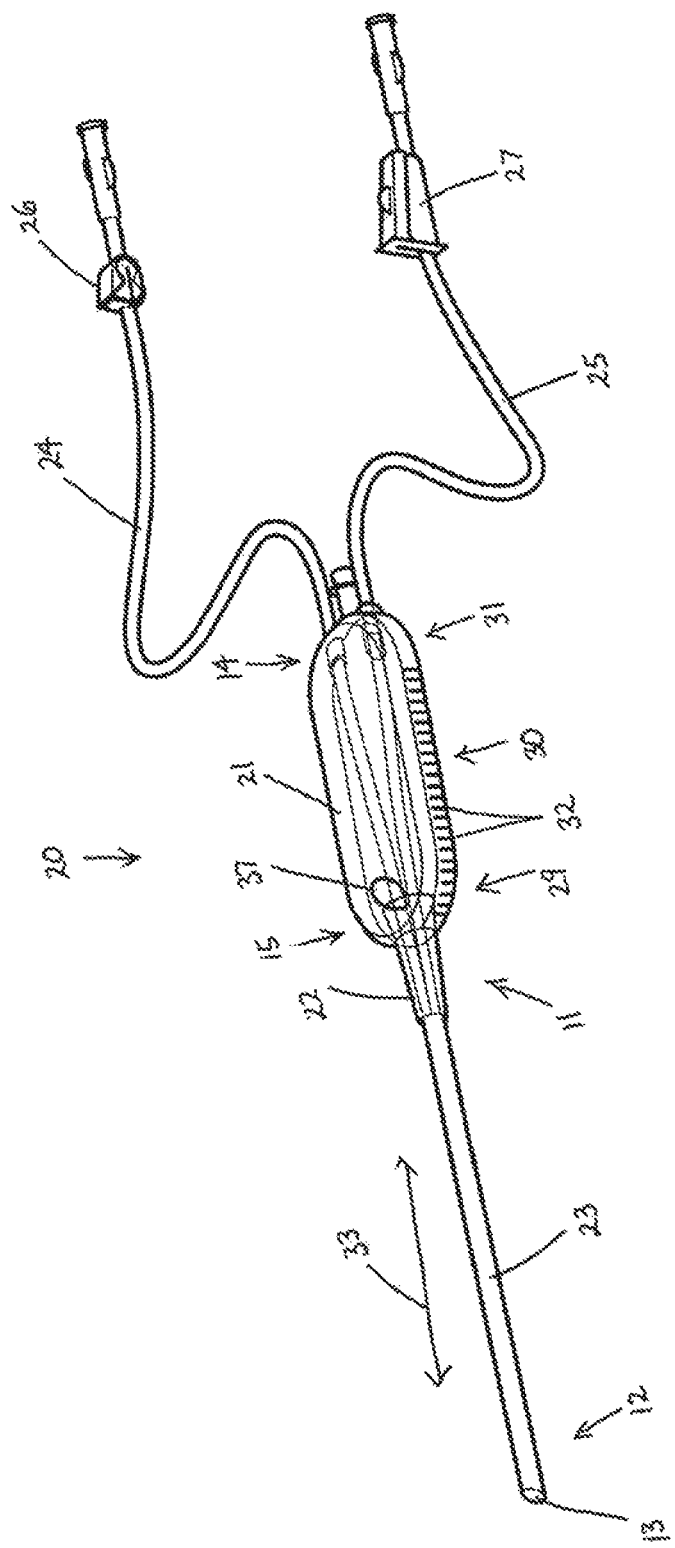
Figure 3:
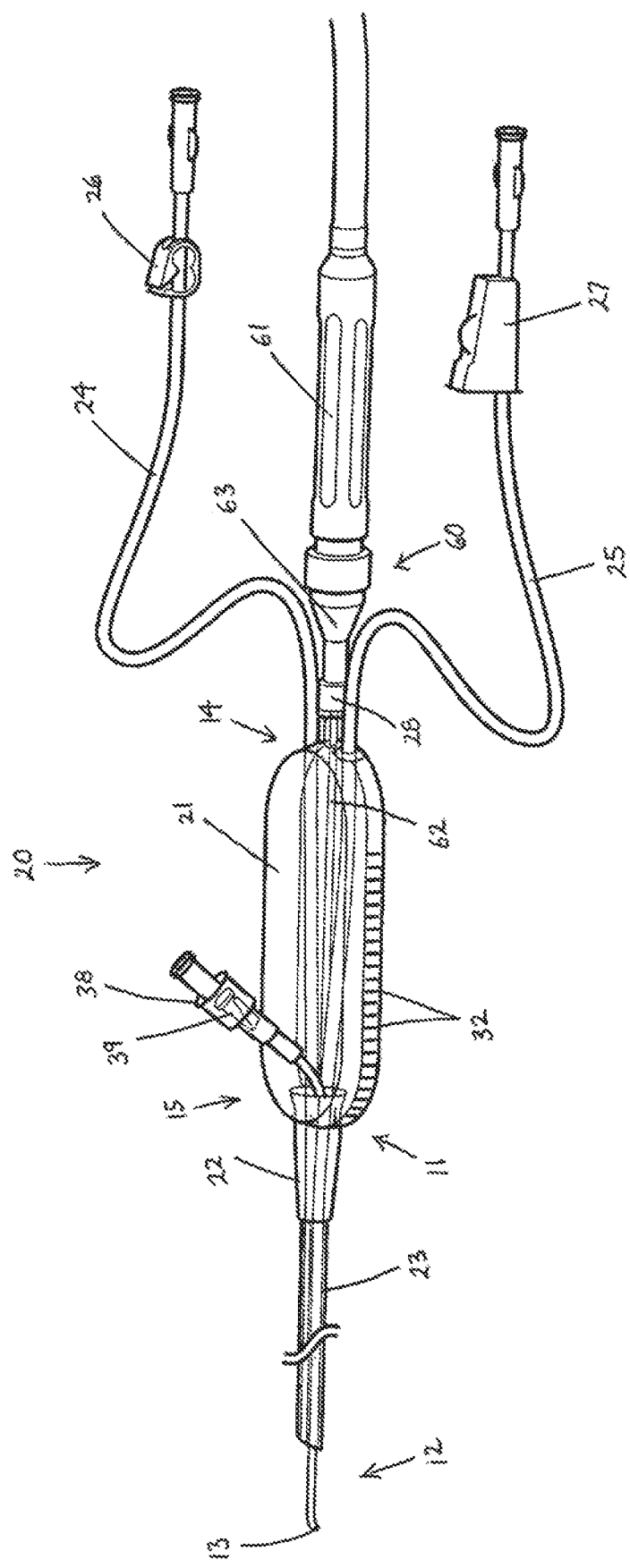
Figure 10A:
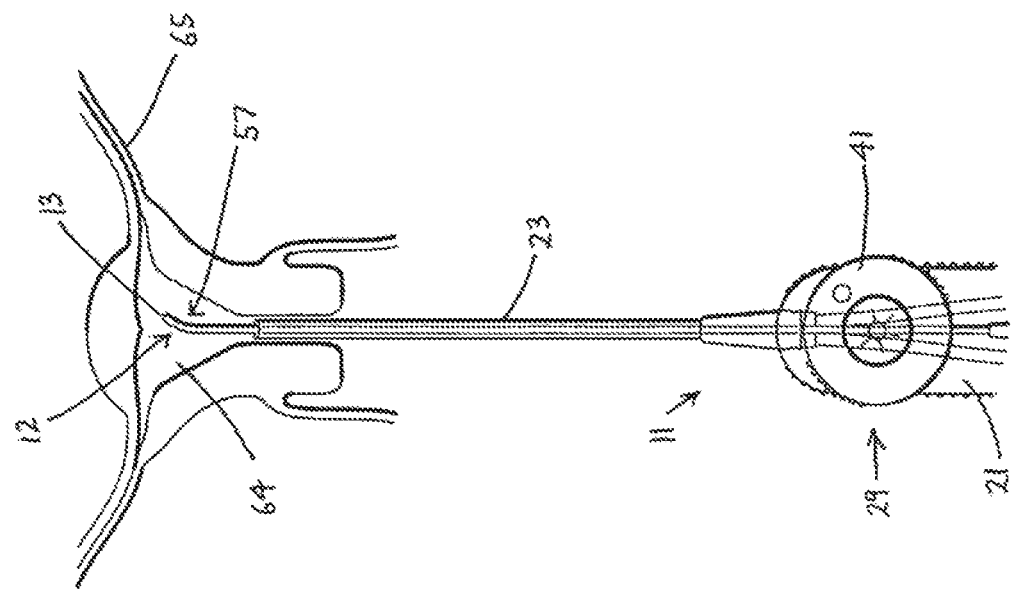
Figure 10B:
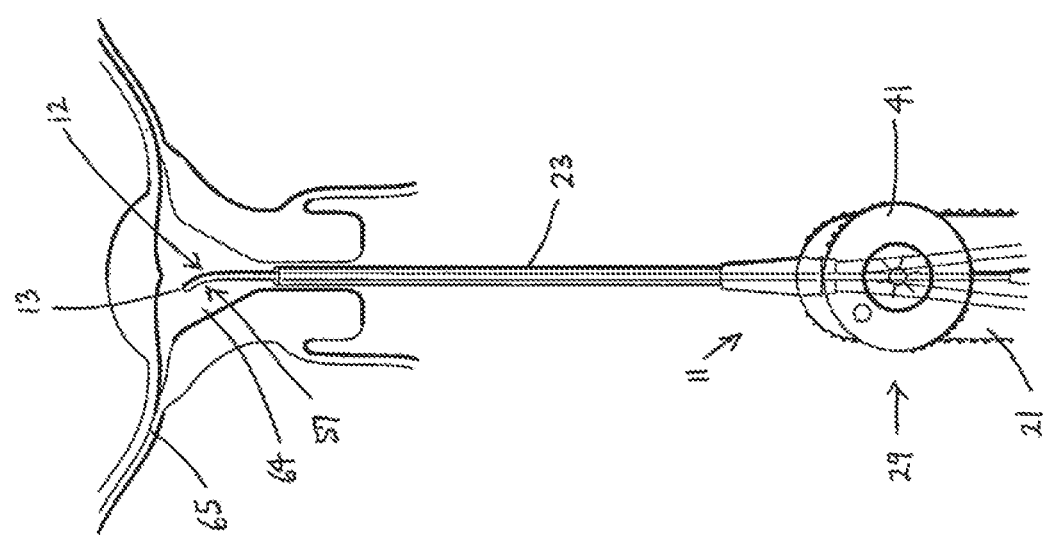
Figure 11:
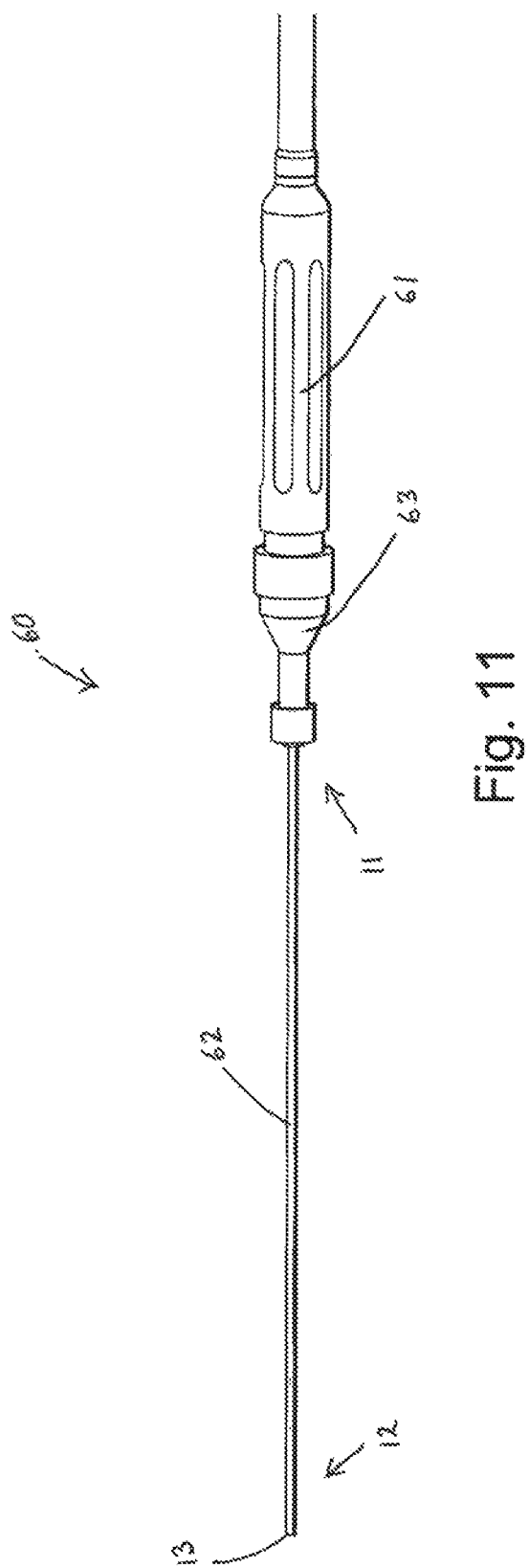
Figure 14:
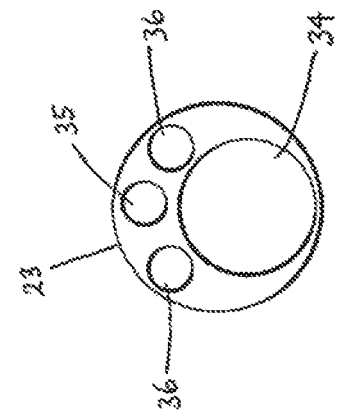
Figure 13:
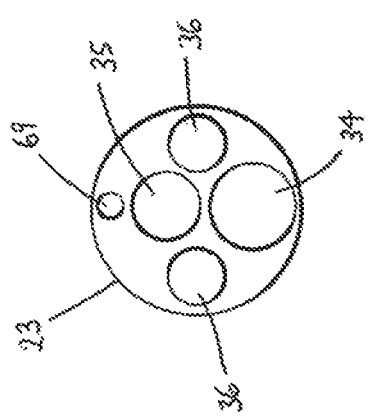
Figure 12:
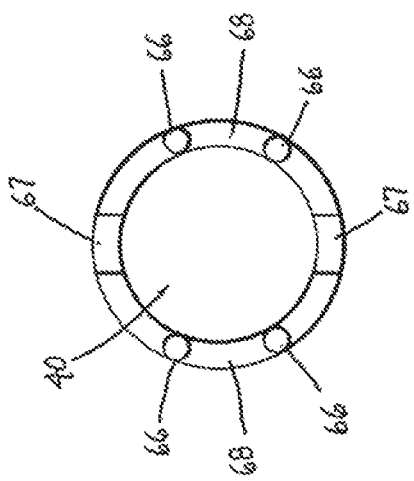
Figure 15:
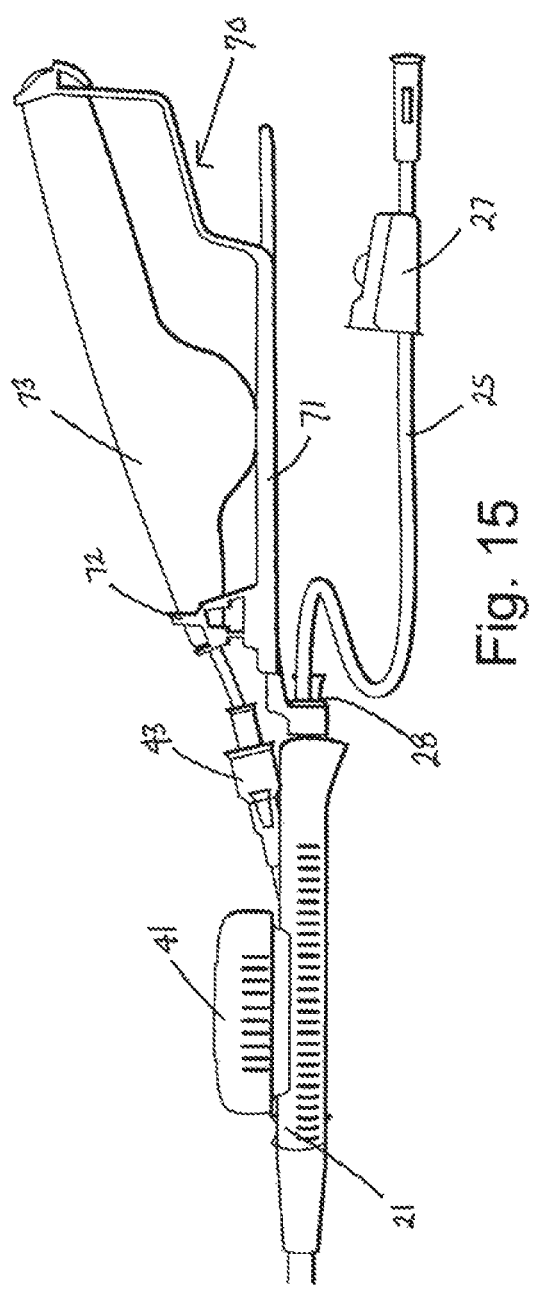
Figures 16A, 16B:
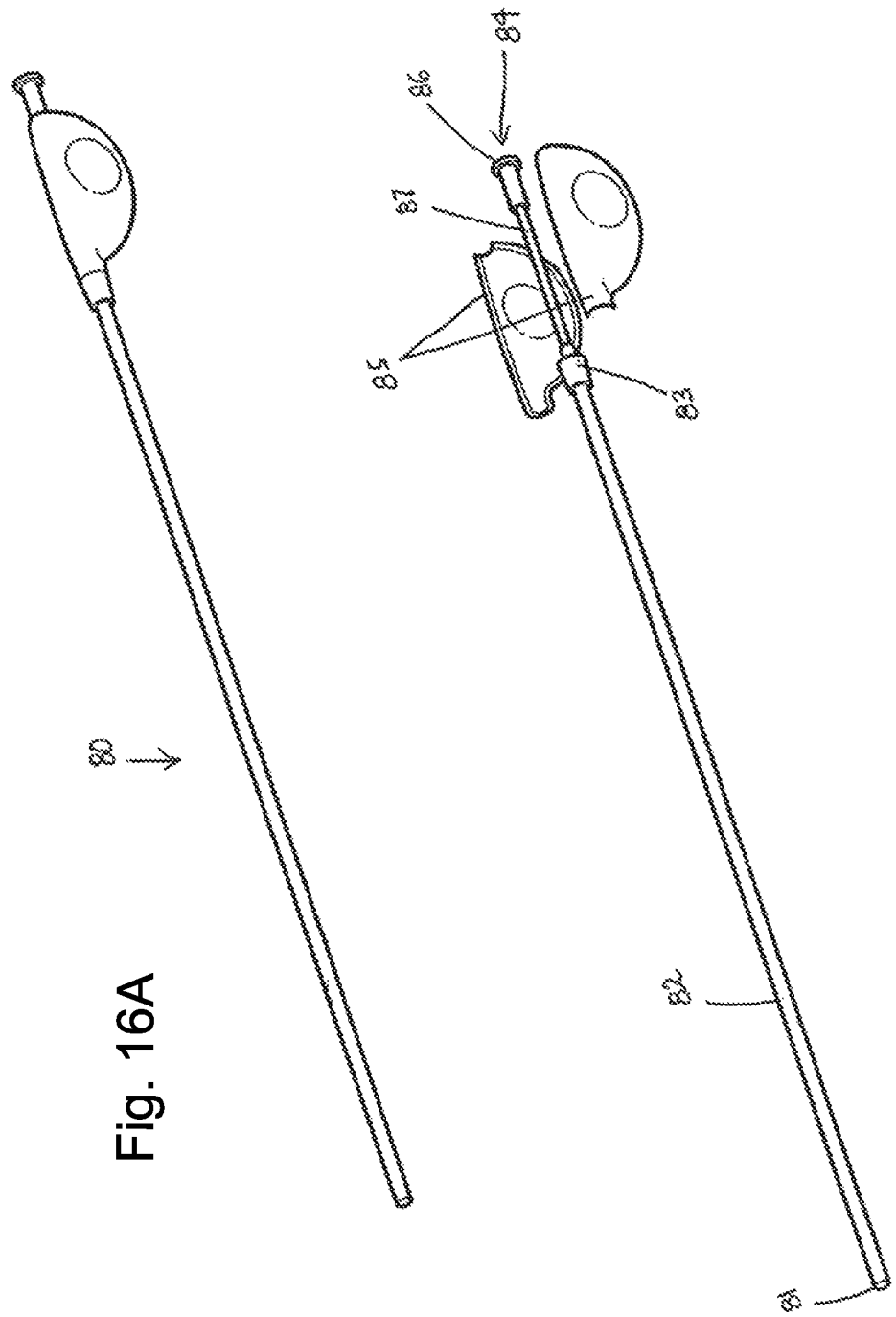
Figures 17A, 17B:
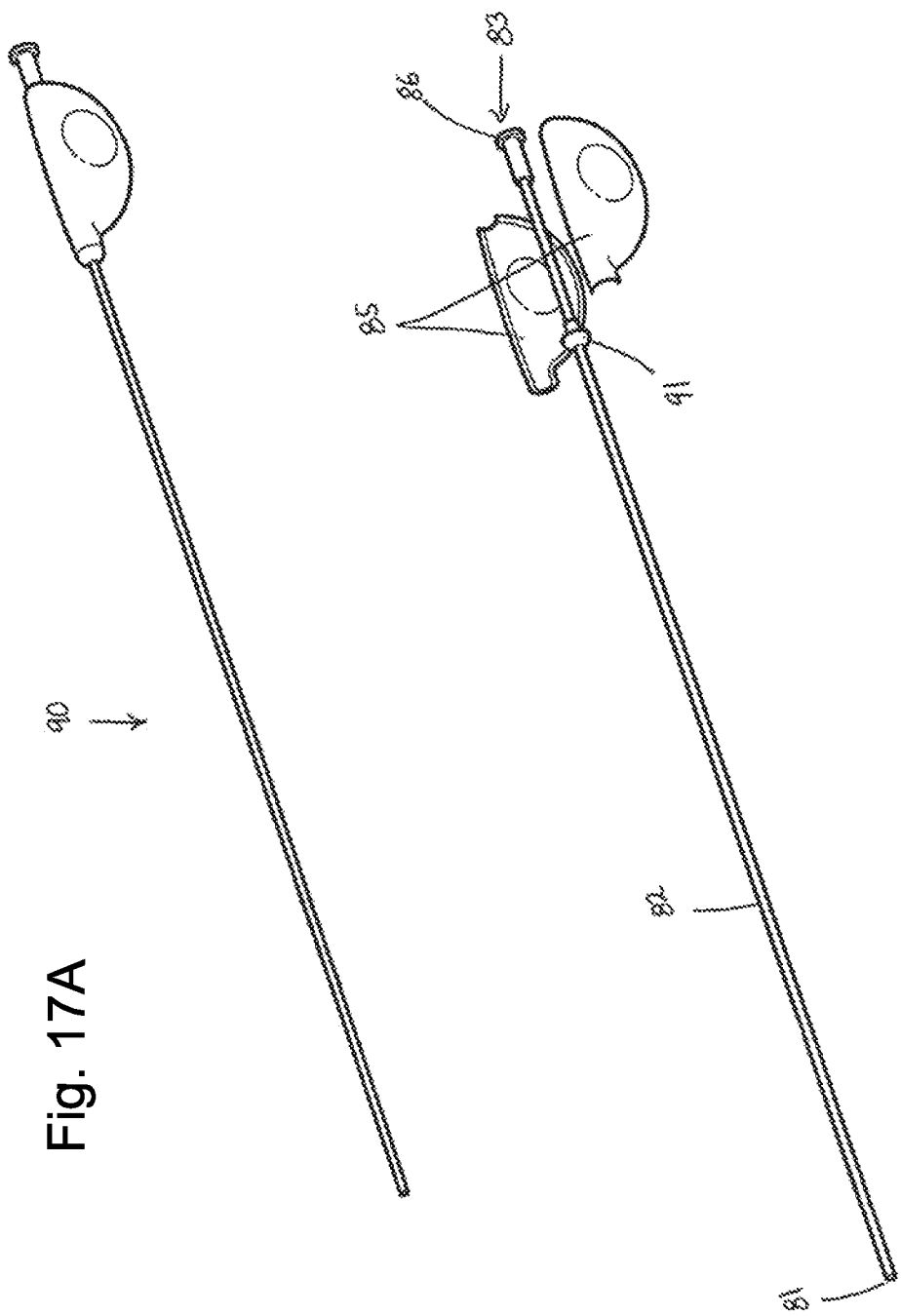
Figures 18A, 18B:
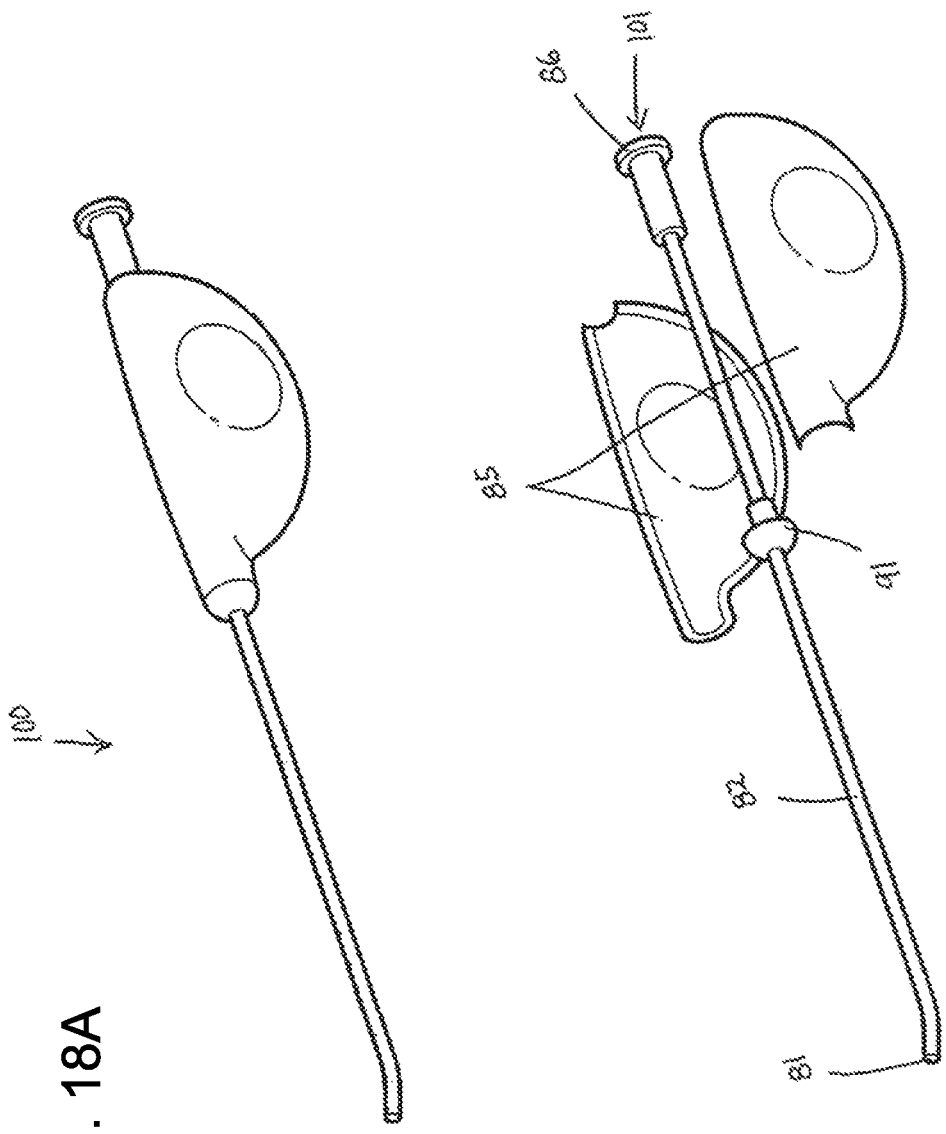
Figure 19:
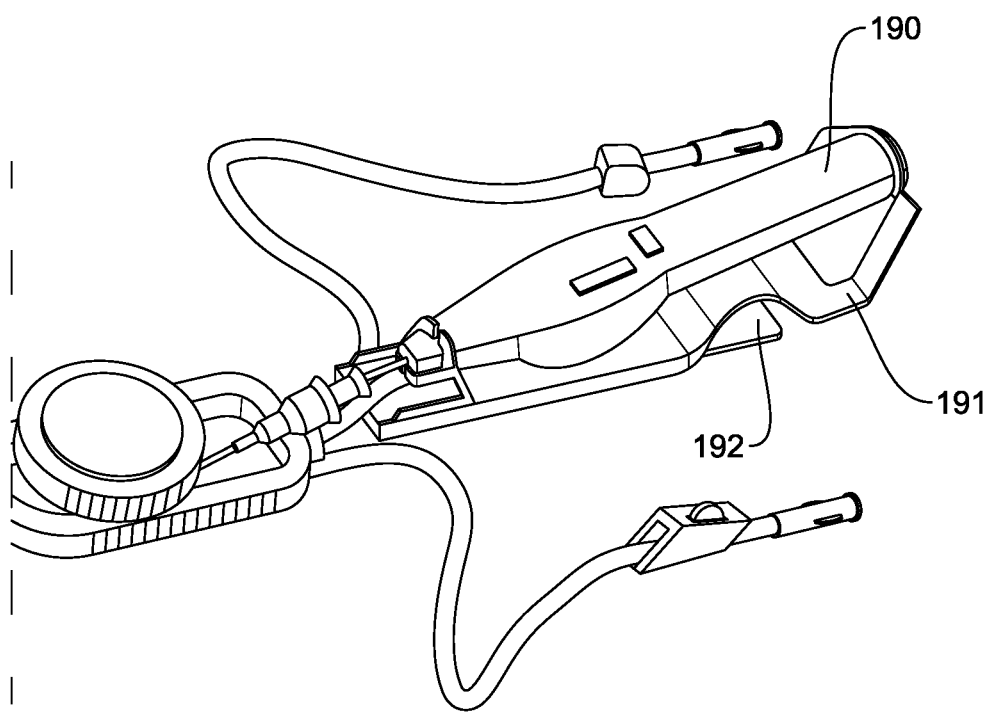
Figure 20:
Figure 21:
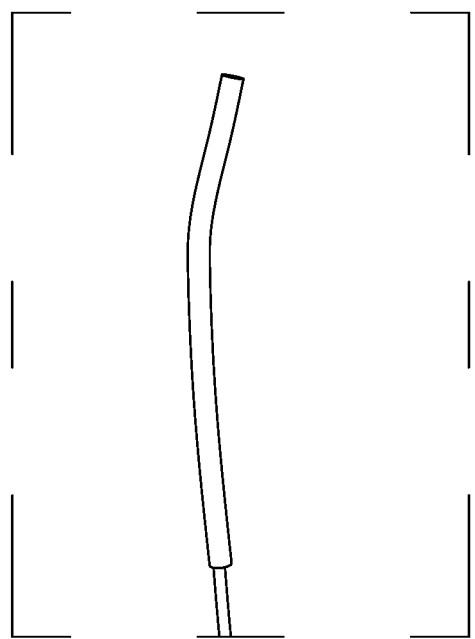
Figure 22:
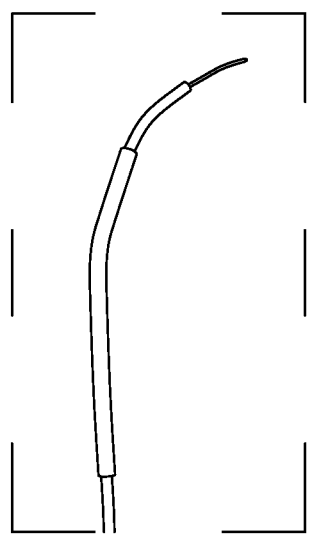
Figure 23:
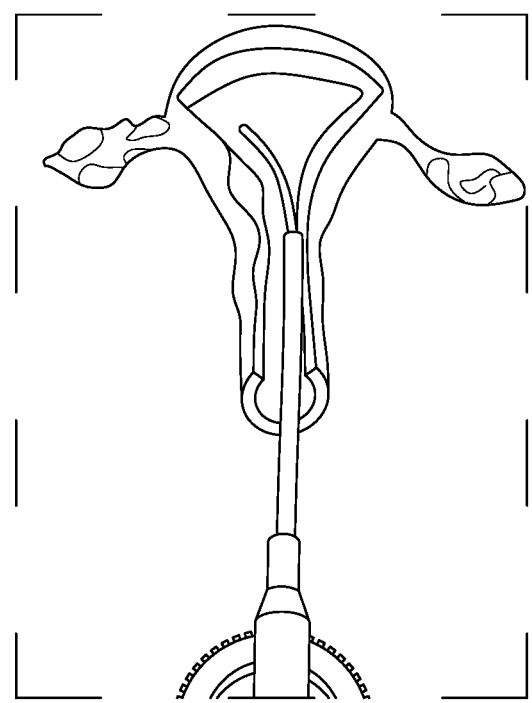
Figure 24:
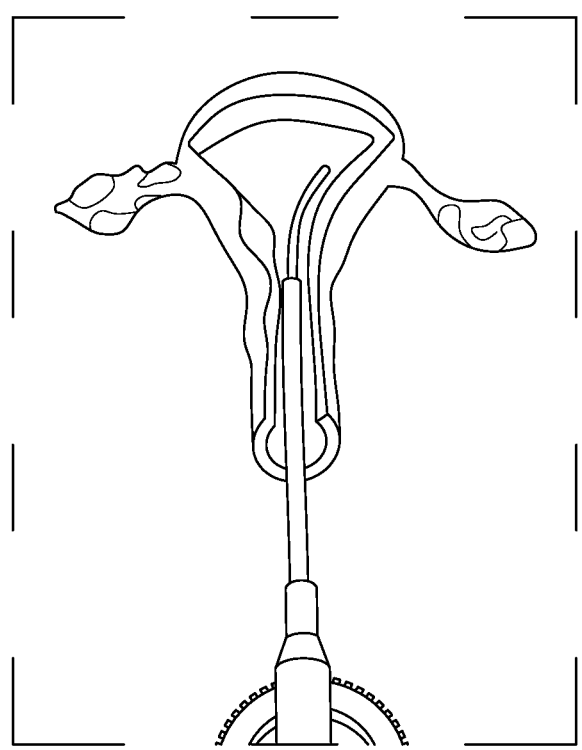
Figure 25:
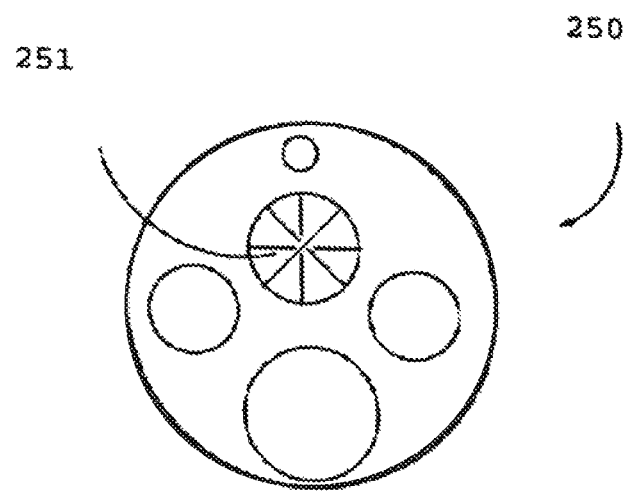
Figure 26:
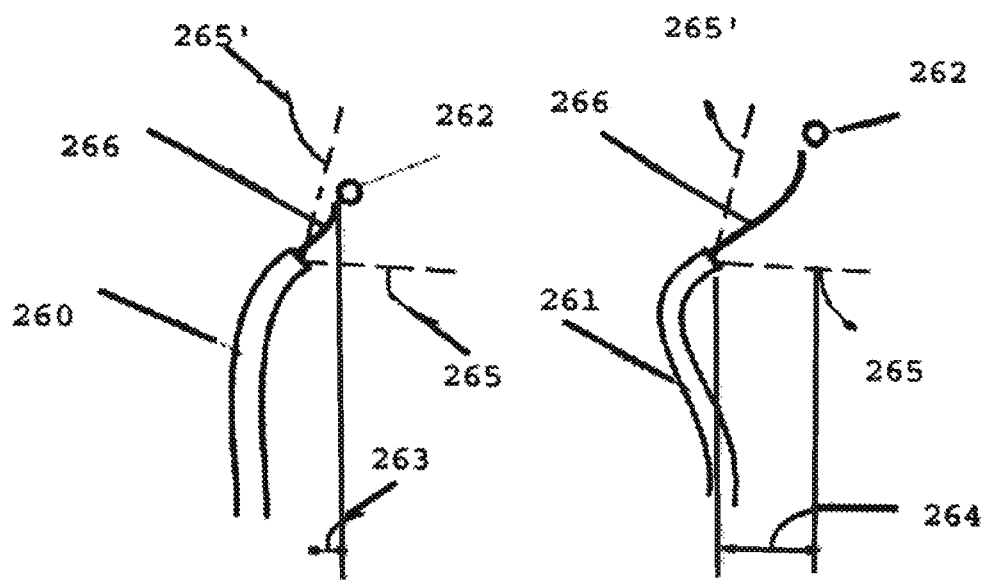
Figure 27:
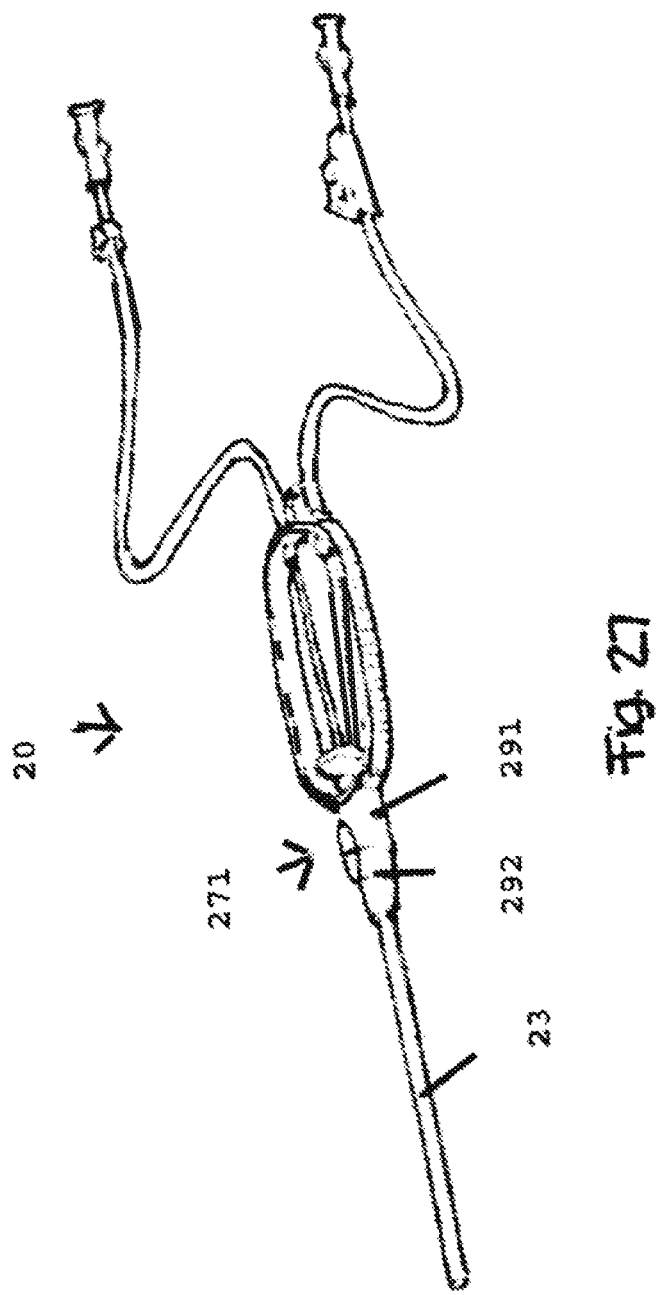
Figure 28:
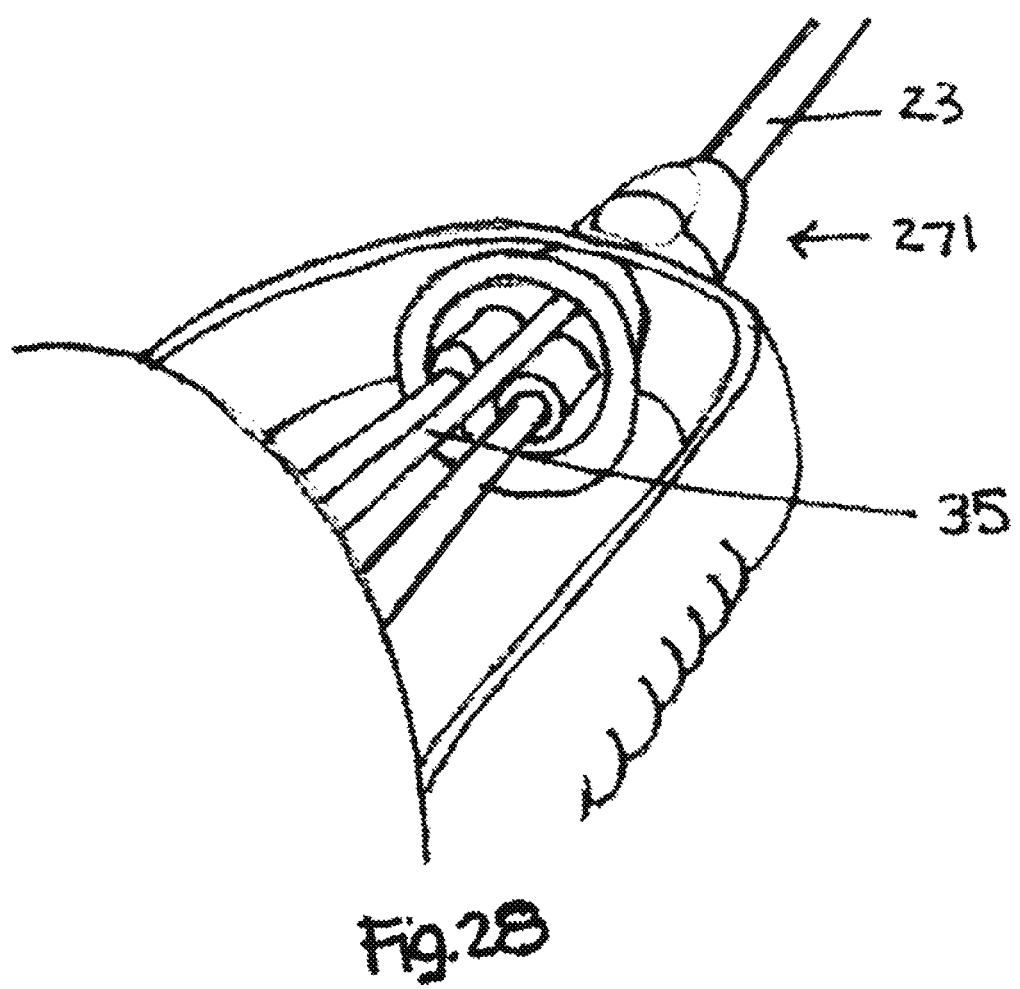
Figure 29:
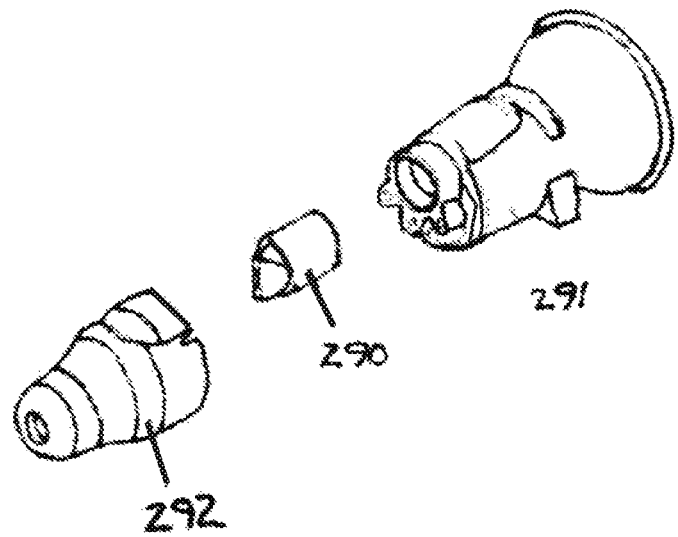
Figure 30:
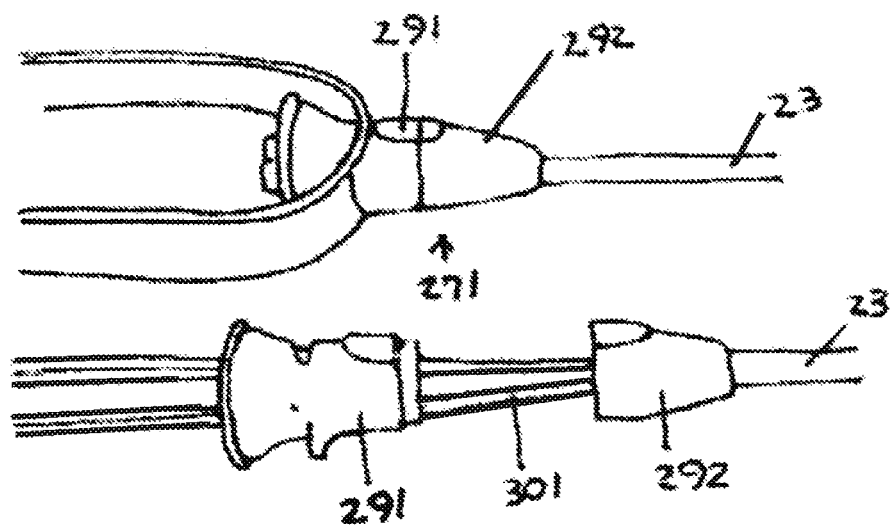
Figure 31:
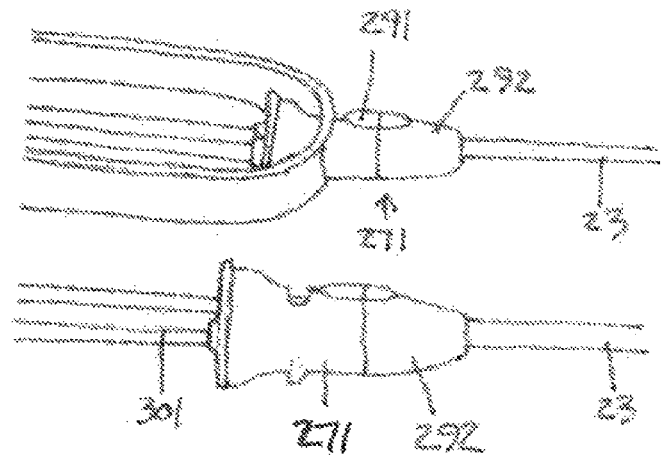
Figure 32:
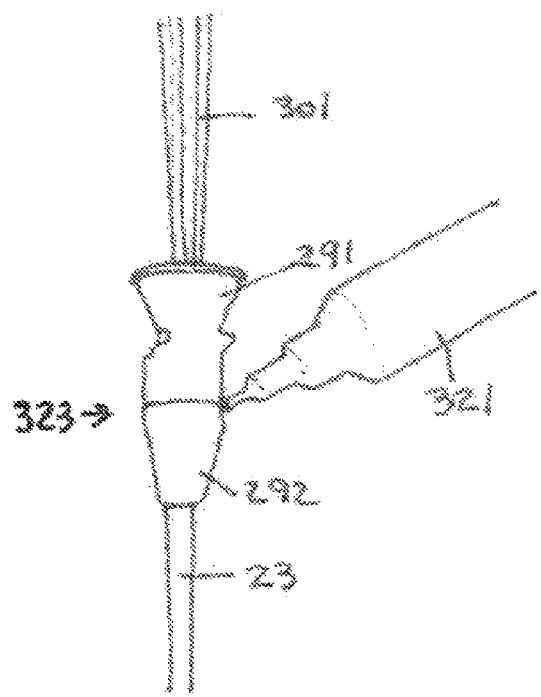
Figure 33:
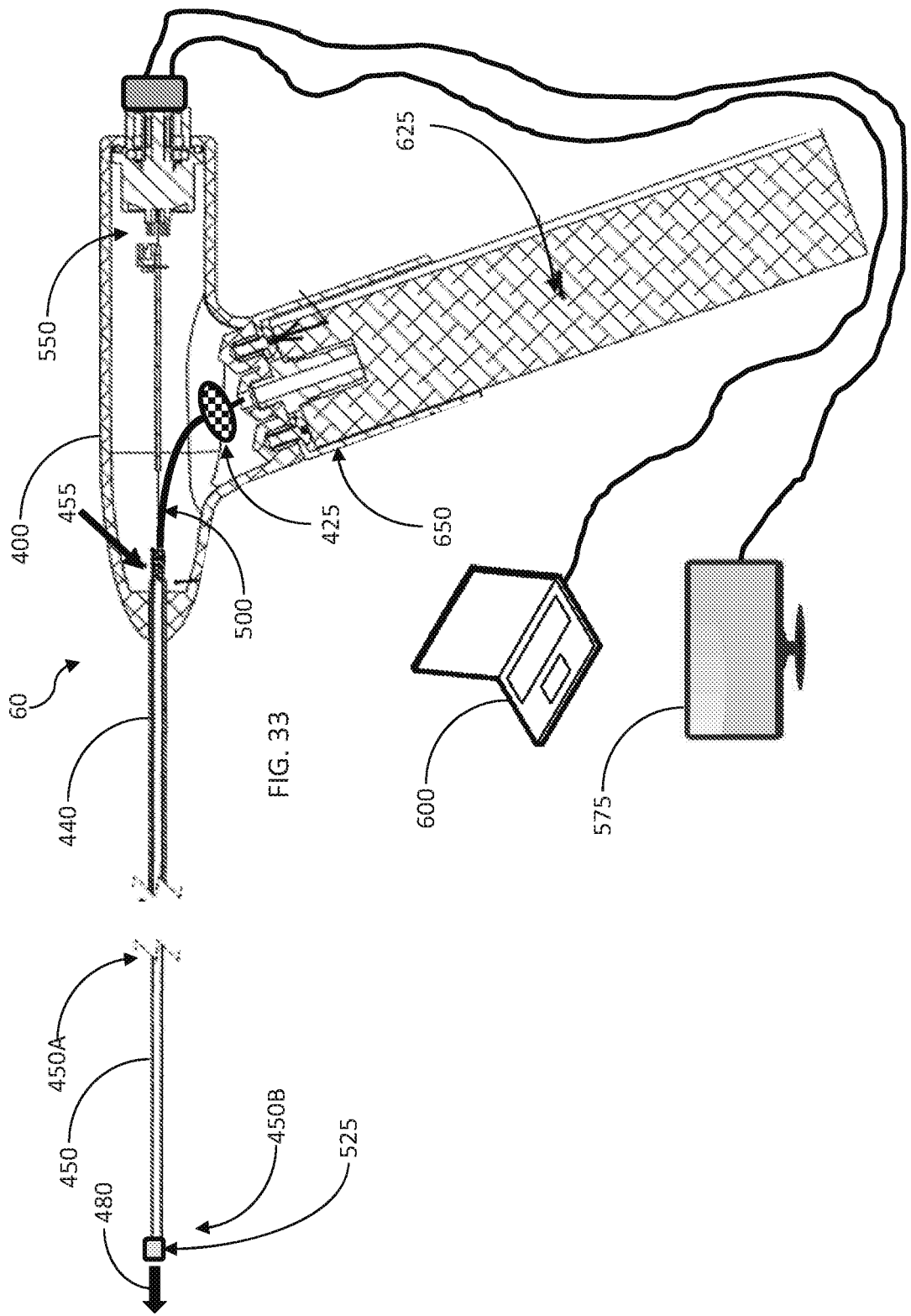
Figure 34:
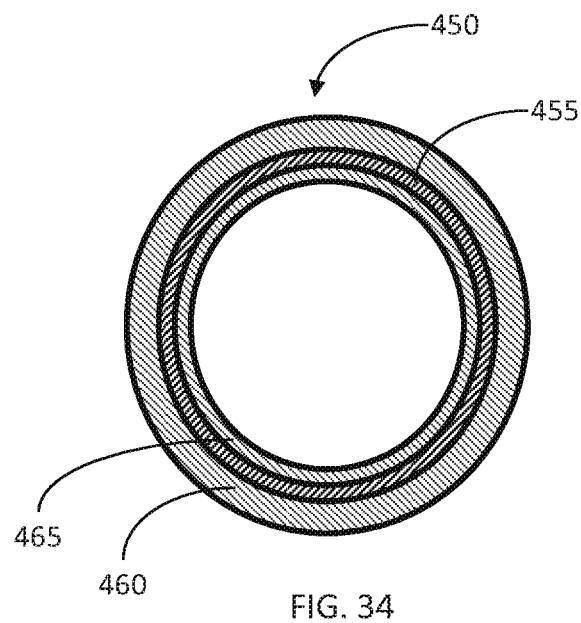
Figure 35:
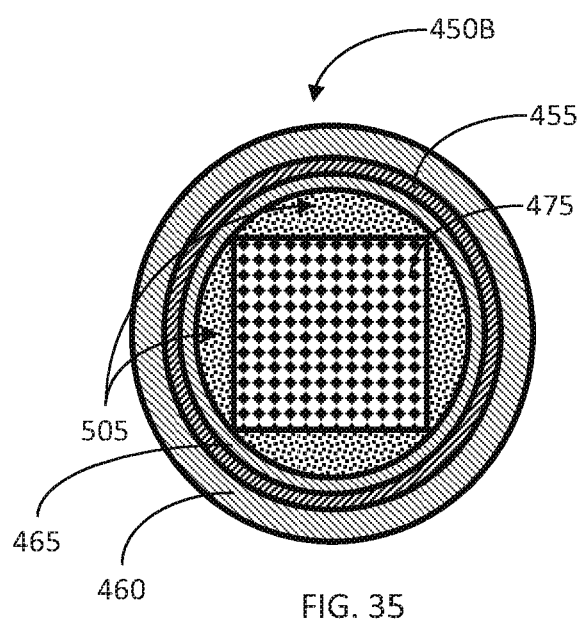
Figure 36:
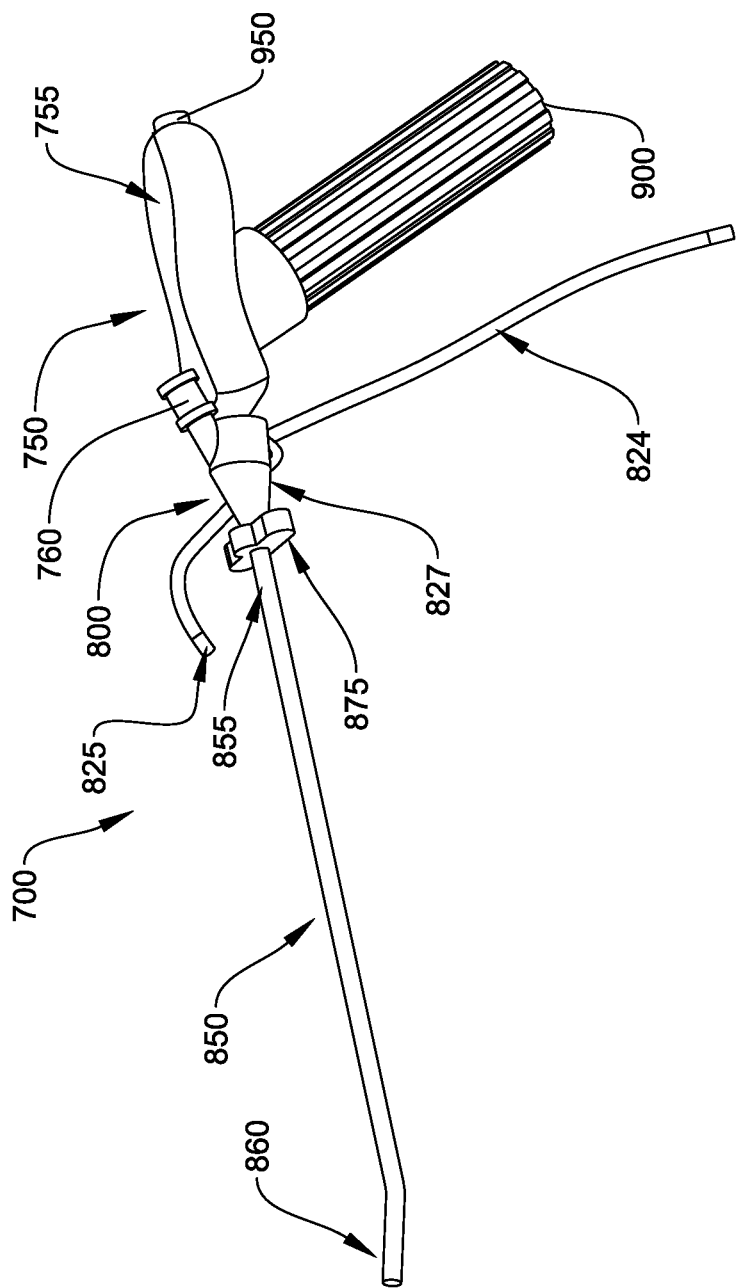
Figure 37:
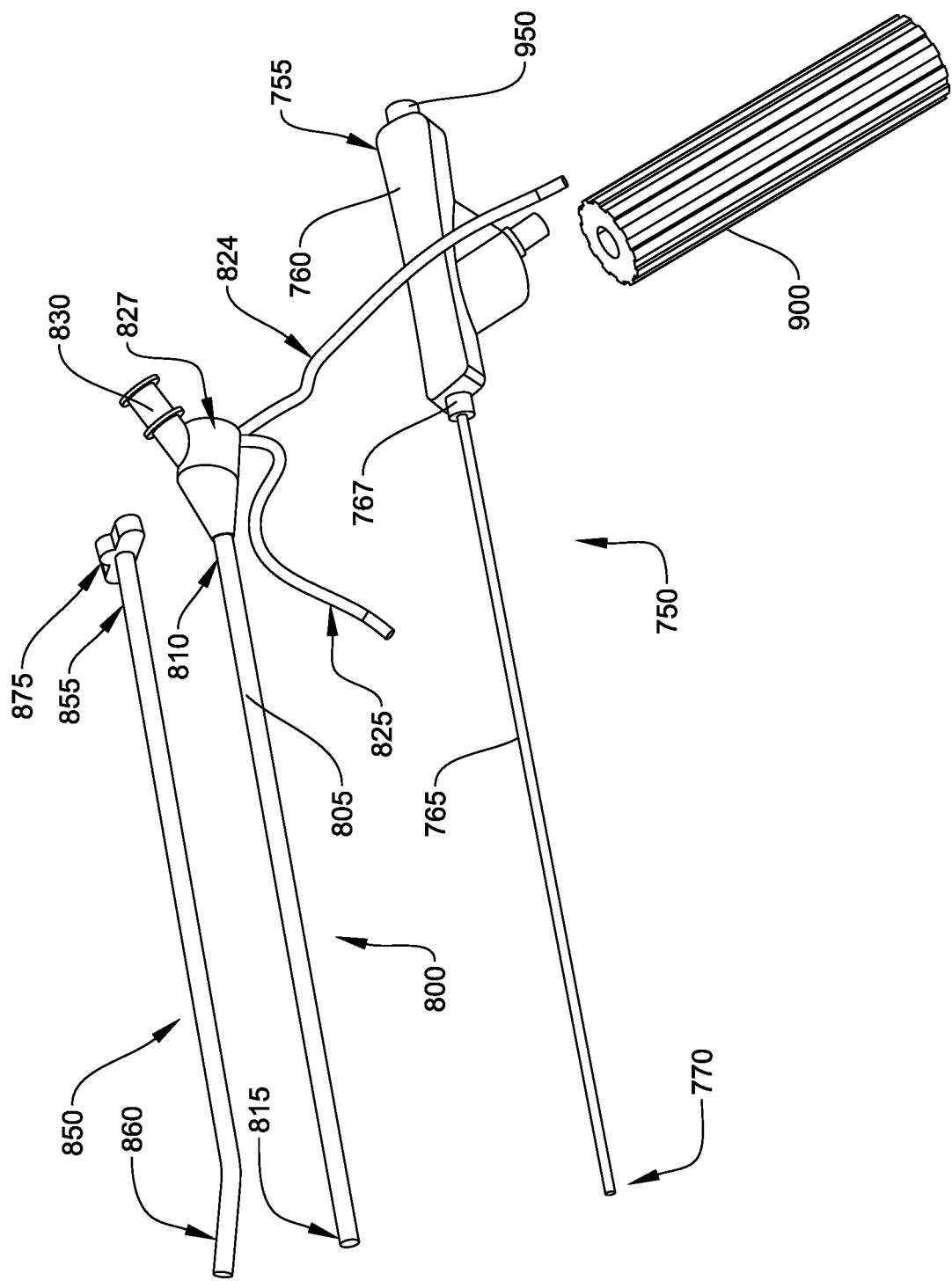
Figure 38:
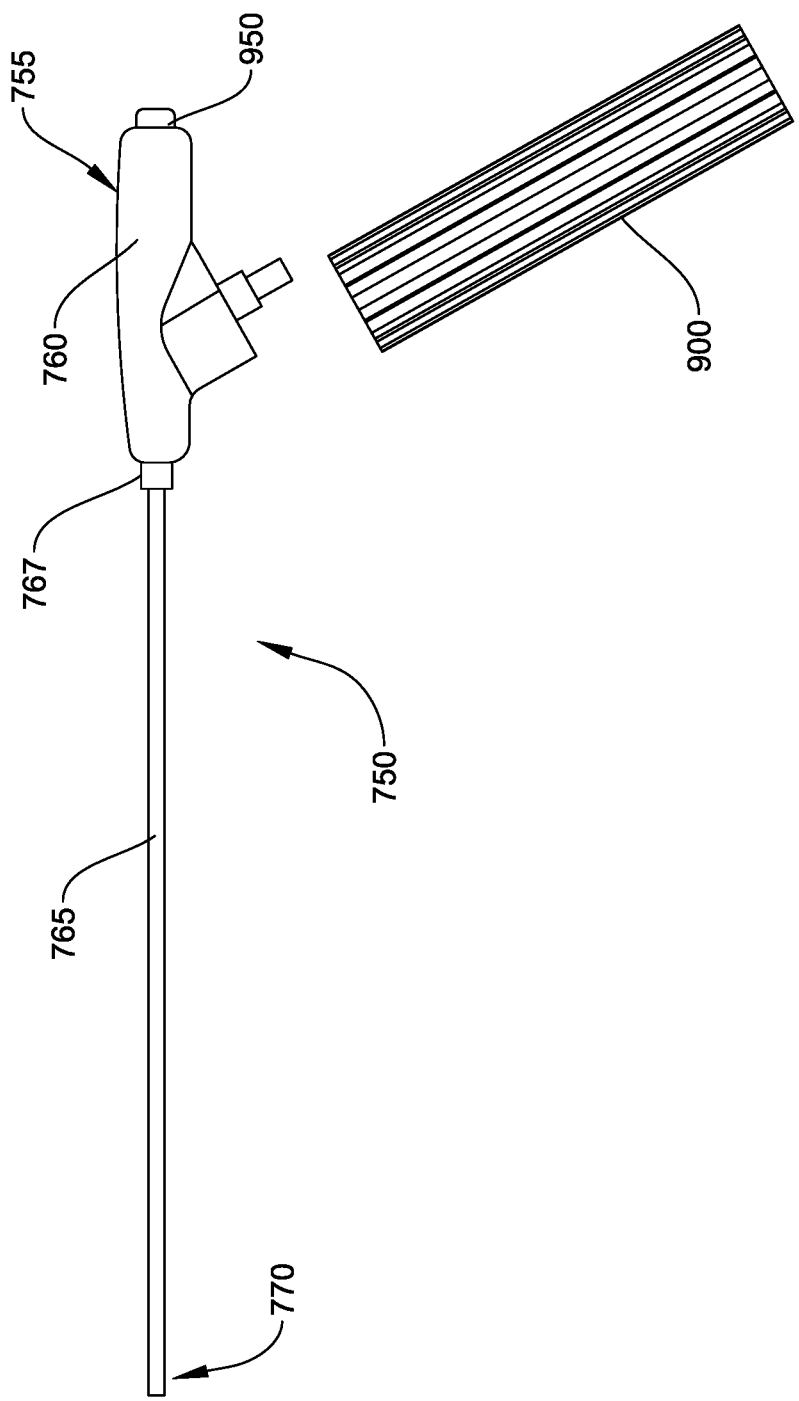
Figure 41:
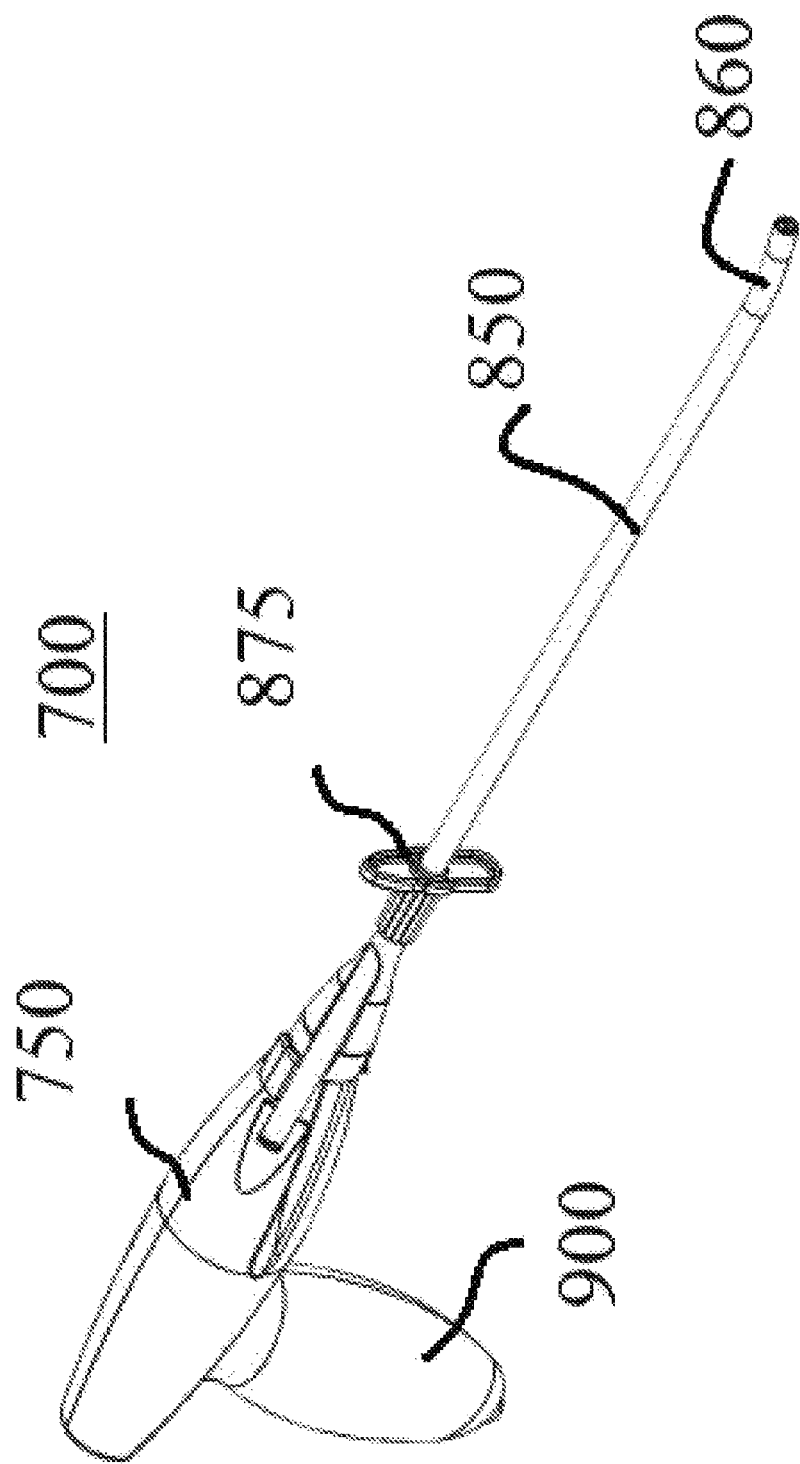
Figure 42:
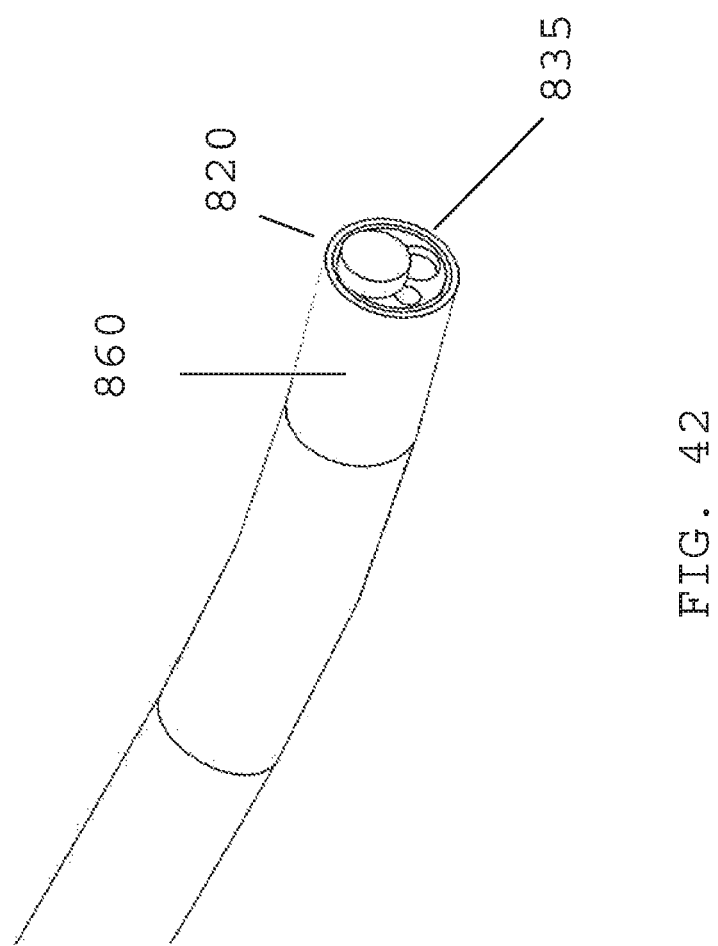
Figure 43:
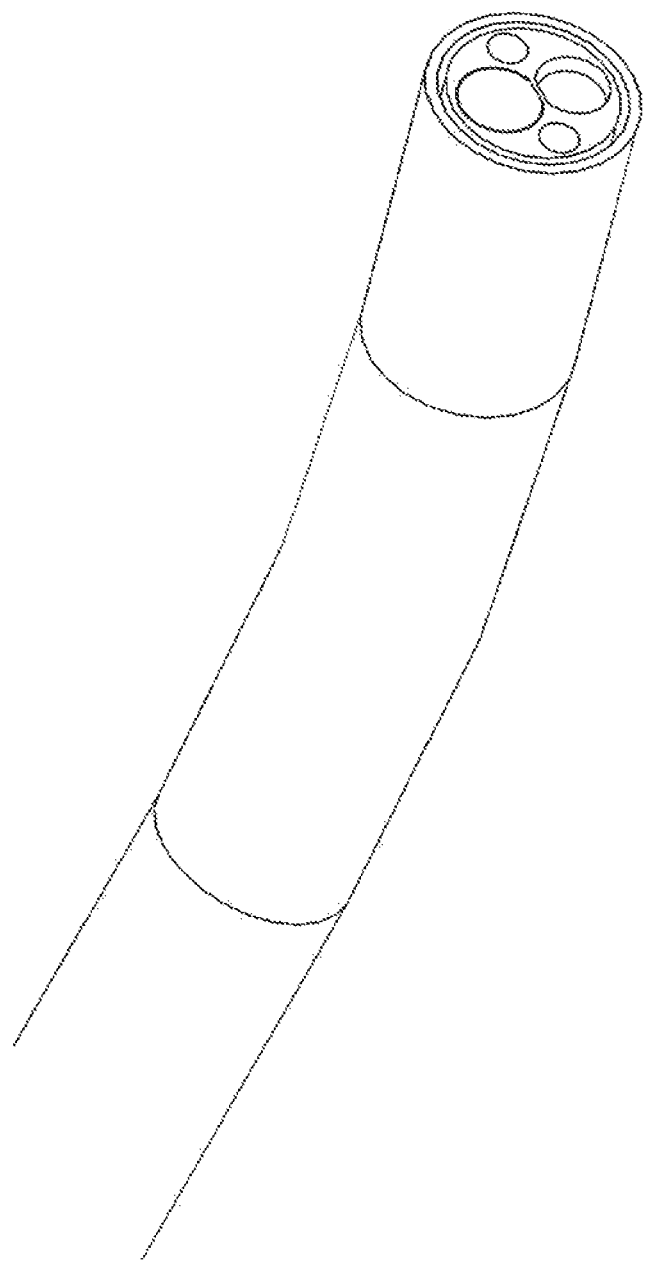
Figure 44:
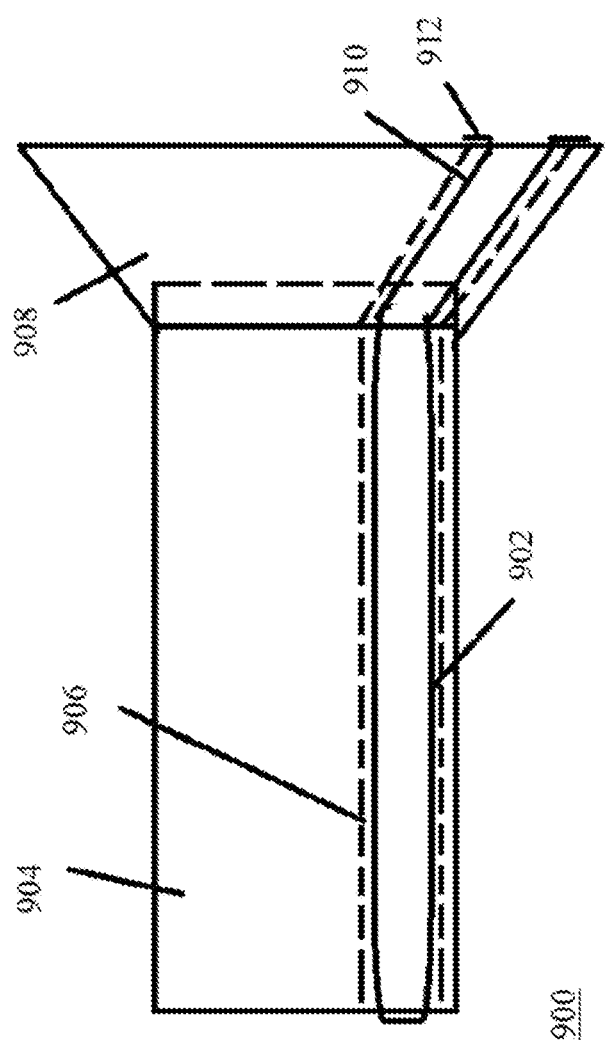

Having thus described the disclosure in general terms, reference will now be made to the accompanying drawings, which are not necessarily drawn to scale, and wherein:

FIG. 1 is a perspective view of a medical device introduction system in an embodiment of the present invention;

FIG. 2 is a perspective view of the medical introducer shown in FIG. 1, showing a plug seal in the working channel in an embodiment of the present invention;

FIG. 3 is a view of the medical introducer shown in FIG. 1, showing a plug adapter with seal in the working channel in an embodiment of the present invention;

FIG. 4 is a close-up, perspective view of the manifold of the medical introducer shown in FIG. 1, in an embodiment of the present invention;

FIG. 5 is a cross-sectional view taken along the lines 5-5 of the lumens in the manifold shown in FIG. 4, in an embodiment of the present invention;

FIG. 6 is a close-up, perspective view of the steerable working channel device position controller shown in FIG. 1, in an embodiment of the present invention;

FIG. 7 is a cross-sectional view taken along the lines 7-7 in FIG. 6 of the internal components of the steerable working channel device position controller in an embodiment of the present invention;

FIG. 8 is a close-up perspective view of the steerable working channel device proximal port shown in FIGS. 1 and 6 in an embodiment of the present invention;

FIG. 9A shows a top view of the medical introducer and steerable working channel device shown in FIG. 1, in an embodiment of the present invention wherein the position controller is in a distal position and the distal end portion is deflected to the left;

FIG. 9B shows a top view of the medical introducer and steerable working channel device shown in FIG. 1, in an embodiment of the present invention wherein the position controller is in a medial position and the distal end portion is deflected to the left;

FIG. 9C shows a top view of the medical introducer and steerable working channel device shown in FIG. 1, in an embodiment of the present invention wherein the position controller is in a proximal position and the distal end portion is fully retracted;

FIG. 9D shows a top view of the medical introducer and steerable working channel device shown in FIG. 1, in an embodiment of the present invention wherein the position controller is in a medial position and the distal end portion is deflected to the right;

FIG. 9E shows a top view of the medical introducer and steerable working channel device shown in FIG. 1, in an embodiment of the present invention wherein the position controller is in a distal position and the distal end portion is deflected to the right;

FIGS. 10A and 10B are a view of the medical introducer and steerable working channel device shown in FIG. 1, illustrating positioning of the steerable working channel tube in a uterine cavity in an embodiment of the present invention;

FIG. 11 is a close-up view of the endoscope and camera shown in FIG. 1, in an embodiment of the present invention;

FIG. 12 is a cross-sectional view of a steerable working channel showing steering wire lumens and areas of the working channel tube having different relative durometers in an embodiment of the present invention;

FIG. 13 is a view of a medical introducer tube having a lift wire lumen in an embodiment of the present invention;

FIG. 14 is a view of a medical introducer tube showing a lumen configuration having a large scope lumen and three smaller lumens for delivering a medical device and for fluids in an embodiment of the present invention;

FIG. 15 is a side view of a medical device introduction system having an accessory device support attached thereto, the accessory device support supporting an implant delivery device, in an embodiment of the present invention;

FIGS. 16A and 16B are a view of a continuous flow examination sheath useful in an embodiment of the present invention, showing both assembled and unassembled views;

FIGS. 17A and 17B are a view of a single flow examination sheath useful in an embodiment of the present invention, showing both assembled and unassembled views;

FIGS. 18A and 18B are a view of a preformed delivery tube useful in an embodiment of the present invention, showing both assembled and unassembled views;

FIG. 19 is a view of a medical device that has a slider and a rail associated with the medical device;

FIG. 20 is a view of a bent introducer tube;

FIG. 21 is a view of the introducer tube with an accompanying bent sheath;

FIG. 22 is a view of the introducer tube with an accompanying bent sheath wherein distal tip of the introducer tube and the working channel medical device are visible;

FIG. 23 is a view of a uterus wherein the introducer tube is accessing the left osteum and fallopian tube;

FIG. 24 is a view of a uterus wherein the introducer tube is accessing the right osteum and fallopian tube;

FIG. 25 is a view of a manifold wherein the manifold contains a seal that is present at the location of the working channel;

FIGS. 26A and B show an "r" curve and an "s" curve tip, respectively;

FIG. 27 shows an embodiment of the medical introducer device;

FIG. 28 shows a perspective view of the various lumens as they enter into the modular manifold;

FIG. 29 shows a perspective view of the various parts of the modular manifold, the manifold base, the seal and the manifold cover;

FIG. 30 shows the modular manifold in an unassembled state and an assembled state, with the manifold base and the manifold cover separated and then joined;

FIG. 31 shows the modular manifold with lumen core pins as they are used in the process of assembling the modular manifold;

FIG. 32 shows the modular manifold in a vertical position, which shows an embodiment of a process that allows the gluing of the manifold base and the manifold cover (with or without a seal);

FIG. 33 schematically illustrates an imaging system adapted for use with a medical device introduction system, according to various aspects of the present disclosure;

FIG. 34 schematically illustrates a cross-section of a flexible elongate tubular member adapted for use with a medical device introduction system, according to various aspects of the present disclosure;

FIG. 35 schematically illustrates a cross-section of a flexible elongate tubular member having an imaging device mounted therein, and adapted for use with a medical device introduction system, according to various aspects of the present disclosure;

FIG. 36 schematically illustrates a medical device introduction system, according to another aspect of the present disclosure;

FIG. 37 schematically illustrates a disassembled medical device introduction system, according to the aspect of the disclosure shown in FIG. 36;

FIG. 38 schematically illustrates a disassembled medical imager capable of being used in a medical device introduction system, according to the aspect of the disclosure shown in FIG. 36;

FIG. 39 schematically illustrates a medical introducer and the interaction thereof with a tube sheath, both capable of being used in a medical device introduction system, according to the aspect of the disclosure shown in FIG. 36;

FIG. 40 schematically illustrates an end view of an introducer tube of a medical introducer, in relation to the tube sheath, as implemented in a medical device introduction system, according to the aspect of the disclosure shown in FIG. 36; and FIG. 41 illustrates a perspective view of a device according to one aspect of the disclosure provided herein;

FIG. 42 illustrates a perspective view of a tip according to one aspect of the disclosure provided herein;

FIG. 43 illustrates a perspective view of a tip according to one aspect of the disclosure provided herein; and FIG. 44 illustrates a side view of a tip according to one aspect of the disclosure provided herein.

DETAILED DESCRIPTION

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

Some embodiments of the present invention can provide a medical device introduction system and/or method. For example, an illustrative embodiment of a medical device introduction system and/or method can include a medical introducer, a separate imaging system, and/or a separate working channel device. In such an embodiment, each of the medical introducer, the imaging system, and the working channel device can be movable independent of the other.

Minimally invasive surgical procedures have been developed that can be used in many diagnostic and/or therapeutic medical procedures. Such minimally invasive procedures can reduce pain, post-operative recovery time, and the destruction of healthy tissue. In minimally invasive surgery, the site of pathology can be accessed through portals rather than through a significant incision, thus preserving the integrity of intervening tissues. These minimally invasive techniques also often require only local anesthesia.

Some embodiments of the present invention can provide systems, devices, kits, and methods useful for easily and effectively accomplishing minimally invasive gynecological procedures, for example, a hysteroscopy. Such systems, devices, kits, and methods may be adapted for use in many interior body regions, wherever introduction of medical devices may be required for a therapeutic or diagnostic purpose.

As used in this specification and the appended claims, "proximal" is defined as nearer to a point of reference such as an origin, a point of attachment, or the midline of the body. As used in this specification and the appended claims, "distal" is defined as farther from a point of reference, such as an origin, a point of attachment, or the midline of the body. Thus, the words "proximal" and "distal" refer to, for example, direction, nearer to and farther from, respectively, an operator (for example, surgeon, physician, nurse, technician, etc.) who inserts a medical device into a patient, with the distal end, or tip, of the device inserted inside the patient's body. For example, the end of a medical device inserted inside the patient's body is the distal end of the medical device, while the end of the medical device outside the patient's body is the proximal end of the medical device.

As used in this specification and the appended claims, the singular forms "a," "an," and "the" include plural referents unless the context clearly dictates otherwise. Thus, for example, the term "a lumen" is intended to mean a single lumen or a combination of lumens. For the purposes of this specification and the appended claims, unless otherwise indicated, all numbers expressing quantities, conditions, and so forth used in the specification are to be understood as being modified in all instances by the term "about." Accordingly, unless indicated to the contrary, the numerical parameters set forth in this specification are approximations that can vary depending upon the desired properties sought to be obtained by embodiments of the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of embodiments of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a stated range of "1 to 10" should be considered to include any and all sub-ranges between (and inclusive of) the minimum value of 1 and the maximum value of 10. That is, a stated range of "1 to 10" should be considered to include, for example, all sub-ranges beginning with a minimum value of 1 or more, such as 1 to 6.5, and ending with a maximum value of 10 or less, such as 5.5 to 10. Additionally, any reference referred to as being "incorporated herein" is to be understood as being incorporated in its entirety.

As used in this specification and the appended claims, an "interior body region" can be a body cavity, a body space or potential space, a vein, an artery, a vessel, a duct, a pathway, an organ, or any interior site in a patient's body accessible with a medical introducer.

As used in this specification and the appended claims, an endoscope is defined as an instrument for examining an interior body region. Endoscopes are generally tools used to view within a portion of the anatomy through an open end of a tube. Flexible endoscopes may be utilized in certain deformable anatomical structures, for example, arteries, ureters, and the common bile duct. Endoscopes can be used to look directly through an objective lens or in conjunction with video cameras attached remotely to the scope for viewing a portion of the human body. Rod lens systems may also be used with some endoscopes to view images. In other endoscopes, the image may be gathered at the distal end by a lens and transferred to a proximal objective lens using fiber optic bundles.

Some embodiments of a medical device introduction system 10 and method of the present invention can include a medical introducer 20, a separate imaging system 60, and/or a separate working channel device 40. The medical introducer 20 can include a proximal end 11, a distal end 12, a handle 21, and an elongate introducer tube 23 extending from the handle 21. The introducer tube 23 can include and define a plurality of lumens extending longitudinally therein. The medical introducer 20 may be inserted into an interior body region of a patient. The separate imaging system 60 may be inserted through the handle 21 and positioned in a predetermined one of the plurality of lumens. The imaging system 60 can have an interface with the handle 21 such that each of the imaging system 60 and the medical introducer 20 is movable independent of the other. The separate working channel device 40 can include an elongate working channel tube 42 and a position controller 41. The working channel tube 42 can include at least one lumen extending the length thereof defining a working channel. The position controller 41 can be configured to control positioning of the working channel tube 42. The working channel device 40 may be removably connectable to the handle 21 and positioned in another predetermined one of the plurality of lumens. In some embodiments of the present invention, each of the medical introducer 20, the imaging system 60, and the working channel device 40 can be movable independent of the other.

In such an embodiment, the imaging system 60 can be placed into a desired position for viewing a procedure. The imaging system 60, such as the camera 61, can be held in a steady, or fixed, position, while the distal portion 12 of the steerable working channel 40 can be positioned, or re-positioned, (extended, retracted, or deflected) independent of the imaging system 60. In this manner, the starting reference point, such as the "horizon" and/or depth of the steerable working channel 40 in the interior body region can be held constant by the imaging system 60. As a result, the true movement of the steerable working channel relative to a certain starting point can be gauged. Alternatively, the steerable working channel device 40 can be held in a fixed position so as to maintain a fixed orientation, or reference point, of the working channel tube portion 42 of the working channel in the interior body region. While the steerable working channel device 40 is held in a constant position, the position of imaging system 60 can be adjusted independent of the steerable working channel device 40. In this manner, the true movement of the imaging system 60 relative to a certain starting point can be gauged.

In addition, while holding the imaging system 60 in a fixed position, the medical introducer 20 can be independently rotated about its longitudinal axis 33 if desired. Rotation of the medical introducer 20 may be desired for purposes such as adjusting the starting position of the steerable working channel tube 42 prior to extending or deflecting the distal tip of the working channel tube 42, or reorienting fluid outflow at a target area in the interior body region. In this manner, the true movement of the medical introducer 20 relative to a certain starting point can be gauged. Likewise, if desired, the medical introducer 20 and the attached steerable working channel device 40 can be held in a constant position so as to maintain a fixed orientation, or reference point, of the working channel tube 42 and the working channel in the interior body region. While the medical introducer 20 and the attached steerable working channel device 40 can be held in a constant position, the position of imaging system 60 can be adjusted. In this manner, the true movement of the imaging system 60 relative to a certain starting point can be gauged.

This combination of separate and cooperating components of embodiments of the present invention allows for more precise control of instrument positioning and delivery of materials, such as fluids, medications, and implants, in an interior body region. Independent position control and movement of the imaging system 60 relative to the medical introducer 20 and to the steerable working channel device 40 allows optimal visualization of a target operative site within an interior body region.

An embodiment of the medical device introduction system 10 of the present invention can include a medical introducer 20. As used herein, a "medical introducer" is defined as an instrument used to introduce a medical device, for example, a tube, stent, catheter, and/or surgical instrument, into an interior body region of a human or animal.

In some embodiments of the present invention, the medical introducer device 20 can include the handle 21 comprising an oval-shaped ring of material having an open interior, a proximal end, and a distal end. The introducer 20 can further include an elongate introducer tube 23 extending from the distal end 15 of the handle 21 and having a plurality of lumens extending longitudinally therein. The proximal end 14 of the handle 21 can be configured to receive at least one fluid tube 24, 25 and the imaging system 60 through the handle 21. The distal end 15 of the handle 21 can be adapted to connect to the introducer tube 23, as described herein. Such a medical introducer 20 can be inserted into an interior body region of a patient.

The plurality of lumens in a medical introducer tube 23 can include a scope lumen 34, at least one working lumen 35, and at least one fluid lumen 36 separate from the scope lumen 34 and the working lumen(s) 35. The medical introducer 20 can further include a fluid inflow tube 24 routed through the proximal end of the handle 21 and in fluid communication with one of the at least one fluid lumen 36. The medical introducer 20 can further include the fluid outflow tube 25 routed through the proximal end of the handle 21 and in fluid communication with another one of the fluid lumen(s) 36. In certain embodiments, the diameter of the working lumen 35 can be larger than the diameter of the other lumens 34, 36.

In an embodiment, the working lumen 35 can accommodate medical devices, which can place medications and/or provide implants to an interior body region. However, these medical devices sometimes need to be removed and/or resubmitted. When this occurs, there is the danger of backflow from fluids from the interior body region. Accordingly, in one embodiment, the medical devices of the present invention also possess a manifold 250 and seal 251 as shown in FIG. 25, which will aid ameliorating, diminishing and/or eliminating the backflow of fluids. It should be noted the similarities between FIG. 25 and for example, FIG. 13, wherein the manifold 250 is designed in a way to accommodate the various lumens as shown in FIG. 13. Note that the working lumen 35 is the one that may have medical devices inserted and removed so the manifold 250 contains the seal 251 in the position that is designed to accommodate these medical devices. The seal 251 in some embodiments has flaps associated with it that allow the passage of the medical device but preclude the passage of fluid one the medical device has been removed. The manifold 250 may be made of a plastic that provides the medical device with additional structural integrity that might not otherwise be present.

The medical introducer 20 can be utilized to perform diagnostic procedures, for example, by using the dedicated fluid-in and fluid-out lumens 36 and tubes 24, 25, respectively, to irrigate an interior body region and retrieve a sampling of washings from the targeted region for diagnostic tests. Alternatively, or in addition, the medical introducer 20 can be utilized to perform therapeutic procedures, for example, by using the dedicated working lumen 35 to introduce a device for placing a medication and/or an implant into an interior body region.

The fluid-in tube 24 can include a pinch clamp 26 for on-off regulation of fluid delivery into the interior body region. The fluid-out tube 25 can include a roller clamp 27 for graduated regulation of fluid flow out of the interior body region. In other embodiments, regulation of fluid flow on both the fluid-in tube 24 and the fluid-out tube 25 can be managed by different regulation mechanisms, for example an electronic fluid pump for fluid delivery or a suction device for fluid removal. Separate dedicated fluid lumens 36 and tubes 24, 25 in embodiments of the present invention can allow better fluid flow, for example, more continuous fluid flow, than conventional medical device introducers that often deliver fluid to an interior body region through a working lumen 35 in which a medical device may be placed simultaneously.

The medical introducer 20 can include a modular manifold 22 integrally formed on the proximal end of the introducer tube 23 and have a corresponding plurality of lumens aligned with the plurality of lumens in the introducer tube 23. The manifold 22 may be removably connected to the handle 21 such that the manifold 22 and introducer tube 23 are interchangeable in the handle 21 with other manifolds 22 and introducer tubes 23.

As shown in FIG. 4, the handle 21 can be connected to the manifold 22 by snapping a groove, or cut-out in the distal end 15 of the handle 21 about a correspondingly shaped handle receiving groove 48 in the manifold 22. The manifold 22 can include a handle support 49 extending downwardly from the bottom of the manifold below the handle receiving groove 48. When the handle 21 is removably snap fit about the handle receiving groove 48 in the manifold 22, the distal end 15 of the handle 21 can abut the handle support 49 to provide further support of the positioning of the handle 21 on the manifold 22.

In an embodiment, the manifold 22 (a slightly different embodiment of a manifold 250 is also shown from a top down angle in FIG. 25) may be introduced in a region between the handle and the proximal end of the introducer tubes 23. In one embodiment, the manifold is removable. In alternate embodiments, the manifold may be attached with medically safe glues that are thermally attached. One potential drawbacks to the use of thermal glues is that in the manufacturing process, one needs to make sure that appropriate plastics are used that have melting points above the thermal set point of the glue. Otherwise, one risks excessive costs (and possibly defective medical devices) that result from melting plastic (e.g., holes in the plastic lumens, etc.). In a further embodiment, the manifold may be attached with medically safe glue that relies on setting by the administration of UV light (or some other wavelength from the electromagnetic spectrum that allows the glue to set). The advantage of using these UV setting glues is that one does not have to worry about plastic melting on the medical device.

In an embodiment in which a separate imaging system 60 is inserted through the handle 21 and positioned in a predetermined lumen 34 in the medical introducer 20, the imaging system 60 can have an interface with the handle 21 such that each of the imaging system 60 and the medical introducer 21 is movable independent of the other. In certain embodiments, the medical introducer device 20 can cooperate with a separate working channel device 40. The separate working channel device 40 can comprise an elongate working channel tube 42 having at least one lumen extending the length thereof defining a working channel and a position controller 41 for controlling the position of the working channel tube 42. The working channel device 40 can be removably connected to the handle 21 and positioned in a predetermined lumen 35 in the medical introducer 21 separate from the imaging system 60, such that each of the medical introducer 20, the imaging system 60, and the working channel device 40 is movable independent of the other.

In some embodiments, the medical introducer device 20 can be disposable. In some embodiments, at least a portion of the medical introducer device 20 can be translucent such that passage of materials therethrough can be viewed.

The introducer tube 23 can include a proximal 11 portion having a first durometer and a distal portion 12 having a second durometer. As used herein, durometer is defined as a degree of hardness; a harder material comprises a higher durometer than a softer material. The second durometer can be lower than the first durometer so as to allow deflection of the distal portion 12 for controllable access to a target area in the interior-body region. The introducer tube distal portion can include a distal tip 13 having a first diameter smaller than a second diameter of the remainder of the introducer tube 23, such that the smaller first diameter is adapted to seal about a device extending beyond the distal tip 13. The introducer tube 23 can further include a fluid lumen 36 comprising a wall having a third durometer that is higher than the second durometer of the distal portion 12 so as to prevent collapsing of the fluid lumen 36 when the distal portion 12 of the introducer tube 20 is deflected.

In some embodiments, the introducer handle 21 can have a size adapted to be readily held in a hand of a user. In some embodiments, the introducer handle 21 can further include a plurality of raised grips 32 on an outside surface of the handle 21 to assist in manipulating the handle 21.

Embodiments of the medical introducer 20 can have varied numbers, sizes, and configurations of lumens 34, 35, 36 in the introducer 20. Embodiments of the medical introducer 20 can have various lengths, depending on the particular interior body region it is designed to access and on the particular medical procedure for which it is designed. For example, in some embodiments, the medical introducer 20 can include a 7 French size dedicated working lumen 35 so as to support passage of larger devices than conventional multiple lumen delivery devices having the same outside diameter. This advantage is provided by having a smaller dedicated scope lumen 34 and extruding the manifold 22 and introducer tube 23 with smaller wall thicknesses.

In certain embodiments, the introducer handle 21 can include a scope connector 28 located on the proximal end 14 of the handle 21. The scope connector 28 can be longitudinally aligned with the one of the plurality of lumens 34 in the introducer tube 23. The imaging system 60 can be securely connected to the scope connector 28, for example, with a luer lock fitting. When the imaging system 60 is securely connected to the scope connector 28, the imaging system 60—medical introducer 20 interface is adapted to allow the imaging system 60 to rotate independent of movement of movement of the medical introducer 20.

The medical introducer 20 can be formed in a molding process by a plastic or polymeric material. The medical introducer 20 can be formed from materials and in such a manner so as to have most, or all, components be translucent, thereby enabling visualization and visually-guided passage of instruments and fluids through the introducer 20. Such visualization may also assist with establishing delivery routes as discussed herein. Further, such visualization may allow for the identification of a gaseous material (e.g. air) within a channel, and/or confirmation of the absence of such gaseous material within a channel.

The lumen 35 in the medical introducer 20 designed for inserting the steerable working channel device 40 can be sealed with a sealing mechanism. Such a seal 37 can be a duckbill seal or a one-way valve, including a luer fitting. The seals 37 can provide frictional or abutting contact with the inner surface of the working lumen 35 in the manifold 22. Such a seal 37 mechanism can allow medical devices and/or fluid, for example, gas or liquid, to pass through the seal mechanism 37 toward the distal end of the introducer tube 23, and can inhibit fluid from passing from the interior body region through the proximal end 11 of the introducer tube 23.

In certain embodiments, the medical introducer 20 can be inserted into an interior body region with a trocar system (not shown). A trocar can comprise a cannula that may have a sharp distal tip for creating a percutaneous path to the interior body region. Once the trocar is in a desired position in or adjacent the target interior body region, the medical introducer 20 can be inserted through the trocar to the target site. In such an application, a portion of the patient's body needs to be penetrated or opened where a body cavity does not provide a ready opening. Such a trocar system can be used, for example, for prostate surgery. In this manner, a trocar system, or other endoscopic device, can assist in providing a path through which the medical introducer 20 can enter the portion of the interior body region of a patient into which a medical procedure is desired to be performed.

The medical introducer 20 can be utilized to perform diagnostic procedures, for example, by using the dedicated fluid-in and fluid-out lumens 36 and tubes 24, 25 to irrigate an interior body region and retrieve a sampling of washings from the targeted region. Alternatively, or in addition, the medical introducer 20 can be utilized to perform therapeutic procedures, for example, by using the dedicated working lumen 35 to introduce a device for placing an implant into an interior body region.

In an alternative embodiment, the medical introducer 20 can further include an inflatable portion associated with the distal portion of the introducer tube 23. The inflatable portion can be utilized to distend or enlarge a cavity, space, or portion of an interior body region and/or block fluid passage from the interior body region when the introducer tube 23 is positioned therein.

In another aspect of the present invention, some embodiments can include a working channel device 40 that is steerable. The entire length of the working channel tube 42 can be flexible. Alternatively, a substantial portion of the working channel tube 42 can be generally rigid, or semi-rigid, and a distal portion 12 of the working channel tube 42 can be flexible. In such embodiments, as shown in FIGS. 1, 6, 7, and 9, the working channel tube 42 can include a flexible distal portion 12 adapted for steering to selected positions. In such embodiments, the position controller 41 can be operably connected to the working channel tube distal portion 12 and slidable within the introducer handle 21 for moving the working channel tube distal portion 12 in distal and proximal directions. In addition, the position controller 41 can be actuatable to steer the flexible distal portion 12 of the working channel tube 42 in predetermined directions and amounts. For example, the predetermined direction of steering can be in a plane generally parallel to an upper surface of the position controller 41.

In embodiments of a steerable working channel device 40, the device 40 can include, for example, at least two steering wires (not shown). Each steering wire has a distal end connected to the distal tip 13 of the working channel tube 42. Each steering wire can extend through the working channel tube 42, and have a proximal end operably connected to the position controller 41. In this way, the position controller 41 can be actuated to manipulate the distal portions 12 of the working channel tube 42.

In certain embodiments of the steerable working channel tube 42, the position controller 41 can further include a circular, lower housing 51 having an upwardly extending hollow hub 54 and a cooperating circular, upper housing 50 having a downwardly extending rotor 55 rotatingly seated inside the hollow hub 54. Each of the steering wires can be connected to an opposite side of the position controller rotor 55 such that rotation of the upper housing 50 causes rotation of the rotor 55 inside the hub 54, resulting in the distal end of the steering wire on one side of the rotor 55 to retract so as to deflect the distal tip 13 at an angle laterally away from the longitudinal axis 33 of the working channel tube 42.

As described herein, the introducer handle 21 can comprise an oval-shaped ring of material having an open interior. The open handle 21 can have a plurality of detents (not shown) on the inner surface of the handle 21 from the proximal position 31 to the medial position 30 to the distal position 29. The lower housing 51 of the position controller 41 can further include a downwardly extending bracket 52 adapted to friction fit in the inner surface of the handle 21 and a securing flange 53 extending outwardly from the bracket 52 adapted to friction fit about a bottom of the handle 21. Accordingly, the position controller 41 can be slidingly engageable with the detents (not shown) so as to secure the position, of the working channel tube distal portion 12 and distal tip 13 along the longitudinal axis 33 of the working channel tube 42.

The position controller 41 can further include an automatic braking mechanism (not shown). For example, the braking mechanism can comprise a soft material on the outer surface of the upper housing rotor 55 and/or the outer surface of the lower housing hub 54 so as to provide sufficient friction to hold the upper housing 50 in position relative to the lower housing 51 when released by a user.

In some embodiments, the working channel tube 42 can further include a proximal 11 portion having a first durometer and a distal 12 portion having a second durometer. The second durometer can be lower than the first durometer so as to allow deflection of the distal portion 12 for improved access to a target area in the interior body region. The working channel tube distal portion 12 can further include the distal tip 13 having a first diameter smaller than a second diameter of the remainder of the working channel tube 42. The smaller first diameter can be adapted to seal about a device extending beyond the distal tip 13. Each or either of the proximal or distal portions may, in some embodiments, comprise a plurality of durometers to enhance steering.

It should be appreciated that other mechanisms for steering, for example, two finger deflection, may be utilized in some embodiments without departing from the present invention.

In certain embodiments, the working channel device 40 can further include at least one access port 38 having a seal 39. The sealed access port 38 can be connected to the proximal end 11 of the working channel tube 42 for controllable access to the steerable working channel.

The position controller 41 can have a size adapted to be readily held in a hand of a user. The position controller 41 can further include a plurality of grips 47 on lateral edges of the position controller 41 to assist a user in manipulating the position controller 41.

In certain embodiments, the working channel can be utilized to deliver instruments, fluids, medications, implants, or other materials into an interior body region. The steerable working channel device 40 can be positioned in at least one other of the plurality of lumen 35 of the medical introducer 20 so that the separate steerable working channel device 40 and the imaging system 60 are independently controllable. In some embodiments, the working channel device 40 can be disposable and intended for a single use.

An example of an embodiment of a flexible distal portion 12 and steering wire configuration is shown in FIG. 12. In this embodiment, the working channel tube of the steerable working channel device 40 can comprise a proximal 11 insertion portion, a distal portion 12, and a distal tip 13. The proximal 11 insertion portion can be formed of a semi-rigid material 67, for example, pellethane having a 75 durometer hardness rating. The distal portion 12 can be formed of a combination of a relatively harder material 67, such as a 75 durometer pellethane, and a relatively softer, flexible material 68, such as pellethane having a 55 durometer. The portion of the distal portion 12 having different relative hardness can be co-extruded. The distal tip 13 can be formed of a semi-rigid material 67, which can be the same material from which the proximal 11 insertion portion is formed (for example, pellethane having a 75 durometer). In certain embodiments, other materials can be used to form the elongate tube 42 of the steerable working channel device 40.

The working channel tube 42 can include at least one steering lumen 66 in each lateral aspect of the tube 42. The steering wires can be routed from the position controller 41 through the steering wire lumens 66 through the flexible distal portion 12 and attached to the distal tip 13. The distal tip 13 is preferably formed of a harder material 67, such as a 75 durometer Pellethane, to provide a strong and firm anchor for the small diameter stainless steel steering wires that may cut through a softer material 68 when retracted. The flexible distal portion 12 can include a relatively softer material 68 in each of the lateral aspects through which the steering wire lumens 66 are formed, and a relatively harder material 67 in the dorsal and ventral aspects of the distal portion 12 tubing. Such a configuration can permit the distal portion 12 to deflect in a predetermined manner and amount. The presence of the relatively harder material 67 in the distal portion 12 allows the relatively softer, lateral sections 68 to deflect without compressing when extreme deflection is occurring, which can result in exposing an instrument in the steerable working channel more than desired. Different relative durometers of material can be utilized to achieve a relative hardness/softness ratio between sections of the distal portion 12 so as to allow directionally-controlled deflection of the distal portion 12 of the working channel tube 42.

When the position controller upper housing portion 50 is rotated, one of the steering wires connected to the rotor 55 is wound about the rotor 55, causing the distal end of that steering wire to retract. This retraction pulls on the lateral side of the distal tip of the working channel tube 42 to which it is connected so as to "deflect" the distal tip and distal portion 12 at an angle 57 laterally away from the longitudinal axis 33 of the working channel tube 42, as shown in FIGS. 9 and 10. The position controller upper housing 50 can be rotated in the opposite direction to place tension on, or retract, the other steering wire and thereby "deflect" the distal portion 12 of the working channel tube 42 in the opposite direction. The position controller 41 can thus control the angular attitude of the distal portion 12 of the working channel tube 42. The steering wires in cooperation with the position controller 41 can be configured to limit angular adjustments of the distal portion 12 to a plane extending generally parallel to the upper surface of the position controller 41. For example, the configuration of the position controller 41 and the steering wires can be such that angular deflection 57 of the distal portion 12 of the working channel tube 42 can be limited to no more than 30 degrees, 45 degrees, or another predetermined limit. In other embodiments, various other steering mechanisms, such as one or more position deflectors associated with the working channel tube 42, can be used in accordance with the present invention.

In some embodiments, the position controller 41 can include a braking mechanism (not shown) for securing the upper and lower housing portions 50, 51, respectively, into position relative to each other. The braking mechanism can comprise, for example, a soft polymeric material, such as silicone, coated onto the outer surface(s) of the upper housing rotor 55 and/or the lower housing hub 54. In this fashion, the coated surface can allow the rotor 55 to rotate smoothly within the hub 54, while providing sufficient friction to hold the rotor 55 and the hub 54 of the upper and lower housings 50, 51, respectively, in position when released by an operator. In certain embodiments, in addition to providing a polymeric coating on the rotor 55 and/or hub 54 outer surfaces, one or both of these surfaces can be textured so as to provide further friction and greater securing force between the rotor 55 and hub 54. Such a braking mechanism is simple, inexpensive, and avoids any need for stronger mechanical or gear-based braking mechanisms. In particular embodiments, such a polymeric coating braking mechanism can be combined with other braking means.

As will be appreciated, a braking mechanism, of fixing in an alternate manner, in some embodiments, advantageously allows a predetermined route of delivery to be established. An advantageous result is increased precision and reduced time for procedures. Further, in some embodiments, the steerable working channel may be fixed prior to insertion into a patient.

In certain embodiments, for example, those that include a polymeric coating on the outer surfaces of the rotor 55 and hub 54, the internal brake mechanism can hold position automatically when steered to a particular point. This feature provides a physician with a precise control that is maintained when her/his fingers are removed from the position controller 41, for example, to perform another task during a procedure.

The position controller 41 can be adapted to control movement (extension and retraction) of the working channel tube 42 in the proximal and distal directions. In some embodiments, the inside of the medical introducer handle 21 can include detents (not shown) at various stop points along the length of the handle 21. For example, the medical introducer handle 21 can include a detent at a proximal position 31, medial position 30, and a distal position 29 on the inside of the handle 21. The bracket 52 and securing flange 53 on the lower side of the position controller 41 can slide along the length of the handle 21. When the securing flange 53 reaches a detent, the securing flange 53 engages the detent so as to secure the position controller 41 in that position. In this manner, as shown in FIG. 9, the position controller 41 can be moved in the proximal and distal directions and snap fit into detents at respective proximal 31, medial 30, and distal 29 positions in the handle 21 so as to control the distance the distal tip 13 of the working channel tube 42 extends beyond the distal tip 13 of the introducer tube 23 of the medical introducer 20. In certain embodiments, the proximal end 31 of the medical introducer handle 21 can include a recess to allow clearance for the working channel tube 42 extending from the proximal end 11 of the steerable working channel device 40, the connection port 38, and any attached accessories to slide the entire length of the handle 21 in the proximal direction.

The position controller 41 can have a size adapted to fit between the fingers and thumb of an operator. In some embodiments, for example, as shown in FIGS. 6 and 7, the center of the position controller 41 can include a thumb depression 45, designed to allow a physician to place a thumb in the depression 45 to move the position controller 41 in the proximal and distal directions along the length of the medical introducer 20. The upper surface of the upper housing 50 of the position controller 41 can include a circular ridge 46 about the center of the position controller 41. The circular ridge 46 can provide a physician an ability to locate the center of the position controller 41 by "feel" rather by having to look at the controller 41.

In some embodiments, as shown for example, in FIGS. 1, 6, and 8, the position controller 41 can include a plurality of raised ridges, or grips, 47 on the lateral side edges of upper housing 50. The grip 47 surfaces can include a soft, tactile material that can provide improved grip and performance with the position controller 41. Such grips 47 can provide a positive grip on the upper housing 50 for rotating the upper housing 50 in the process of deflecting the distal portion 12 of the working channel tube 42.

The steering mechanism can provide the physician sufficient control of the distal tip 13 of the elongate tube 42 of the steerable working channel device 40 so as to manipulate the distal tip 13 of the working channel tube 42 for specific isolation on particular sections of an interior body region. The steering mechanism can allow the physician to steer the working channel tube 42 while simultaneously providing access to a lumen within the steerable working channel for inserting and using various surgical instruments and fluids. That is, the steering mechanism can provide the control and manipulation of the distal tip 13 the working channel tube 42 of the steerable working channel device 40 needed for use with the surgical instruments and fluids required for a procedure.

Another feature of some embodiments is that the insertion depth of the working channel device may be set to a predetermined value using the mechanisms described herein for steering and fixing the working channel.

In some embodiments, the steerable working channel device 40 as well can be controllable independent of the imaging system 60 positioned in the medical introducer 20 and independent of the medical introducer 20. Such a system can be used in a variety of medical procedures, including, for example, gynecological, fertility, hysteroscopy, or prostate type applications. For example, the medical device introduction system 10 and medical introducer 20 can be advantageously utilized in procedures and products related to insemination, profusion, intrauterine blastocyst/embryo transfer, endoscopic evaluation and operations, laparoscopy (that is, culdoscopy, transvaginal hydro laparoscopy), and/or falloscopy. Accordingly, both fluid management and medical instruments usage may be a managed through the working channel device 40 independent of or separate from both the imaging system 60 and the medical introducer 20.

In certain embodiments, the separate working channel device 40—insertable through a separate lumen 35 in the medical introducer 20 from the lumen 34 in which the imaging system 60 is inserted—can be a non-steerable working channel device 40. In such an embodiment, the working channel device does not have a steering mechanism associated with the device 40. However, the non-steerable working channel device can be moved in the distal and proximal directions within one of the lumen 35 of the medical introducer 20.

In some embodiments of the separate working channel device 40, the proximal end 11 of the working channel tube 42 can include one or more access ports 38, as shown in FIGS. 1 and 6. Such access ports 38 can be sealed with a port seal 39. Such a seal 39 can be formed of an elastomeric material such as silicone rubber and have a very small axial opening through the material that permits a small object such as a needle to enter, but which otherwise prevents fluid flow in either direction, and thus protects the lumens from receiving contaminating materials therein, in some embodiments, the proximal access 38 on the working channel tube 42 can comprise a luer lock fitting and seal 44 for controllable access to the steerable working channel.

In some embodiments, the imaging system 60 can include an endoscopic cannula 62, a light delivery mechanism, and an imaging device. The imaging system can include at least one of an optical scope, an ultrasound instrument, and/or a camera 61. A camera may be positioned on a distal 12 portion of the endoscopic cannula 62.

In some embodiments, the introducer handle 21 can further include a scope connector 28 located on an opposite side of the handle 21 from the introducer tube 23 and longitudinally aligned with the one 34 of the plurality of lumens in the introducer tube 23. In this manner the imaging system 60 can be securely connected to the scope connector 28. In this configuration, that is, when the imaging system 60 is securely connected to the scope connector 28, the imaging system 60 can rotate independent of movement of the medical introducer 20.

In some embodiments, the endoscopic cannula, or endoscope, 62 can be rigid. In other embodiments, the endoscope 62 can be flexible. An embodiment of a flexible endoscopic cannula 62 can include a proximal 11 portion having a first durometer and a distal 12 portion having a second durometer. The second durometer is lower than the first durometer, which can allow deflection of the distal portion 12 for improved viewing of a target area in the interior body region. Some embodiments of the imaging system 60 can further include at least two steering wires (not shown), each wire having its distal end connected to the distal tip 13 of the endoscopic cannula 62. The steering wires can extend at least the length of the endoscopic cannula 62. The proximal end of the steering wires can be operably connected to a deflection control mechanism at the proximal end 11 of the endoscopic cannula 62. In this way, actuation of the deflection control mechanism can cause the distal tip 13 of the endoscopic cannula 62 to deflect at an angle away from the longitudinal axis 33 of the imaging system 60. The endoscopic cannula 62 can include each of a first pair of wires adjacent opposite points on a circumference of the endoscopic cannula 62 to deflect the distal tip along a first axis. The endoscopic cannula 62 can also include each of a second pair of wires adjacent two other opposite points on the circumference of the endoscopic cannula 62. Each of the second pair of wires can be positioned 90 degrees from each of the first pair of wires, to deflect the distal tip along a second axis perpendicular to the first axis.

In some embodiments, the light delivery mechanism can include one or more light emitting diodes (not shown) mounted at a distal tip of the endoscopic cannula 62. In other embodiments, the light delivery mechanism can include a plurality of light delivery fibers (not shown) attached to the endoscopic cannula 62 and extending from the proximal end 11 to the distal tip 13 of the endoscopic cannula 62. The light delivery mechanism can further include a light source (not shown) comprising a light cable attached on one end to a power source and on the opposite end to the light delivery fibers at the proximal end 11 of the endoscopic cannula 62. Alternatively, the light delivery mechanism can further include a light source comprising one or more light emitting diodes connected to the light delivery fibers at the proximal end 11 of the endoscopic cannula 62. In another embodiment, the light delivery mechanism can include a plurality of light delivery fibers integrated into the endoscopic cannula 62 that extend from the proximal end 11 to the distal tip 13 of the endoscopic cannula 62. In this embodiment, the light delivery mechanism can further include a light source comprising a light cable attached on one end to a power source and on the opposite end to the light delivery fibers at the proximal end 11 of the endoscopic cannula 62. Alternatively, the light delivery mechanism can further include a light source comprising light emitting diodes in the introducer handle connected, to the light delivery fibers.

In some embodiments, the medical device introduction system 10 of the present invention can include an imaging system 60. The imaging system 60 can be separate from the medical introducer 20, and can be positioned in a predetermined one 34 of the plurality of lumens of the medical introducer 20, for example, in the dedicated scope lumen 34. The scope lumen 34 can be configured to receive various types of imaging systems 60 therein. The imaging system 60 can be removably connected to the medical introducer 20.

As described herein, in various embodiments of the medical device introduction system 10, the imaging system 60 can be operated independent of the medical introducer 20 and/or the working channel device 40, thereby permitting a steady, or constant, view of a particular anatomical structure or site in an interior body region while the introducer 20 and/or the working channel device 40 are manipulated. Such an independent operation of the imaging system 60 can be accomplished, for example, through cooperation of the imaging system 60 with the scope port, or connector, 28 as shown in FIGS. 1-3.

The scope connector 28 is fixed to, for example, by being integrally molded with, the proximal end 14 of the medical introducer handle 21. The scope connector 28 can be positioned in longitudinal alignment with the dedicated scope lumen 34 in the introducer manifold 22. The scope connector 28 can include a molded luer lock fitting, which allows the scope 62 to be securely connected to the introducer handle 21, and to also rotate about its longitudinal axis 33 independent from movement of the medical introducer 20. In an application in which the scope 62 is not secured to the introducer handle 21, the imaging system 60 can also be rotated about its longitudinal axis 33 independent from movement of the medical introducer 20. In this way, the medical introducer 20 and/or the working channel device 40 associated therewith can be moved without moving the imaging system 60. As a result, the view through the imaging system 60 can remain constant, providing a fixed reference point for movement of the introducer 20 and/or working channel device 40, and thereby allowing the physician to maintain a steady, right-side-up orientation of view and movement in the interior body region.

The imaging system 60 can comprise, for example, an optical scope, such as a fiber optic scope, a camera 61, a charge couple device (CCD), a camera positioned on the distal tip 13 and/or distal portion 12 of an elongate shaft 62, known as a "chip-on-a-stick," or ultrasound or other sonic device. The imaging system 60 can include a light source (not shown) for illuminating an interior body region. The light source can be separate from, and removably connected to, the imaging system 60. Alternatively, the light source can be integrated with the imaging system 60. As shown in the embodiment in FIGS. 1, 3, and 11, the imaging system 60 can include a fiberscope 62 operably connected to an ocular mechanism, such as an endoscope lens 63, to adjust focus or light intensity. The fiberscope 62 can be, for example, a 2.0 mm 50 K fiberscope, and the endoscope lens 63 can be a 2.9 mm 30 degree rod lens. As shown in this embodiment, the imaging system 60 can be a "low profile" camera 61, which is less bulky, weighs less, and more easily maneuverable than other cameras, and is configured to readily cooperate with other components of the medical device introduction system 10.

The imaging system 60 can be connected to a monitor or other display mechanism for viewing an image within at least a portion of the interior body region into which the imaging system 60 is inserted. The imaging system 60 can be connected to an image capture mechanism, for example, a computer-readable medium such as a computer hard drive, a memory stick, a compact disc, a digital versatile disc, magnetic tape, or other storage medium, for recording images viewed via the imaging device.

In another aspect of the present disclosure, as shown, for example, in FIG. 33, the imaging system 60 may comprise a body member 400 including a light source 425 configured to emit light. A flexible elongate tubular member 450 has a proximal portion 450A operably engaged with the body member 400, and extends to an opposed distal portion 450B. An imaging device 475 (see, e.g., FIG. 35) is engaged with the distal portion 450B of the tubular member 450 and is configured to be in communication with the body member 400. The imaging device 475 is arranged with respect to the distal portion 450B of the tubular member 450 so as to be directed, and to be capable of capturing an image, in an imaging direction 480 outwardly of the distal portion 450B.

A plurality of light transmission devices 500 is operably engaged with and extends from the light source 425 and through the tubular member 450 to respective distal ends 505 thereof disposed about the distal portion 450B of the tubular member 450. The light transmission devices 500 are configured to receive the light from the light source 425 and to transmit the light to the distal ends thereof 505, such that the light is emitted from the distal ends 505. The distal ends 505 of the light transmission devices 500 are arranged about the imaging device 475, about the distal portion 450B of the tubular member 450, so as to direct the light transmitted from the light source 425 in the imaging direction 480, outwardly of the distal portion 450B of the tubular member 450.

In some instances, the flexible elongate tubular member 450 may comprise, for example, a braided elastic filiform material configured to transmit torque between the proximal and distal portions 450A, 450B of the tubular member 450. The braided elastic filiform material may comprise, for instance, a stainless steel braided sleeve or hose, though a braided filiform material of various types could also be used (i.e., by varying the arrangement of the braiding or weaving) to provide desirable characteristics in terms of the ability to transmit torque, while maintaining the desirable flexibility of the tubular member 450 along the length thereof. The tubular member 450 is preferably sufficiently flexible, at least about the distal portion 450B thereof, to conform to the curvature of the distal portion 12 of the introducer tube 23, as disclosed elsewhere herein. In other instances, if necessary or desired, a rigid elongate conduit 440 may be engaged between the body member 400 and the flexible elongate tubular member 450 so as to be capable of transmitting torque between the body member 400 and the flexible elongate tubular member 450. In still other instances, if necessary or desired, the rigid elongate conduit 440 may extend over the flexible elongate tubular member 450 about the engagement thereof with the body member 400. In further instances, the tubular member 450 may comprise an external polymeric sheath 460 disposed externally to the braided filiform material 455 and/or an internal polymeric sheath 465 disposed internally to the braided filiform material 455 (see, e.g., FIG. 34). Such polymeric sheaths 460, 465 may comprise separate and discrete tubes that may be coaxially arranged with the braided filiform material 455. In other instances, the polymeric sheaths 460, 465 may be engaged with the braided filiform material, for example, in a co-extrusion or coating process. In some instances, as further disclosed herein, the tubular member 450 may be employed to carry a plurality of light transmission devices (i.e., light delivery fibers) therein and, as such, it may be desirable for the external and/or internal polymeric sheaths 460, 465 to be opaque to preserve the light transmitted by the light transmission devices 500 through the distal ends 505 thereof.

In some aspects, the tubular member 450 may further comprise a terminal member 525 engaged with the braided filiform material 455 about the distal portion 450B of the tubular member 450. That is, termination of the braided filiform material 455 may result in loose/protruding filaments of the braided material. Accordingly, the terminal member 525 may be applied to cap or seal the terminus of the braided filiform material 455, for instance, to prevent such loose/protruding filaments. However, the terminal member 525 may also be configured to receive and secure the imaging device 475 and/or the distal ends 505 of the light transmission devices 500.

In one aspect, the light transmission devices 500 may comprise fiber optic elements or light delivery fibers. In another aspect, the imaging device 475 may comprise an active-pixel sensor array or a Complementary Metal-Oxide Semiconductor (CMOS) sensor. It may be desirable, in some instances, for the imaging device 475 to capture images substantially in real time or at least with minimal delay between image capture and display. In such aspects, the imaging device 475 may be configured as a quadrilateral, generally configured to be received within a lumen defined by an inner wall (i.e., the braided filiform material 455 or the internal polymeric sheath 465) of the tubular member 450. In such instances, it may be preferable that the imaging device 475 be received and arranged so as to be disposed perpendicularly to a longitudinal axis of the tubular member 450 (i.e., the longitudinal axis of the tubular member 450 extends perpendicularly through the plane of the imaging device 475). Further, in general, the lumen defined by the tubular member 450 has a non-polygonal cross-section. That is, the lumen defined by the tubular member 450 may be configured to have, for example, a circular, oval, or ovate cross-section. In some particular instances, the imaging device 475 may be configured as a square (i.e., having a diagonal dimension of about 2.3 mm), and is received within a lumen configured to have a circular cross-section having, for example, an inner diameter of about 2.3 mm (see, e.g., FIG. 35), and the light transmission devices 500 may comprise fiber optic elements or light delivery fibers having the distal ends 505 thereof arranged about the imaging device 475 in the segments of the circular lumen unoccupied by the imaging device 475. In such a configuration, the unoccupied segments about the imaging device 475 may each include the distal ends 505 of a plurality of fiber optic elements or light delivery fibers. In this manner, significant illumination may be directed from the distal ends of the light transmission devices 500 outwardly of the distal portion 450B of the tubular member 450, in the imaging direction 480, for improving the images captured by the imaging device 475. One skilled in the art will thus appreciate that the imaging device 475 and the distal ends 505 of the light transmission devices 500 arranged about the imaging device 475 may be disposed within the lumen defined by the tubular member 450. However, one skilled in the art will also appreciate that the imaging device 475 and the distal ends 505 of the light transmission devices 500 arranged about the imaging device 475 may be engaged with or mounted to the terminal member 525, with the terminal member 525, in turn, engaged with or mounted to the distal portion 450B of the tubular member 450. In the latter, it may also be preferred that the imaging device 475, configured as a square, is engaged with or mounted to the terminal member 525 configured to have a circular cross-section (see, e.g., FIG. 35), wherein the distal ends 505 of the light transmission devices 500 (i.e., fiber optic elements or light delivery fibers) are arranged about the imaging device 475 in the segments of the circular terminal member 525 unoccupied by the imaging device 475.

Due to the disposition of the imaging device 475 about the distal portion 450B of the tubular member 450, the imaging system 60 may further comprise a communication element 550 operably engaged with the body member 400 (i.e., so as to minimize the footprint of the imaging device 475). The communication element 550 may be configured and arranged to be in signal communication with the imaging device 475, for example, so as to receive an image signal therefrom associated with the image captured thereby or to communicate electrical power to the imaging device 475.

For instance, the imaging device 475 may be configured to be in wireless communication with the communication element 550 comprising a wireless transceiver. In other instances, the imaging device 475 may be in communication with the communication element 550 by way of a wired or wireline communication extending between the imaging device 475 and the communication element 550, through the tubular member 450. The communication element 550 may comprise any arrangement suitable for receiving image signals from the imaging device 475, and for directing electrical power to the imaging device 475. The communication element 550 may also be configured or comprise elements suitable to direct the image signal externally to the imaging system 60, such as, for instance, to an external display device 575 or computer device 600. In such instances, minimizing the components included in the imaging system 60 may allow the imaging system 60 to be a single-use device (i.e., disposable) from an economic standpoint. Otherwise, the imaging system 60 may be configured so as to promote effective sterilization and re-use.

In particular aspects, the imaging system 60 may also comprise a display device 575 (i.e., a monitor, tablet computer, or smartphone) for displaying the image associated with the image signal received from the communication element 550 and/or a computer device 600 (i.e., tablet computer, laptop, or desktop computer) for storing or analyzing the image associated with the image signal received from the communication element 550. The display device 575 and/or the computer device 600 may be in communication with the communication element 550 (i.e., a circuit board having appropriate circuitry), for example, via a wired communication arrangement or a wireless communication arrangement.

Since the light source 425 may be carried by the body member, in some instances, the imaging device 60 may also include a power source 625 operably engaged with the body member 400, wherein the power source 625 is arranged to at least be in electrical communication with the light source 425. In some aspects, it may also be desirable for the power source 625 to be in electrical communication with the imaging device 475. The power source 625 may comprise a self-contained power source, such as a battery, capacitor, or other suitable source of electricity, so as to promote portability of the imaging system 60. In other instances, however, the power source 625 may be in electrical communication with the light source 425 and/or the imaging device 475 via a wired arrangement. In aspects including a self-contained power source 625, such as a battery, the power source 625 may be removably secured to the body member 400 (i.e., to promote separate and discrete recharging of the battery, or so as to allow one battery to be readily replaced with another). For example, a magnetic connector arrangement or any other suitable removably securement arrangement may be provided between the power source 625 and the body member 400. In some particular aspects, the removably secured power source 625 may also carry the light source 425, wherein the light source 425 would be configured and arranged to engage the light transmission elements 500 upon engagement of the power source 625 with the body member 400. In any instance, in the event that the electrical power provided by the power source 625 results in resistive heating, the power source 625 may, in some instances, comprise a heat shield 650 at least partially surrounding the power source 625.

Aspects of an imaging device 60, as illustrated in FIG. 33, can thus be applied as a component of a medical device introduction system 10, as otherwise disclosed herein, or as part of an associated device, kit, method of use, or method of manufacture, as will be appreciated by a person skilled in the art. More particularly, a medical device introduction system 10 implementing such an imaging system 60 may be configured to include a medical introducer 20 comprising a handle 21 and an elongate introducer tube 23 extending from the handle 21 to a distal end 12, wherein the introducer tube 23 includes and defines a plurality of lumens extending longitudinally therein from the handle 21 to the distal end 12. The imaging system 60, as shown in FIG. 33, may thus be arranged such that the body member 400 is configured to be received by the handle 21, and the tubular member 450 is configured to be insertable through the handle 21 and positionable in one of the lumens 34 so as to extend to the distal end 12 of the introducer tube 23. In aspects implementing a rigid elongate conduit 440, the conduit 440 may be configured to be received by the handle 21 and the tubular member 450 may be configured to be received by the one of the lumens 34 of the introducer tube 23. In any aspect, the distal end 13 of the medical introducer 20 may be configured as a compound curve, and at least the distal portion 450B of the tubular member 450 is configured to flex during longitudinal movement of the tubular member 450 within the one of the lumens 34 to conform to the compound curve of the distal end 13 of the medical introducer 20.

In some such aspects of the present invention, a securing device/scope connector 28 may be engaged with the handle 21 of the medical introducer 20, wherein the scope connector 28 is configured to receive the tubular member 450 therethrough. The securing device/scope connector 28 is configured to secure the tubular member 450 such that the imaging device 475 is disposed in a selected longitudinal position along the introducer tube 23 and such that the tubular member 450 is rotatable about a longitudinal axis thereof within the introducer tube 23. That is, in some instances, it may be desirable for the tubular member 450 to be fixed in a particular longitudinal position with respect to the introducer tube 23 such that the imaging device 475 is positioned as desired with respect to the distal portion 12/distal tip 13 of the introducer tube 23. At the same time, it may be desirable for the tubular device 450 to be rotatable about the longitudinal axis thereof with respect to the introducer tube 23, for example, so as to maintain the horizon of the image captured by the imaging device 475, as the medical introducer 20 is manipulated. In some instances, the securing device/scope connector 28 may comprise, for example, a compression fitting engaged with the handle 21, coaxially with the longitudinal axis, wherein the compression fitting is configured to be rotatable about the longitudinal axis. As such, the compression fitting may be secured to the tubular member 450 when the imaging system 60 is engaged with the handle 21 in the desired longitudinal position, wherein the structure of the compression fitting then allows the tubular member 450 to be rotated about the longitudinal axis, as necessary or desired. In facilitating the reception of the imaging system 60 by the medical introducer 20, a mounting interface/slide member or mechanism 71 may be operably engaged with the handle 21 and configured to receive and secure at least the body member 400 of the medical imaging system 60 such that the medical imaging system 60 and the medical introducer 20 are movable relative to each other (i.e., such that the body member 400 is supported by the slide member 71 as the tubular member 450 is moved along the introducer tube 23, or as the body member 400 is rotated about the longitudinal axis to, in turn, rotate the tubular member 450 within the introducer tube 23).

Embodiments of medical device introduction systems and methods of the present invention provide advantages over conventional systems and methods. The cooperation of the medical introducer 20, related to, for example, the modular introducer handle 21 and introducer tube 23 and fluid delivery in dedicated lumens 36; the separate steerable working channel device 40, including ease of introduction of accessory devices and precision of device positioning and utilization through the working channel; the separate imaging system 60 delivered through a dedicated lumen 34; and the control of each of the medical introducer 20, steerable working channel device 40, and imaging system 60 independent of each other device provide for effectiveness of operation.

Such medical device introduction systems and methods of the present invention can allow a physician, or other medical personnel, to control and manipulate the working channel device 40, an imaging source 60, and other medical devices inserted into an interior body region through the medical introducer 20, while simultaneously using surgical tools and fluids needed for such procedures. In this manner, the physician may be allowed to positionally locate, isolate, and view problem areas with greater precision within the interior body region than with conventional medical device introduction systems and methods. That is, control of visualization, access, and use of instrumentation in the operative site environment can be enhanced by the cooperation of the various combinations of components as described herein. In part due to the simple design, embodiments of the present invention can be easy to use and thus may require minimal training. Such factors can allow a physician to utilize embodiments of the present invention to perform procedures in an office setting which may have previously been avoided due to complexity and cost.

In particular, the ability to maintain a constant, or fixed, point of reference, for example, by keeping the imaging system 60 steady while re-positioning the medical introducer 20 and/or the working channel device(s) 40 can provide greater control over the medical procedure, and may decrease operative time. Embodiments of medical device introduction systems 10, devices 20, kits, and methods of the present invention can be utilized in conjunction with procedures that are minimally invasive. Whether used alone or in the context of minimally invasive procedures embodiments of the present invention can advantageously provide, for example, performing the procedure on an outpatient basis, reduced trauma to the target area, reduced anesthesia time, reduced recovery time, and decreased discomfort to the patient. As an example, in a hysteroscopy system, an embodiment of the present invention can allow a fixed endoscope 62 position, thereby minimizing tissue trauma as compared to conventional hysteroscopy procedures. In addition, minimal outside diameters of the medical introducer 20 and associated components resulting in smaller devices can decrease the need for anesthesia and can increase patient comfort related to a procedure.

Single use components can be safer than reusable devices due to the decrease or elimination of risk for transmission of communicable infections and diseases between patients. Single use components can be more cost-effective due to elimination of cleaning and sterilization expense and decreased expense for repairs associated with reusable devices.

In another aspect of the present invention, certain embodiments of the medical introducer 20 can further include a lift wire not shown) attached on its proximal end to a distal tip lift control (not shown), such as a knob similar to the steerable working channel device position controller 41. The lift wire can be routed through a dedicated lift wire lumen 69, as shown in FIG. 13, through the length of the medical introducer tube 23 and attached on its distal end to the distal tip 13 of the introducer tube 23. The distal lift control can be moved in the proximal direction so as to pull the lift wire in the proximal direction, thereby deflecting the distal tip 13 of the introducer tube 23 in one direction. When the distal tip 13 of the introducer tube 23 is lifted, any device therein will also be lifted, or deflected, along with the introducer tube 20. In operation, the introducer tube 20 can be inserted in the straight position (along its longitudinal axis).

In an exemplary embodiment, a flexible medical device, such as a flexible hysteroscope, can be inserted in the working channel, or lumen, 35 of the medical introducer 20. Once the introducer tube 23 is inserted in the straight position into the uterine cavity 64 (FIG. 10) and the cavity 64 distended, the distal tip lift control can be moved in the proximal direction so as to lift the distal tip of the introducer tube 23 in one direction. The introducer 20 can then be rotated to view the extreme left and right aspects of the uterine cavity 64. The distal tip of the introducer tube 23 can be further positioned and aligned with the tubal osteum for delivery of an instrument or implant to the fallopian tube 65. Such an embodiment can thus provide a simple operation for lifting, or deflecting, a steerable working channel device 40, imaging system 60, or other medical device in an interior body region.

Some embodiments of a medical device introduction system 10 of the present invention can include an accessory device support 70, as shown in FIG. 15. The accessory device support 70 can be removably connected to the introducer handle 21. The accessory device support 70 can comprise a carrier arm 72 for supporting an upper part of a body of a separate medical device 73 to be used with the medical introducer 20, and a slide member (or mechanism) 71 for slidably supporting a lower part of the body of the separate medical device 73. This accessory device support 70 can be used to stabilize placement of additional separate medical devices (73) in the interior body region. In certain embodiments, the accessory device support 70 can be removably connected to the outside surface of the scope connector 28 on the proximal end of the introducer handle 21.

An embodiment of the present invention can include a delivery catheter having a small delivery channel, or working lumen 35, as shown in FIG. 14. Such a configuration allows the scope lumen 34 to be larger than, for example, the embodiment shown in FIG. 5. In the embodiment shown in FIG. 14, the catheter can be inserted into the interior body region in the straight position. For example, a flexible hysteroscope can be introduced into the uterine cavity 64 in the straight position via a small delivery catheter. Once inserted, and the cavity 64 is distended, the medical introducer 20 can be rotated to provide an optimal viewing angle. The flexible hysteroscope can have a pre-formed "angle up" distal tip 13, and can be inserted via the working delivery channel in an obturator. Once in the uterine cavity 64, the obturator can be removed, and the angled distal tip is restored for use. This enables a zero degree angle of view flexible scope to be utilized and a more effective access approach to particular pathologies. Such a small diameter delivery catheter can assist visualization and access in difficult to reach pathology. In addition, a small diameter catheter can improve patient comfort relative to larger delivery catheters.

As shown in FIG. 16, an embodiment of the present invention can include a continuous flow examination sheath 80. This device 80 can be single-use and utilized for quick evaluation or hysteroscopy, for example. The continuous flow examination sheath 80 can include a formed distal tip 81, an insertion portion 82, a fluid-out adapter 84, a fluid-in adapter 83, a finger grip 85, a proximal port 86, and an inner sheath 87. An endoscope 62 can be inserted through the proximal port 86 through a fluid seal adapter (not shown). The fluid-in tube 83 can allow a physician to deliver fluid to clear the scope 62 lens or distend the uterine cavity 64 for improved visualization. In addition, the fluid-out adapter 84, and tube, can allow the physician to clear fluid from the cavity 64 that may impair viewing caused by blood present at the site.

As shown in FIG. 17, an embodiment of the present invention can include a single flow examination sheath 90. This device 90 can be single-use and utilized for quick evaluation or hysteroscopy, for example. The single flow examination sheath 90 can include a formed distal tip 81, an insertion portion 82, a fluid-in adapter 83, a finger grip 85, a proximal port 86, and a nose piece 91. An endoscope 62 can be inserted through the proximal port 86 through a fluid seal adapter. The fluid-in tube 83 can allow a physician to deliver fluid to clear the scope lens or distend the uterine cavity 64 for improved visualization.

As shown in FIG. 18, an embodiment of the present invention can include a pre-formed delivery catheter 100. The pre-formed delivery catheter 100 can include a formed distal tip 81, an insertion portion 82, an adapter 101, a finger grip 85, a proximal port 86, and a nose piece 91. This device 100 can be used for delivering another medical device or treatment to a specific site when a steerable mechanism is not practical. Fluid can be incorporated by adapters known in the art, for example, a Touhy Borst adapter and a side port entry attached to the proximal end of the catheter 100.

In another embodiment, an endoscopy system utilized in the present invention can be a wireless handheld endoscopy system (not shown). Such a system can include an endoscopic cannula 62, a disposable mount, a focus/zoom function, a wireless camera, for example, a 2.4 GHz, high resolution camera used in cooperation with a laptop or other monitor, and controls for imaging and power.

Some embodiments of a medical device introduction system 10 can be utilized with a conventional endoscope trocar system (not shown), for example, for abdominal minimally invasive surgery. The medical introducer 20 can be inserted through a 10 mm or 5 mm trocar and can be sealed by the internal trocar seal. When inserted with a conventional trocar system, embodiments of the present invention can retain all functionality described herein, including depth adjustment for the medical introducer 20, 360 degrees of rotation, depth adjustment for the steerable working channel device 40, and angle and direction of deflection adjustment, visualization, and access related to the working channel device 40.

Some embodiments of the present invention can include a kit comprising one or more of various components of a medical device introduction system 10, including a medical introducer 20, a separate imaging system 60, and/or a separate working channel device 40. The medical introducer 20 can include a handle 21 and an elongate introducer tube 23 extending from the distal end 15 of the handle 21. The introducer tube 23 can include a plurality of lumens 34, 35, 36 extending longitudinally therein. The medical introducer 20 may be inserted into an interior body region of a patient. The separate imaging system 60 may be inserted through the handle 21 and positioned in a predetermined one 34 of the plurality of lumens. The imaging system 60 can have an interface with the handle 21 such that each of the imaging system 60 and the medical introducer 20 is movable independent of the other. The separate working channel device 40 can include an working channel tube 42 and a position controller 41. The working channel tube 42 can include at least one lumen extending the length thereof defining a working channel. The position controller 41 can be configured to control positioning of the working channel tube 42. The working channel device 40 may be removably connectable to the handle 21 and positioned in another predetermined one 35 of the plurality of lumens. In some embodiments of a kit of the present invention, each of the medical introducer 20, the imaging system 60, and the working channel device 40 can be movable independent of the other.

In certain embodiments, the medical introducer handle 21 can comprise an oval-shaped ring of material having an open interior. The handle 21 can have a proximal end 14 configured to receive at least one fluid tube 24, 25 and the imaging system 60 therethrough. The handle 21 can further include a distal end 15 adapted to connect to the introducer tube 23. In certain embodiments, the plurality of lumens in the introducer tube 23 can include a scope lumen 34, at least one working lumen 35, and at least one fluid lumen 36 separate from the scope lumen 34 and the working lumen(s) 36. In an illustrative embodiment, the medical introducer 20 can further include a fluid inflow tube 24 routed through the proximal end 14 of the handle 21 and in fluid communication with a fluid lumen 36, and a fluid outflow tube 25 routed through the proximal end 14 of the handle 21 and in fluid communication with another fluid lumen 36.

In some embodiments, the medical introducer 20 can include a modular manifold 22 integrally formed on the proximal end 11 of the introducer tube 23 and have a corresponding plurality of lumens 34, 35, 36 aligned with the plurality of lumens 34, 35, 36 in the introducer tube 23. The manifold 22 can be removably connected to the introducer handle 21 such that the manifold 22 and introducer tube 23 are interchangeable in the handle 21 with other manifolds 22 and introducer tubes 23. In particular embodiments, a kit can include a plurality of manifolds 22 and introducer tubes 23, such that one manifold 22 and introducer tube 23 in a kit may be interchanged on a handle 21 with another one of the manifolds 22 and introducer tubes 23 in the kit.

In some embodiments, the medical introducer 20 and/or the working channel device 40 can be disposable. In some embodiments, at least a portion of the medical introducer 20 and/or at least a portion of the working channel device 40 can be translucent such that passage of materials therethrough is viewable.

In some embodiments, one or more of the introducer tube 23, the working channel tube 42, and the endoscopic cannula 62 can include a proximal 11 portion having a first durometer and a distal 12 portion having a second durometer. The second durometer is lower than the first durometer so as to allow deflection of the distal 12 portion of the respective tube or cannula for controllable access to a target area in the interior body region.

In certain embodiments, the working channel device 40 can be a steerable working channel device 40. In such an embodiment, the working channel tube 42 can comprise a flexible distal portion 12 for steering to selected positions. The position controller 41 can be operably connected to the working channel tube distal 12 portion and slidable within the introducer handle 21 for moving the working channel tube distal 12 portion in distal and proximal directions. In addition, the position controller 41 can be actuated to steer the flexible distal 12 portion of the working channel tube 42 in predetermined directions and amounts.

In some embodiments, the imaging system 60 can include an endoscopic cannula 62, a light delivery mechanism (not shown), and a imaging system. The light delivery system can comprise light emitting diodes and/or light delivery fibers. The imaging system can be an optical scope 62, an ultrasound instrument, or a camera 61.

In certain embodiments, a kit can include other devices and/or instruments that may be used with the medical device introduction system 10. For example, such a kit may include an accessory device support 70 removably connectable to the outside surface of a scope connector 28 on the proximal end 14 of the introducer handle 21. The accessory device support 70 can comprise a carrier arm 72 for supporting an upper part of a body of a separate medical device 73 to be used with the medical introducer 20 and a slide member 71 for slidably supporting a lower part of the body of the separate medical device 73. Such an accessory device support 70 may be used to facilitate and stabilize placement of a separate medical device 73 in the interior body region.

The present invention can include embodiments of a method. For example, a medical introducer 20 comprising a handle 21 and an introducer tube 23 extending therefrom and having a plurality of lumens 34, 35, 36 extending longitudinally therein can be inserted into an interior body region of a patient. A separate imaging system 60 can be inserted through the handle 21 and in a predetermined one of the plurality of lumens 34, 35, 36. The imaging system 60 can be positioned in a selected position within the interior body region. Then, an image can be produced from within the interior body region. A separate working channel device 40 and position controller 41 can be removably connected to the medical introducer 20. The working channel device 40 can include an working channel tube 42 having at least one lumen extending the length thereof defining a working channel. The position controller 41 for controlling the position of the working channel tube 42 can be positioned in the working channel in another predetermined one 35 of the plurality of lumens. In such embodiments, one of the group of the medical introducer 20, the imaging system 60, and the working channel device 40 may be moved independently of the others of the group.

In some embodiments of a method, the medical introducer handle 21 can comprise an oval-shaped ring of material having an open interior. The method can further include connecting a distal end of the handle 21 to the introducer tube 23. In some embodiments of a method, the medical introducer 20 can include a modular manifold 22 integrally formed on a proximal end 11 of the introducer tube 23 and have a corresponding plurality of lumens 34, 35, 36 aligned with the plurality of lumens 34, 35, 36 in the introducer tube 23. In such an embodiment, the manifold 22 can be removably connected to the introducer handle 21. The manifold 22 and introducer tube 23 may be interchanged in the handle 21 with other manifolds 22 and introducer tubes 23.

In an embodiment, a slider 191 and rail 192 may be used in conjunction with a medical device 190 to accommodate the handle of the medical device 190. For example, the slider 191 and rail 192 may be used to accommodate a medical device 190 such as that disclosed in U.S. Pat. No. 8,079,364, which is herein incorporated by reference in its entirety. The rail 192 is designed so as to accommodate the slider 191 so as to serve as a means of holding the medical device 190. In one embodiment, the slider 191 and the rail 190 when serving as a holder of the medical device 190 means that fewer hands are needed in surgery. Without the slider 191 and rail 192, a nurse or some other personnel is needed to hold the medical device 190 to prevent the medical device from turning when inserted into a cavity (for example, into the uterine cavity). Thus, the slider 191 and rail 192 stabilizes the handle without having additional hands having to hold the device.

For example, when a fallopian tube sterilization is performed, often a nurse is required to hold the handle of a medical device 190 while the surgeon operates the device so as to insert an additional medical device or to perform some procedure (such as cauterization or the like). By using the slider 191 and rail 192, the nurse is no longer required to hold the device as the surgeon performing the surgery is able to not only manipulate the distal tip of the medical device to perform the sterilization by inserting the tip through the one or more osteums into the fallopian tube, but is also able to hold the medical device due to the presence of the slider 191 and rail 192. The nurse or other medical personnel is then available to perform other duties (such as helping the anesthesiologist or providing the necessary medical devices to the surgeon).

The uterine cavities in all patients tend to be slightly different. The locations of the osteum may differ slightly from patient to patient meaning that the location of the fallopian tubes may also differ. In one embodiment, the slider 191 and rail 192 may be able to accommodate a medical device 190 that contains a steerable distal tip for a working channel device. The slider 191 and rail 192 in combination with the steerable distal tip allow the surgeon to use a scope to identify the location of the osteum(s) and then to insert a medical device, an example of which is disclosed in U.S. Pat. No. 7,921,848. U.S. Pat. No. 7,921,848 is herein incorporated by reference in its entirety.

In an embodiment, rather than having a steerable distal tip, the distal tip of the medical device may be bent. When performing a female sterilization such as a tubal ligation or a tubal occlusion the bent distal tip may make it easier to access the osteum. Other procedures that can be done include diagnostic hysteroscopy, polypectomy, myomectomy, a directed uterine biopsy, fundal biopsy, endometrial harvesting or tubal patency. See for example, the bent distal tip as shown in FIG. 20. In one embodiment, the angle at which the distal tip is disposed cannot be altered. In other embodiments, the distal tip may be part of the introducer tube that can be bent and thus, altered. When the introducer tube cannot be altered, an osteum (or either of the two ostei) can be accessed by adjusting the distance that the working medical device is inserted into the vagina. When a more acute angle is desired, the surgeon will pull the medical device out more and when a less acute angle is desired, the surgeon will push more of the medical device into the uterus. In any event, by this methodology, the ostei and fallopian tubes can be accessed.

In a variation of this embodiment, the diameter of introducer tube 23 in this embodiment may be less than the diameter of an introducer tube of a medical device that has a steerable distal tip. This is because the working channel medical device no longer requires the mechanism necessary for steering the distal tip. Accordingly, components such as the steering and/or lift wires that are necessary in a steerable working channel medical device are not required to move the distal tip.

In an alternative embodiment, a sheath that has an inner diameter that is slightly larger than the outer diameter of the working channel medical device may be placed over the distal end of the introducer tube. In several embodiments, the sheath may be bent and may be of sufficient structural integrity so that the sheath also bends the distal end of the medical device to the same degree as the sheath. In one embodiment, a surgeon may use a sheath that is bent at an angle that is 10 degrees from straight. If a scope is associated with the working channel medical device, the surgeon may view the inside of the uterus to ascertain the relative locations of the ostei. There may be other sheaths that are bent at any of a plurality of degrees from straight that can then be inserted over the introducer tube so the appropriate orientation is realized to allow access to the ostei. For example, there may be bent sheaths that may be 10 degrees, 20 degrees, 30 degrees, or 40 degrees from straight. By selecting the correct sheath (after ascertaining the orientation to approach the ostei), the surgeon can most readily perform the procedure in the fallopian tube that is to be performed. An example of the bent sheath can be seen in FIGS. 21 and 22. FIGS. 23 and 24 show the bent sheath with the introducer tube and the working channel medical device approaching the left osteum and left fallopian tube (FIG. 23) and the right osteum and right fallopian tube (FIG. 24). In an embodiment, one might access the right osteum after accessing the left osteum merely by turning the handle 180 degrees (which in turn changes the orientation of the distal tip from accessing the left osteum to being able to access the right osteum or vice versa).

In an embodiment, the present medical device does not rely on the distal tip being correctly oriented by a steerable working channel medical device but rather relies rather on the distal tip of the introducer tube being bent or alternatively, a sheath that fits over the introducer tube that is bent. When the sheath is bent, it has sufficient structural stability so as to bend the distal tip of the working channel medical device. The advantage of these systems is that they require less manipulation at the proximal end of the medical device by the surgeon. The proper orientation is achieved simply by having the correct bend in the introducer tube or the sheath that is designed to accommodate the introducer tube. When the system employing a sheath is used, this system has the advantage that different orientations of the distal tip can be achieved simply by having a plurality of different sheaths that are all bent to slightly different degrees. It should be noted that the orientation may be slightly modified from the plurality of bent sheaths by the relative position of the sheath as it relates to the introducer tube. The closer the sheath is to the proximal end of the medical instrument (closer to the surgeon), the larger the bend of the distal tip end. That is, by having the bend closer to the proximal end, the distal tip will be a further distance from straight.

FIGS. 26A and 26B show two different embodiments of the present invention, the "r" curved embodiment and the "s" curved embodiment, respectively. FIG. 26B shows an introducer with a compound-curved tip 261 that allows the positioning of an imaging device further from an object 262 relative to the simple curve 260. When the introducer is inserted into a small body cavity or vessel, different views of an anatomical site can be attained. The view angle profile of the anatomical site is indicated in both FIGS. 26A and 26B by dotted lines 265 and 265'. Note that because the viewing angles are the same, the further distance 264 of the compound curve relative to the lesser distance 263 of the simple curve allows the user to view more area around the object 262. Nevertheless, in either embodiment, the object 262 to be addressed can be done with steerable working channel 266.

In one embodiment, the compound-curved introducer distal tip (the intersection of dotted lines 265 and 265') is positioned at a distance 264 that is 3-10 mm further from the object 262 (such as an osteum) than a simple curved introducer tip distance 263. The embodiment in FIG. 26B provides more space for the steerable working channel 266 to extend (deploy) out of the distal tip of the introducer and as well as space to be steered (articulated) or deflected within the field of view (265 and 265') of the imaging device and to place in alignment with the tubal osteum to deliver an implant, instrument, energy source, or to perform some therapeutic procedure. The simple-curved device of FIG. 26A provides less working space for a steerable working channel between the introducer distal tip and the object (e.g., the osteum).

In some embodiments, and as shown in FIGS. 27 and 28, the medical introducer 20 can include a modular manifold 271 integrally formed on the proximal end 11 of the introducer tube 23 and having a corresponding plurality of parallel aligned lumens 34, 35, 36 in the introducer tube 23. The manifold can incorporate seal(s) 292 (see FIG. 29) to prevent fluid flow from out of a body cavity or vessel when no instrumentation is in the working channel 35. The seal(s) 290 do(es) not allow fluid or gas flow from a distal position to a proximal position through specified lumens in the introducer tube 23 but may allow fluid and/or gas to flow in the opposite direction.

The specified lumens in the modular manifold 271 are created by joining a manifold base 291 and a manifold cover 292 (see FIGS. 29 and 30) with the seal 290 (shown in FIG. 29 but not shown in FIG. 30) positioned in the interior of the combined manifold base 291 and manifold cover 292. The manifold base 291, manifold cover 292 and introducer tube 23 can be assembled to form integrally isolated lumens corresponding with the plurality of lumens 34, 35, 36 and introducer tube 23 by aligning the plurality of lumens 34, 35, 36 with sized Teflon core pins 301 (see FIGS. 30 and 31), which hold the relative positions of the plurality of lumens 34, 35, 36 and the introducer tube 23 in place. In an embodiment, one can inject/insert UV curable glue 321 (see FIG. 32) into the assembly at junction 323 between the manifold base 291 and manifold cover 292. The introducer tube 23 with lumen core pins 301 and the modular manifold 271 are all held in a vertical position when inserting the glue (see FIG. 32). The assembly is held in a vertical position so as to allow the passage of the glue by gravity down into the manifold cover 292, which also secures the seal 290 (not shown in FIG. 32) in place. The transparent assembly is subsequently then exposed to UV light to cure the UV glue injected between manifold base 291 and introducer tube 23 contained by cover 292. The core pins 301 can then be removed from the modular manifold 271 containing integral seal(s) 290.

In one embodiment, the seal 290 is situated and is of a type so as to allow the passage of fluid in a direction that is from the proximal end of the introducer medical device to the distal end of the introducer medical device but does not allow passage of fluid in the other direction. In another embodiment, the seal may allow passage of fluid in the other direction. In another embodiment, the seal may prevent passage of fluid at all, or allow only the passage of low viscosity fluids while substantially blocking the passage of medium and/or high viscosity fluids.

In still another aspect of the present disclosure, as shown, for example, in FIGS. 36-40, a medical device introduction system 700 may be adapted to be at least partially insertable into an interior body region of a patient. Such a system 700 may comprise a medical imager 750, a medical introducer 800, and a tube sheath 850. The medical imager 750 may include a body member 755 (see, e.g., element 400 in FIG. 33) being configured as or otherwise including a handle 760, and including a light source (see, e.g., element 425 in FIG. 33) disposed within the handle 760. A flexible elongate tubular member 765 (see, e.g., element 450 and, optionally, element 440, shown in FIG. 33) extends from the body member 755 to an opposed distal portion 770. The tubular member 765 includes an imaging device (see, e.g., element 475 in FIG. 35) engaged with the distal portion 770 thereof. Similarly to the imaging device shown as element 475 in FIG. 35, the imaging device is arranged and configured to be in communication with the body member 755 (i.e., in signal communication with a communication element 550 as shown in FIG. 33). A plurality of light transmission devices (see, e.g., element 500 in FIG. 33) extend from the light source, and through a lumen defined by the tubular member 765, to respective distal ends thereof (see, e.g., elements 505 in FIG. 35) disposed about the distal portion 770 of the tubular member 765, and arranged about the imaging device (see, e.g., FIG. 35). The light transmission devices are configured to receive the light from the light source and to transmit the light to the distal ends thereof.

In particular aspects, the imager 750 is configured similarly to that shown and described in association with FIGS. 33-35. As such, since details of such an imager 750 have already been disclosed herein, such details are not repeated in their entirety in relation to the aspects shown in FIGS. 36-40. In any instance, in light of the previous disclosure herein regarding the imager 750, particular aspects of such an imager 750 will be readily apparent. For example, the light transmission devices (see, e.g., element 500 in FIG. 33) may comprise fiber optic elements or light delivery fibers. In addition, the imaging device (see, e.g., element 475 in FIG. 35) may comprise an active-pixel sensor array or a Complementary Metal-Oxide Semiconductor (CMOS) sensor.

In some aspects, the imaging device (see, e.g., element 475 in FIG. 35) may be configured as a quadrilateral, and is received within a lumen defined by an inner wall of the tubular member 765 of the imager 750, perpendicularly to a longitudinal axis of the tubular member 765, with the lumen being configured to have a circular, oval, or ovate cross-section. In particular aspects, the imaging device (see, e.g., element 475 in FIG. 35) is configured as a square, and is received within a lumen defined by an inner wall of the tubular member 765 of the imager 750, perpendicularly to a longitudinal axis of the tubular member 765, with the lumen being configured to have a circular cross-section. In such instances, the light transmission devices (see, e.g., element 500 in FIG. 33), comprising fiber optic elements or light delivery fibers, have the distal ends (see, e.g., element 505 in FIG. 35) thereof arranged about the imaging device (see, e.g., element 475 in FIG. 35) in the segments of the circular lumen unoccupied by the imaging device.

In other aspects, a power source 900 (see, e.g., element 625 in FIG. 33) is operably engaged with the body member (see, e.g., element 400 in FIG. 33), wherein the power source 900 is arranged to be in electrical communication with the light source (see, e.g., element 425 in FIG. 33). The power source 900 may be removably secured to the body member 755, for example, via a magnetic connector arrangement. In addition, a heat shield (see, e.g., element 650 in FIG. 33) may be implemented to wrap about or to surround the power source 900.

In still further aspects, a communication element 950 (see, e.g., element 550 in FIG. 33) may be operably engaged with the body member 755, wherein the communication element 950 is arranged in signal communication with the imaging device (see, e.g., element 475 in FIG. 33) so as to receive an image signal therefrom associated with the image captured thereby or to communicate electrical power to the imaging device. In addition, a display device (see, e.g., element 575 in FIG. 33) for displaying the image, or a computer device (see, e.g., element 600 in FIG. 33) for storing or analyzing the image, may be in communication with the communication element 950 via a wired communication arrangement or a wireless communication arrangement.

In additional aspects, the flexible elongate tubular member 765 may comprise a braided elastic filiform material configured to transmit torque between the proximal and distal portions of the tubular member. In some instances, the tubular member 765 may comprise an external polymeric sheath disposed externally to the braided filiform material, or an internal polymeric sheath disposed internally to the braided filiform material. In particular aspects, the external polymeric sheath and the internal polymeric sheath are opaque to preserve the light transmitted by the light transmission devices (see, e.g., element 500 in FIG. 33). Further, the tubular member 765 may comprise a terminal member (see, e.g., element 525 in FIG. 33) engaged with the braided filiform material about the distal portion 770 of the tubular member 765, wherein the terminal member is configured to receive and secure the imaging device and the distal ends of the light transmission devices.

The medical introducer 800 is comprised of a flexible elongate introducer tube 805 extending from a proximal end 810 to a distal end 815. The introducer tube 805 defines at least one lumen 820 extending longitudinally within the introducer tube 805 from the proximal end 810 to the distal end 815, wherein the lumen 820 is configured to receive the tubular member 765 of the imager 750 therein. More particularly, in some instances, the introducer tube 850 is configured to receive the tubular member 765 of the imager 750 within the lumen 820, such that the imaging device (see, e.g., element 475 in FIG. 35) engaged with the distal end 770 of the tubular member 765 is disposed about the distal end 815 of the introducer tube 805.

In accordance with some aspects of the present disclosure, a transparent member 835 (see, e.g., FIG. 40) may extend across and seal the distal end of the lumen 820 (i.e., about the distal end 815 of the introducer tube 805) configured to receive the tubular member 765 of the imager 750 therein. In such aspects, the distal end 770 of the tubular member 765 is disposed adjacent or in proximity to the transparent member 835, wherein the transparent member 835 is configured to direct light from the light transmission devices (see, e.g., element 500 in FIG. 33) therethrough and/or to allow the imaging device (see, e.g., element 475 in FIG. 35) to receive or capture an image therethrough. Since the lumen 820 is sealed about the distal end 815 of the introducer tube 805, the tubular member 765 of the imager 750 is and will remain isolated with the lumen 820 during use of the medical device introduction system 700. Accordingly, the sealed lumen 820 may facilitate less frequent or no required sterilization of the imager 750 and/or re-usability of the imager 750.

In particular aspects, the introducer tube 805 may define a plurality of lumens (see, e.g., elements 820, 821, 822, and 823 in FIG. 40), with each lumen extending longitudinally within the introducer tube 805 from the proximal end 810 to the distal end 815. That is, as shown in FIG. 40, the introducer tube 805 may define at least four lumens 820, 821, 822, 823, wherein one lumen 821 may comprise a working channel for receiving surgical instruments therethrough. In such instances, an engagement device 830, such as a luer fitting may be engaged about the proximal end 810 of the introducer tube 805 and in communication with the one lumen 821. In this manner, the luer fitting may be configured to engage, secure, and/or form a seal with the surgical instrument inserted into the working channel, with respect to the introducer tube 805. The remaining two lumens 822, 823 may comprise, for example, fluid in and out channels for directing fluid through one lumen 822 from the proximal end 810 toward the distal end 815 (inflow), and for directing fluid through the other lumen 823 from the distal end 815 toward the proximal end 810 (outflow). As shown, for example, in FIGS. 36 and 37, irrigation inflow and outflow tubes 824, 825 may be engaged and in fluid communication with the lumens 822, 823 arranged and configured a fluid in and out channels, so as to facilitate engagement with fluid/irrigation equipment.

In particular instances, the proximal end 810 of the introducer tube 805 is configured to non-rotatably engage the tubular member 765 or the body member 755 of the imager 750. That is, a securing device 827 may be engaged with the proximal end 810 of the introducer tube 805, and configured to receive the tubular member 765 of the imager 750 therethrough. In some instances, the proximal end 810 of the introducer tube 805 may itself be configured as the securing device 827. In particular instances, the securing device 827 is configured to secure the tubular member 765 with respect to the introducer tube 805 such that the imaging device (see, e.g., element 475 in FIG. 35) is disposed in a selected longitudinal position along the introducer tube 805, and such that the tubular member 765 is non-rotatable about a longitudinal axis thereof within the introducer tube 805. For example, the securing device 827, or otherwise the proximal end 810 of the introducer tube 805 (i.e., at least the lumen 820 configured to receive the tubular member 765 of the imager 750 therein), may define a keyed receptacle (not shown) configured to engage a keyed flange (i.e., element 767 of FIGS. 37 and 38) associated with the tubular member 765 or the body member 755 of the imager 750, in a snap fit or a friction fit, such that the introducer tube 805 is removably and non-rotatably affixed to the tubular member 765 or the body member 755 of the imager 750.

As shown in FIGS. 36, 37, and 39, the elongate tube sheath 850 extends from a proximal end 855 to a distal end 860. The tube sheath 850 may further define a lumen 865 (see, e.g., FIG. 40) configured to receive the introducer tube 805 therein. In particular aspects, the proximal end 855 of the tube sheath 850 is configured to rotatably engage the introducer tube 805 by way of, for example, a rotation element 875 (see, e.g., FIGS. 36, 37, and 39). The rotation element 875 may be configured to engage the introducer tube 805 such that the distal end 815 of the introducer tube 805 (and thus the distal end 770 of the tubular member 765) is disposed at, about, or in proximity to the distal end 860 of the tube sheath 850. That is, in some instances, the tube sheath 850 is configured to receive the introducer tube 805 of the introducer 800 therein such that the distal end 815 thereof is disposed about the distal end 860 of the tube sheath 850, wherein the imaging device (see, e.g., element 475 in FIG. 35) is thereby directed in an imaging direction outwardly of the distal end 860 of the tube sheath 850, and wherein the distal ends (see, e.g., element 505 in FIG. 35) of the light transmission devices (see, e.g., element 500 in FIG. 33) are arranged about the imaging device to direct the light transmitted from the light source (see, e.g., element 425 in FIG. 33) in the imaging direction.

In some aspects, at least the distal ends 770, 815 of the tubular member 765 of the imager 750 and the introducer tube 805 of the introducer 800 are configured to be flexible. Further, at least the distal end 860 of the tube sheath 850 may be configured to relatively rigid, at least compared to the distal ends 770, 815 of the tubular member 765 of the imager 750 and the introducer tube 805 of the introducer 800. In addition, at least the distal end 860 of the tube sheath 850 may be configured as a curve or a compound curve (see, e.g., FIGS. 36, 37, and 39). Accordingly, at least the distal ends 770, 815 of the tubular member 765 of the imager 750 and the introducer tube 805 of the introducer 800 will flex during longitudinal movement of the introducer tube 805 within the tube sheath 850, or longitudinal movement of the tubular member 765 of the imager 750 within the lumen 820 defined by the introducer tube 805 of the introducer 800, so as to conform to the curve or the compound curve of the distal end 860 of the tube sheath 850.

As such, for example, by a user grasping the body member 755 of the imager 750 in one hand, and the rotation element 875 associated with the tube sheath 850 in the other hand, the tube sheath 850 can be rotated with respect to the introducer tube 805/tubular member 765. In response, at least the distal ends 770, 815 of the tubular member 765 of the imager 750 and the introducer tube 805 of the introducer 800 will continue to conform to the distal end 860 of the tube sheath 850, upon rotation thereof (see, e.g., FIG. 39), and will therefore rotate, orbit, or gyrate about the longitudinal axis of the tube sheath 850 as directed by the curve or compound curve. Since, in such an arrangement, the imaging device (see, e.g., element 475 in FIG. 35) is directed outwardly of the distal end 860 of the tube sheath 850, due to the relation between the distal end 860 of the tube sheath 850 and at least the distal ends 770, 815 of the tubular member 765 of the imager 750 and the introducer tube 805 of the introducer 800, the imaging direction of the imaging device is altered in response to the rotation of the tube sheath 850 about the introducer tube 805. Accordingly, the imaging device (see, e.g., element 475 in FIG. 35) may be readily and accurately steered in regard to the particular imaging direction by merely rotating the tube sheath 850 about the introducer tube 805, without otherwise requiring a separate steering arrangement.

Certain embodiments of a method of the present invention include performing a medical procedure in an interior body region through the working channel device 40. For example, the medical procedure can be a gynecological procedure, a spinal procedure, or other procedure.

In some embodiments, a kit comprises at least one of a medical introducer; an imaging device; or a working channel device. In some embodiments a kit comprises a medical introducer and a working channel device. In some embodiment a kit comprises a working channel device inserted into a medical introducer.

The devices, systems, kits, and methods embodying the present invention can be adapted for use in many suitable interior body regions in humans and animals, wherever it may be desirable to provide support for a tissue. The illustrative embodiments are described in association with devices, systems, kits, and methods used, to access interior body regions such as the uterine cavity 64. For example, the medical device introduction system 10, and, in particular, the cooperating medical introducer 20, steerable working channel device 40, and imaging system 60 can be utilized to perform a hysteroscopy.

FIGS. 41 through 43 illustrate a more refined version of the system disclosed herein. As illustrated, rotation element 875 is rotated in order to impart rotation to tube sheath 850, which then imparts movement to the scope enclosed therein that has already been described herein. FIGS. 42 and 43 illustrate various scope and lumen arrangements provided herein.

FIG. 44 illustrates a system 900 with an introducer 904 with a sheath 902 located inside the scope lumen 906. The sheath may be a urethane inner sheath, where the sheath is removable by manipulation of the sheath flange seal that is accessible on an exterior of the introducer hub 908. In operation, the sheath flange 910 and 912 provides sealability against the device. This may allow for application of a biomarker element such as that shown in US Provisional Patent Application No. 62/375,421 filed on Aug. 15, 2016, the contents of which are incorporated herein. The introducer is shown in a "shortened" version in the drawings, but may be any appropriately configured length.

The disclosed assembly therefore allows quick and easy detection of biological contamination of a medical device on demand, i.e., such as during surgery. Accordingly, the disclosed assembly decreases the potential for using contaminated medical devices during medical procedures. Additionally, similar systems could be employed within any medical device, such as a syringe or other tools or working devices.

Some embodiments of the present invention may be utilized in applications other than those described herein. In some embodiments, the present invention may be used in other interior body regions or types of tissue. For example, certain embodiments of a medical device introduction system 10 of the present invention can be adapted for use in procedures related to the spinal column, for example, in the epidural space. In a particular embodiment, for example, the medical device introduction system according to the present invention may be utilized in an upright ventral epiduroscopic laser discectomy, in which the procedure is performed with the patient in an upright, symptomatic position such that diagnosis and treatment can be performed interactively with axial loading pressure on the affected intervertebral disc.

Features of a medical device introduction system and methods of the present invention may be accomplished singularly, or in combination, in one or more of the embodiments of the present invention. Although particular embodiments have been described, it should be recognized that these embodiments are merely illustrative of the principles of the present invention. Those of ordinary skill in the art will appreciate that a medical device introduction system 10 and method of the present invention may be constructed and implemented in other ways and embodiments. For example, in all cases, any of the features that are disclosed herein can be combined with any of the other features that are disclosed (even if those two or more distinct features appear in different sections of the above written, description). Accordingly, the description herein should not be read as limiting the present invention, as other embodiments also fall within the scope of the present invention.

What is claimed is:

1. A method of making an introducer, the method comprising:
    providing an elongate outer introducer having a rigid outer wall, the elongate introducer having a lumen extending therethrough with proximal and distal openings, the outer introducer having a distal portion that is angled at a non-zero angle relative to a proximal portion thereof;
    affixing a rotational hub at the proximal end of the outer introducer,
    placing a seal at the proximal opening of the introducer, wherein the seal is one of a duckbill seal or a one-way valve;
    assembling the introducer such that an elongate inner sheath is removably positioned within the outer introducer, the elongate inner sheath having proximal and distal ends, the inner sheath being more flexible than the outer introducer such that the inner sheath is configured to bend to substantially coaxially align with the distal and proximal portions of the outer introducer, the inner sheath having at least first and second lumens extending therethrough with proximal and distal openings;
    placing a closure across the distal opening of the first lumen, the first lumen being configured to receive an imaging shaft of an imaging device therein, and
    affixing a securing hub on the proximal end of the inner sheath, the securing hub being configured to engage the imaging device such that the inner sheath is rotationally fixed relative to the imaging device;
    wherein the rotational hub on the outer introducer engages the securing hub on the inner sheath when the inner sheath is disposed within the outer introducer and the imaging shaft is disposed within the inner sheath such that (i) the rotational hub is rotatable about a longitudinal axis of the proximal portion relative to the securing hub and (ii) at least a distal-most end of the imaging shaft is angled at the non-zero angle of the outer introducer and disposed at or proximal to the distal ends of the inner sheath and outer introducer, and
    wherein the outer introducer is effective as a uterine introducer.

2. The method of claim 1, wherein the inner sheath and the outer introducer are formed of translucent material.

3. The method of claim 1, wherein the closure across the distal opening of the first lumen is integrally formed with the inner sheath.

4. The method of claim 1, wherein the closure across the distal opening of the first lumen is formed with translucent material.

5. The method of claim 1, wherein the closure across the distal opening of the first lumen is formed with a second material different than the material forming the inner sheath.

6. The method of claim 1, wherein the inner sheath is formed with the first lumen, the second lumen, and at least one additional lumen.

7. The method of claim 1, further comprising providing at least third and fourth lumens in the inner sheath;
    wherein the first lumen is a viewing channel, the second lumen is a working channel, the third lumen is a fluid inflow channel, and the fourth lumen is a fluid outflow channel;
    wherein the working channel extends between the proximal end of the inner sheath and an opening at the distal end of the inner sheath, the working channel is configured to receive a surgical tool therethrough from the proximal end of the inner sheath and to extend from the distal end of the inner sheath; and
    wherein the fluid inflow and fluid outflow channels each define a fluid passage therethrough and each extend proximally from the distal end of the inner sheath to a point at least partway along the inner sheath, the fluid inflow channel is configured to provide inflows of fluid for disposition in a body cavity, and the fluid outflow channel is configured to receive outflows of fluid from the body cavity.

8. A method of making an introducer, the method comprising:
forming a first polymeric material into at least part of an elongate outer shaft with a lumen therethrough defined by rigid walls, a proximal end of the outer shaft being open, a central longitudinal axis of a distal portion of the outer shaft being angularly offset from a central longitudinal axis of a proximal portion of the outer shaft;
placing a proximal sealing mechanism in the proximal end of the outer shaft;
placing a first hub at the proximal end of the outer shaft;
forming a second polymeric material into an elongate inner sheath and removably inserting the inner sheath into the outer shaft, the inner sheath having proximal and distal ends, the second polymeric material having a lower durometer than the first polymeric material, the inner sheath having at least first and second lumens therethrough, the first and second lumens being non-coaxial relative to each other;
closing a distal opening of the first lumen with a closure element, the first lumen being configured to receive an imaging shaft of an imaging device therein; and
placing a second hub on the proximal end of the inner sheath, the second hub being configured to engage the imaging device such that the inner sheath is rotationally fixed relative to the imaging device;
wherein the first hub engages the second hub when the inner sheath is disposed within the outer shaft and the imaging shaft is disposed within the inner sheath such that (i) the first hub is rotatable about the central longitudinal axis of the proximal portion of the outer shaft relative to the second hub and (ii) at least a distal-most end of the imaging shaft is angularly offset from the central longitudinal axis of the proximal portion of the outer shaft and disposed at or proximal to the distal ends of the inner sheath and out shaft; and
wherein the introducer is a uterine introducer.

9. The method of claim 8, further comprising molding at least part of the outer shaft using a translucent material.

10. The method of claim 8, wherein the closure element is a cap formed of a translucent material.

11. The method of claim 8, wherein the closure element is a cap formed of the second polymeric material.

12. The method of claim 8, wherein the closure element is integrally formed with the inner sheath of the second polymeric material.

13. The method of claim 8, wherein the proximal sealing mechanism is one of a duckbill seal or a one-way valve.

14. The method of claim 8, further comprising molding at least part of the outer shaft using a third polymeric material.

15. The method of claim 14, wherein durometer values of the first polymeric material and the third polymeric material are different.

16. The method of claim 15, wherein the durometer value of the first polymeric material is lower than the durometer value of the third polymeric material, and the first polymeric material forms a distal portion of the outer shaft and the third polymeric material forms a proximal portion of the outer shaft.

17. The method of claim 8, further comprising forming at least third and fourth lumens in the inner sheath;
wherein the first lumen is a viewing channel, the second lumen is a working channel, the third lumen is a fluid inflow channel, and the fourth lumen is a fluid outflow channel;
wherein the working channel extends between the proximal end of the inner sheath and an opening at the distal end of the inner sheath, the working channel is configured to receive a surgical tool therethrough from the proximal end of the inner sheath and to extend from the distal end of the inner sheath; and
wherein the fluid inflow and fluid outflow channels each define a fluid passage therethrough and each extend proximally from the distal end of the inner sheath to a point at least partway along the inner sheath, the fluid inflow channel is configured to provide inflows of fluid for disposition in a body cavity, and the fluid outflow channel is configured to receive outflows of fluid from the body cavity.

18. A method of making an introducer, the method comprising:
providing an elongate outer shaft having a lumen therethrough, a distal portion of the lumen being permanently longitudinally angularly offset from a proximal portion of the lumen, distal and proximal ends of the outer shaft being open;
removably placing an elongate inner shaft into the outer shaft, the inner shaft having at least first and second lumens therethrough, the first and second lumens being non-coaxial relative to each other, distal and proximal ends of the first and second lumens being open;
placing a distal cap over at least a distal opening of the first lumen while leaving a distal opening of the second lumen open, a portion of the distal cap being formed of a translucent material, the first lumen being configured to receive an imaging shaft of an imaging device therein;
placing a proximal sealing mechanism in the proximal end of the outer shaft;
arranging a first hub at the proximal end of the outer shaft; and
arranging a second hub on the proximal end of the inner shaft, the second hub being configured to engage the imaging device such that the inner shaft is rotationally fixed relative to the imaging device,
wherein the first hub engages the second hub when the inner shaft is disposed within the outer shaft and the imaging shaft is disposed within the inner shaft such that (i) the first hub is rotatable about the central longitudinal axis of the proximal portion of the outer shaft relative to the second hub and (ii) at least a distal-most end of the imaging shaft is angularly offset from the proximal portion of the lumen of the outer shaft and disposed at or proximal to the distal ends of the inner and outer shafts; and
wherein the introducer is effective as a uterine introducer.

19. The method of claim 18, wherein a proximal end of the second hub is configured to removably engage the imaging device in a single pre-selected orientation to prevent axial translation along and axial rotation about a longitudinal axis of the inner shaft relative to the imaging device.

20. The method of claim 18, further comprising adding at least third and fourth lumens in the inner shaft;
wherein the first lumen is a viewing channel, the second lumen is a working channel, the third lumen is a fluid inflow channel, and the fourth lumen is a fluid outflow channel;
wherein the working channel extends between the proximal end of the inner sheath and an opening at the distal end of the inner sheath, the working channel is configured to receive a surgical tool therethrough from the proximal end of the inner sheath and to extend from the distal end of the inner sheath; and wherein the fluid inflow and fluid outflow channels each define a fluid passage therethrough and each extend proximally from the distal end of the inner sheath to a point at least partway along the inner sheath, the fluid inflow channel is configured to provide inflows of fluid for disposition in a body cavity, and the fluid outflow channel is configured to receive outflows of fluid from the body cavity.

* * * * *